United States Patent [19]
DeMaggio et al.

[11] Patent Number: 5,846,764
[45] Date of Patent: Dec. 8, 1998

[54] MATERIALS AND METHODS RELATING TO PROTEINS THAT INTERACT WITH CASEIN KINASE I

[75] Inventors: Anthony J. DeMaggio, Kirkland; Merl F. Hoekstra, Snohomish, both of Wash.

[73] Assignee: ICOS Corporation, Bothell, Wash.

[21] Appl. No.: 376,843

[22] Filed: Jan. 23, 1995

Related U.S. Application Data

[63] Continuation-in-part of Ser. No. 184,605, Jan. 21, 1994, abandoned.
[51] Int. Cl.$^6$ .............................. C12N 1/21; C12N 15/31; C12N 15/63; C12P 21/02
[52] U.S. Cl. ................ 435/69.1; 435/252.3; 435/254.11; 435/320.1; 435/325; 536/23.74
[58] Field of Search ....................... 536/23.74; 435/320.1, 435/240.2, 252.3, 254.11, 69.1, 325

[56] References Cited

PUBLICATIONS

Akiyama, et al., Molecular cloning and nucleotide sequence of the mut T mutator of *Escherichia coli* that causes A:T to C:G transversion, *Mol. Gen. Genet* (1987) 206:9–16.

Anderson, et al., "Human cellular src gene: nucleotide sequence and derived amino acid sequence of the region coding for the carboxy–terminal two–thirds of pp60$^{c-src}$," *Mol. Cel.Biol.* 5:1122–1129 (1985).

Bishop, et al., "Molecular themes in oncogenesis," *Cell* 64:235–248 (1991).

Bonner, et al., "The complete coding sequence of the human raf oncogene and the corresponding structure of c–raf–1 gene," *Nucl.Acids Res.* 14:1009–1015 (1986).

Brockman, et al., "Cell cycle dependent localization of casein kinase I to mitotic spindles," *Pros.Natl.Acad.Sci* (USA) 89:9454–9458 (1992).

Chein, et al., "The two–hybrid system: a method to identify and clone genes for a protein that interacts with a protein of interest," *Proc.Natl.Acad.Sci.*(USA) 88:9578–9582 (1991).

DeMaggio, et al., "The bidding yeast HRR25 gene product is a casein kinase I isoform," *Proc.Natl.Acad.Sci.*(USA) 89:7008–7012 (1992).

Durfee, et al., "The retinoblastoma protein associates with the protein phosphatase type 1 catalytic subunit," *Genes and Dev.* 7:555–569 (1993).

Edelman, et al., "Protein serine/threonine kinases," *Ann.Rev.Biochem.* 56:567–613 (1987).

Field, et al., "Purfication of a RAS–responsive adenyl cyclase complex from *Saccharomyces cerevisiae* by use of an epitope addition method," *Mol.Cell.Biol.* 8:2159–2165 (1988).

Fields and Song, "A novel genetic system to detect protein–protein interactions," *Nature* 340:245–246 (1989).

Graves, et al., "Molecular cloning, expression, and characterization of a 49–kilodalton casein kinase I isoform from rat testis," *J. Biol.Chem.* 268;6394–6401 (1993).

Guarente, "Yeast promoters and lacZ fusions designed to study expression of cloned genes in yeast," *Meth.Enzymol.* 101:181–191 (1983).

Hanks, et al., "Protein kinase catalytic domain sequence database: Indentification of conserved features of primary structure and classification of family members," *Meth.Enzymol.* 200:38–62 (1991).

Hoekstra, et al., "HHRR25, a putative protein kinase from budding yeast: association with repair of damaged DNA," *Science* 235:1031–1034 (1991).

Hoyt, et al., "Two *Saccharomyces cerevisiae* kinase–related gene products required for mitotic spindle assembly," *J.Cell. Biol.* 11:109–120 (1992).

(List continued on next page.)

*Primary Examiner*—Eric Grimes
*Attorney, Agent, or Firm*—Marshall, O'Toole, Gerstein, Murray & Borun

[57] ABSTRACT

The present invention relates generally to identification of proteins, designated TIH proteins, that interact with casein kinase I isoforms and to isolation of polynucleotides encoding the same.

10 Claims, 2 Drawing Sheets

```
yeast TIH1     SLSFPRGKISKDENDIDCCIREVKEEIGFDLTD    (SEQ ID NO: 49)
human Hum80DP  RWNGFGGKVQEGETIEDGARRELQEESGLTVDA    (SEQ ID NO: 50)
E.coli MutT    KLEFPGGKIEMGETREQAVVRELQEEVGITPQH    (SEQ IN NO: 51)
viral C11      DIIFPGGLPKNEEDPIMCLSREIKEEINIDSKD    (SEQ ID NO: 52)
viral VD10     DIIFPGGLPKNEEDPIMCLSREIKEEINIDSKD    (SEQ ID NO: 53)
```

OTHER PUBLICATIONS

Hubbard and Cohen, "On target with a new mewchanism for the regulation of protein phosphorylation," *TIBS* 18:172–177 (1993).

Ito, et al., "Transformation of intact yeast cells treated with alkli cations," *J.Bacteriol.* 153:162–168 (1983).

Herskowitz and Jenson, "Putting the HO gene to work: practical uses for mating–type switching," *Meth.Enzymol.* 194:132–146 (1991).

Luban, et al., "Human immunodeficiency virus type I gag protein binds to cyclophilins A and B", *Cell* 73:1067–1078 (1993).

Meluh and Rose, "KAR3, a kinesin–related gene required for yeast nuclear fusion," *Cell* 60:1029–1041 (1990).

Pearson and Kemp, "Protein kinase phosphorylation site sequences and consensus specificity motifs: tabulations," *Meth.Enzymol.* 200:62–81 (1991).

Riles, et al., "Physical maps of the six smallest chromosomes of *Saccharomyces cerevisae* at the resolution of 2.6 kilobase pairs," *Genetics* 134:81–150 (1993).

Roof, et al., "Kinesin–related proteins required for assembly of the mitotic spindle," *J.Cell.Biol.* 118:95–108 (1992).

Robinson, et al., "Yeast casein kinase I homologues: An essential pair," *Proc.Natl.Acad.Sci.USA* 89:28–32 (1992).

Rothstein, et al., "Targeting, disrupting, replacement, and allele rescue: integrative DNA transformation in yeast", *Meth.Enzymol.* 194:281–301 (1991).

Rowles, et al., "Purification of casein kinase I and isolation of cDNAs encoding multiple casein kinase I–like enzymes," *Proc.Natl.Acad.Sci.(USA)* 88:9548–9552 (1991).

Sakumi, et al., Cloning and expression of cDNA for a human enzyme that hydrolyzes 8–Oxo–dGTP, a mutagenic substrate for DNA sysntheis, *J.Biol.Chem.* 268:23524–23530 (1993).

Sherman and Hicks, "Micromainpulation and dissection of asci," *Meth.Enzymol.* 194:21–37 (1991).

Strayer, et al., "Sequence and analysis of a portion of the genomes of shope fibroma virus and malignant rabbit fibroma virus that is important for viral replication in lymphocytes," *Virology* 185:585–595 (1991).

Vojtek, et al., "Mammalian rats interacts directly with a serine/threonine kinase raf," *Cell* 74:205–214 (1991).

Wang, et al., "Two genes in *Saccharomyces cerevisiae* encode a membrane–bound form of casein kinase I," *Mol.Biol.Cell* 3:275–286 (1992).

Wallis, et al., A hyper–recombination mutation in S. cerevisiae indentifies a novel eukaryotic topoisomerase, *Cell* 58:409–419 (1989).

Watson, et al., "Human DNA sequence homologous to the transforming gene (mos) of Moloney murine sarcoma virus," *Proc.Natl.Sci. (USA)* 79:4078–4082 (1982).

Yang, et al., "A protein kinase substrate indentified by the two–hybrid system," *Science* 257: 681–682 (1992).

FIGURE 2

| | | |
|---|---|---|
| yeast TIH1 | SLSFPRGKISKDENDIDCCIREVKEEIGFDLTD | (SEQ ID NO: 49) |
| human Hum8ODP | RWNGFGGKVQEGETIEDGARRELQEESGLTVDA | (SEQ ID NO: 50) |
| E.coli MutT | KLEFPGGKIEMGETREQAVVRELQEEVGITPQH | (SEQ IN NO: 51) |
| viral C11 | DIIFPGGLPKNEEDPIMCLSREIKEEINIDSKD | (SEQ ID NO: 52) |
| viral VD10 | DIIFPGGLPKNEEDPIMCLSREIKEEINIDSKD | (SEQ ID NO: 53) |

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Arg  Arg  Xaa  Ser  Tyr
1                  5
```

( 2 ) INFORMATION FOR SEQ ID NO:2:

( i ) SEQUENCE CHARACTERISTICS:
        ( A ) LENGTH: 2625 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 796..2580

( x i ) SEQUENCE DESCRIPTION: SEQ ID NO:2:

```
CATTTTCTTA  ATTCTTTTAT  GTGCTTTTAC  TACTTTGTTT  AGTTCAAAAC  AATAGTCGTT     60

ATTCTTAGGT  ACTATAGCAT  AAGACAAGAA  AAGAAAATA   AGGGACAAAT  AACATTAGCA    120

GAAGTACGGT  ATATTTTACT  GTTACTTATA  TACTTTCAAG  AAGATGAGTT  AAATCGGTAG    180

CCAGTGTAGA  AAAATAATAA  TAAGGGTCAT  CGATCCTTCG  CATTTTATTA  TCCAATTAAA    240

GATACGAATC  ACGGCAAACT  ATATTCAAAG  CTCATAGATA  ATCGTCGTAA  GGCTGACACT    300

GCAGAAGAAA  AGTCATAATT  TGAATACTAG  CCGGTATGAA  ACTGTGATTG  ATTAACCTGG    360

GGTTACCTAA  AGAGAACATA  AGTAATACTC  ATGACAGAAT  CAAAACACAA  TACAAAATTT    420

ATCCGAACCT  CGGCCCGACT  GCGGCTCGCC  GGGAAAGGGG  ACAACCGCTT  CTATCCGTCG    480

ACTAACTTCA  TCGGCCCAAT  GGAAGCTATG  ATATGGGGAT  TTCCATTGAG  CCGATAGCAA    540

TGTAGGGTAA  TACTGTTGCG  TATATAGTGA  TAGTTATTGA  ATTTATTAC   CCTGCGGGAA    600

TATTGAGACA  TCACTAAGCA  CGAATTTTAC  GTCTGAGGAA  AGTTGAATGA  TGGCCAAATA    660

ACCAGGAAAA  ACAAATATTG  AATCCTTGTG  AAGGATTCCA  CAGTTGTTTA  ATCCTCCTTA    720

AGCTCACTTA  GTATCAATTG  TCTAAATAAT  ATTGCTTTGA  ATCTGAAAAA  AATAAAAGTA    780

CCTTCGCATT  AGACA ATG  TCA  CTG  CCG  CTA  CGA  CAC  GCA  TTG  GAG  AAC  GTT     831
                 Met  Ser  Leu  Pro  Leu  Arg  His  Ala  Leu  Glu  Asn  Val
                  1              5                          10

ACT  TCT  GTT  GAT  AGA  ATT  TTA  GAG  GAC  TTA  TTA  GTA  CGT  TTT  ATT  ATA      879
Thr  Ser  Val  Asp  Arg  Ile  Leu  Glu  Asp  Leu  Leu  Val  Arg  Phe  Ile  Ile
              15                       20                        25

AAT  TGT  CCG  AAT  GAA  GAT  TTA  TCG  AGT  GTC  GAG  AGA  GAG  TTA  TTT  CAT      927
Asn  Cys  Pro  Asn  Glu  Asp  Leu  Ser  Ser  Val  Glu  Arg  Glu  Leu  Phe  His
         30                       35                       40
```

-continued

| | | | | | | | | | | | | | | | | |
|---|---|---|---|---|---|---|---|---|---|---|---|---|---|---|---|---|
| TTT | GAA | GAA | GCC | TCA | TGG | TTT | TAC | ACG | GAT | TTC | ATC | AAA | TTG | ATG | AAT | 975 |
| Phe | Glu | Glu | Ala | Ser | Trp | Phe | Tyr | Thr | Asp | Phe | Ile | Lys | Leu | Met | Asn | |
| 45 | | | | 50 | | | | | 55 | | | | | | 60 | |
| CCA | ACT | TTA | CCC | TCC | CTA | AAG | ATT | AAA | TCA | TTT | GCT | CAA | TTG | ATC | ATA | 1023 |
| Pro | Thr | Leu | Pro | Ser | Leu | Lys | Ile | Lys | Ser | Phe | Ala | Gln | Leu | Ile | Ile | |
| | | | | 65 | | | | | 70 | | | | | 75 | | |
| AAA | CTA | TGT | CCT | CTG | GTT | TGG | AAA | TGG | GAC | ATA | AGA | GTG | GAT | GAG | GCA | 1071 |
| Lys | Leu | Cys | Pro | Leu | Val | Trp | Lys | Trp | Asp | Ile | Arg | Val | Asp | Glu | Ala | |
| | | | 80 | | | | | 85 | | | | | 90 | | | |
| CTC | CAG | CAA | TTC | TCC | AAG | TAT | AAG | AAA | AGT | ATA | CCG | GTG | AGG | GGC | GCT | 1119 |
| Leu | Gln | Gln | Phe | Ser | Lys | Tyr | Lys | Lys | Ser | Ile | Pro | Val | Arg | Gly | Ala | |
| | | 95 | | | | | | 100 | | | | | 105 | | | |
| GCC | ATA | TTT | AAC | GAG | AAC | CTG | AGT | AAA | ATT | TTA | TTG | GTA | CAG | GGT | ACT | 1167 |
| Ala | Ile | Phe | Asn | Glu | Asn | Leu | Ser | Lys | Ile | Leu | Leu | Val | Gln | Gly | Thr | |
| | 110 | | | | | 115 | | | | | 120 | | | | | |
| GAA | TCG | GAT | TCT | TTG | TCA | TTC | CCA | AGG | GGG | AAG | ATA | TCT | AAA | GAT | GAA | 1215 |
| Glu | Ser | Asp | Ser | Leu | Ser | Phe | Pro | Arg | Gly | Lys | Ile | Ser | Lys | Asp | Glu | |
| 125 | | | | | 130 | | | | | 135 | | | | | 140 | |
| AAT | GAC | ATA | GAT | TGT | TGC | ATT | AGA | GAA | GTG | AAA | GAA | GAA | ATT | GGT | TTC | 1263 |
| Asn | Asp | Ile | Asp | Cys | Cys | Ile | Arg | Glu | Val | Lys | Glu | Glu | Ile | Gly | Phe | |
| | | | | 145 | | | | | 150 | | | | | 155 | | |
| GAT | TTG | ACG | GAC | TAT | ATT | GAC | GAC | AAC | CAA | TTC | ATT | GAA | AGA | AAT | ATT | 1311 |
| Asp | Leu | Thr | Asp | Tyr | Ile | Asp | Asp | Asn | Gln | Phe | Ile | Glu | Arg | Asn | Ile | |
| | | | 160 | | | | | 165 | | | | | 170 | | | |
| CAA | GGT | AAA | AAT | TAC | AAA | ATA | TTT | TTG | ATA | TCT | GGT | GTT | TCA | GAA | GTC | 1359 |
| Gln | Gly | Lys | Asn | Tyr | Lys | Ile | Phe | Leu | Ile | Ser | Gly | Val | Ser | Glu | Val | |
| | | 175 | | | | | 180 | | | | | 185 | | | | |
| TTC | AAT | TTT | AAA | CCT | CAA | GTT | AGA | AAT | GAA | ATT | GAT | AAG | ATA | GAA | TGG | 1407 |
| Phe | Asn | Phe | Lys | Pro | Gln | Val | Arg | Asn | Glu | Ile | Asp | Lys | Ile | Glu | Trp | |
| | 190 | | | | | 195 | | | | | 200 | | | | | |
| TTC | GAT | TTT | AAG | AAA | ATT | TCT | AAA | ACA | ATG | TAC | AAA | TCA | AAT | ATC | AAG | 1455 |
| Phe | Asp | Phe | Lys | Lys | Ile | Ser | Lys | Thr | Met | Tyr | Lys | Ser | Asn | Ile | Lys | |
| 205 | | | | 210 | | | | | 215 | | | | | | 220 | |
| TAT | TAT | CTG | ATT | AAT | TCC | ATG | ATG | AGA | CCC | TTA | TCA | ATG | TGG | TTA | AGG | 1503 |
| Tyr | Tyr | Leu | Ile | Asn | Ser | Met | Met | Arg | Pro | Leu | Ser | Met | Trp | Leu | Arg | |
| | | | | 225 | | | | | 230 | | | | | | 235 | |
| CAT | CAG | AGG | CAA | ATA | AAA | AAT | GAA | GAT | CAA | TTG | AAA | TCC | TAT | GCG | GAA | 1551 |
| His | Gln | Arg | Gln | Ile | Lys | Asn | Glu | Asp | Gln | Leu | Lys | Ser | Tyr | Ala | Glu | |
| | | | 240 | | | | | 245 | | | | | 250 | | | |
| GAA | CAA | TTG | AAA | TTG | TTG | TTG | GGT | ATC | ACT | AAG | GAG | GAG | CAG | ATT | GAT | 1599 |
| Glu | Gln | Leu | Lys | Leu | Leu | Leu | Gly | Ile | Thr | Lys | Glu | Glu | Gln | Ile | Asp | |
| | | 255 | | | | | 260 | | | | | 265 | | | | |
| CCC | GGT | AGA | GAG | TTG | CTG | AAT | ATG | TTA | CAT | ACT | GCA | GTG | CAA | GCT | AAC | 1647 |
| Pro | Gly | Arg | Glu | Leu | Leu | Asn | Met | Leu | His | Thr | Ala | Val | Gln | Ala | Asn | |
| | 270 | | | | | 275 | | | | | 280 | | | | | |
| AGT | AAT | AAT | AAT | GCG | GTC | TCC | AAC | GGA | CAG | GTA | CCC | TCG | AGC | CAA | GAG | 1695 |
| Ser | Asn | Asn | Asn | Ala | Val | Ser | Asn | Gly | Gln | Val | Pro | Ser | Ser | Gln | Glu | |
| 285 | | | | | 290 | | | | | 295 | | | | | 300 | |
| CTT | CAG | CAT | TTG | AAA | GAG | CAA | TCA | GGA | GAA | CAC | AAC | CAA | CAG | AAG | GAT | 1743 |
| Leu | Gln | His | Leu | Lys | Glu | Gln | Ser | Gly | Glu | His | Asn | Gln | Gln | Lys | Asp | |
| | | | | 305 | | | | | 310 | | | | | 315 | | |
| CAG | CAG | TCA | TCG | TTT | TCT | TCT | CAA | CAA | CAA | CCT | TCA | ATA | TTT | CCA | TCT | 1791 |
| Gln | Gln | Ser | Ser | Phe | Ser | Ser | Gln | Gln | Gln | Pro | Ser | Ile | Phe | Pro | Ser | |
| | | 320 | | | | | 325 | | | | | 330 | | | | |
| CTT | TCT | GAA | CCG | TTT | GCT | AAC | AAT | AAG | AAT | GTT | ATA | CCA | CCT | ACT | ATG | 1839 |
| Leu | Ser | Glu | Pro | Phe | Ala | Asn | Asn | Lys | Asn | Val | Ile | Pro | Pro | Thr | Met | |
| | | 335 | | | | | 340 | | | | | 345 | | | | |
| CCA | ATG | GCT | AAC | GTA | TTC | ATG | TCA | AAT | CCT | CAA | TTG | TTT | GCG | ACA | ATG | 1887 |
| Pro | Met | Ala | Asn | Val | Phe | Met | Ser | Asn | Pro | Gln | Leu | Phe | Ala | Thr | Met | |
| 350 | | | | | 355 | | | | | 360 | | | | | | |

| | | | | | | | | | | | | | | | | |
|---|---|---|---|---|---|---|---|---|---|---|---|---|---|---|---|---|
| AAT | GGC | CAG | CCT | TTT | GCA | CCT | TTC | CCA | TTT | ATG | TTA | CCA | TTA | ACT | AAC | 1935 |
| Asn | Gly | Gln | Pro | Phe | Ala | Pro | Phe | Pro | Phe | Met | Leu | Pro | Leu | Thr | Asn | |
| 365 | | | | 370 | | | | | 375 | | | | | | 380 | |
| AAT | AGT | AAT | AGC | GCT | AAC | CCT | ATT | CCA | ACT | CCG | GTC | CCC | CCT | AAT | TTT | 1983 |
| Asn | Ser | Asn | Ser | Ala | Asn | Pro | Ile | Pro | Thr | Pro | Val | Pro | Pro | Asn | Phe | |
| | | | | 385 | | | | | 390 | | | | | 395 | | |
| AAT | GCT | CCT | CCG | AAT | CCG | ATG | GCT | TTT | GGT | GTT | CCA | AAC | ATG | CAT | AAC | 2031 |
| Asn | Ala | Pro | Pro | Asn | Pro | Met | Ala | Phe | Gly | Val | Pro | Asn | Met | His | Asn | |
| | | | 400 | | | | 405 | | | | | | 410 | | | |
| CTT | TCT | GGA | CCA | GCA | GTA | TCT | CAA | CCG | TTT | TCC | TTG | CCT | CCT | GCT | CCT | 2079 |
| Leu | Ser | Gly | Pro | Ala | Val | Ser | Gln | Pro | Phe | Ser | Leu | Pro | Pro | Ala | Pro | |
| | | 415 | | | | | 420 | | | | | 425 | | | | |
| TTA | CCG | AGG | GAC | TCT | GGT | TAC | AGC | AGC | TCC | TCC | CCT | GGG | CAG | TTG | TTA | 2127 |
| Leu | Pro | Arg | Asp | Ser | Gly | Tyr | Ser | Ser | Ser | Ser | Pro | Gly | Gln | Leu | Leu | |
| | 430 | | | | | 435 | | | | | 440 | | | | | |
| GAT | ATA | CTA | AAT | TCG | AAA | AAG | CCT | GAC | AGC | AAC | GTG | CAA | TCA | AGC | AAA | 2175 |
| Asp | Ile | Leu | Asn | Ser | Lys | Lys | Pro | Asp | Ser | Asn | Val | Gln | Ser | Ser | Lys | |
| 445 | | | | | 450 | | | | | 455 | | | | | 460 | |
| AAG | CCA | AAG | CTT | AAA | ATC | TTA | CAG | AGA | GGA | ACG | GAC | TTG | AAT | TCA | CTC | 2223 |
| Lys | Pro | Lys | Leu | Lys | Ile | Leu | Gln | Arg | Gly | Thr | Asp | Leu | Asn | Ser | Leu | |
| | | | | 465 | | | | | 470 | | | | | 475 | | |
| AAG | CAA | AAC | AAT | AAT | GAT | GAA | ACT | GCT | CAT | TCA | AAC | TCT | CAA | GCT | TTG | 2271 |
| Lys | Gln | Asn | Asn | Asn | Asp | Glu | Thr | Ala | His | Ser | Asn | Ser | Gln | Ala | Leu | |
| | | | 480 | | | | | 485 | | | | | 490 | | | |
| CTA | GAT | TTG | TTG | AAA | AAA | CCA | ACA | TCA | TCG | CAG | AAG | ATA | CAC | GCT | TCC | 2319 |
| Leu | Asp | Leu | Leu | Lys | Lys | Pro | Thr | Ser | Ser | Gln | Lys | Ile | His | Ala | Ser | |
| | | 495 | | | | | 500 | | | | | 505 | | | | |
| AAA | CCA | GAT | ACT | TCC | TTT | TTA | CCA | AAT | GAC | TCC | GTA | TCT | GGT | ATA | CAA | 2367 |
| Lys | Pro | Asp | Thr | Ser | Phe | Leu | Pro | Asn | Asp | Ser | Val | Ser | Gly | Ile | Gln | |
| | 510 | | | | | 515 | | | | | 520 | | | | | |
| GAT | GCA | GAA | TAT | GAA | GAT | TTC | GAG | AGT | AGT | TCA | GAT | GAA | GAG | GTG | GAG | 2415 |
| Asp | Ala | Glu | Tyr | Glu | Asp | Phe | Glu | Ser | Ser | Ser | Asp | Glu | Glu | Val | Glu | |
| 525 | | | | | 530 | | | | | 535 | | | | | 540 | |
| ACA | GCT | AGA | GAT | GAA | AGA | AAT | TCA | TTG | AAT | GTA | GAT | ATT | GGG | GTG | AAC | 2463 |
| Thr | Ala | Arg | Asp | Glu | Arg | Asn | Ser | Leu | Asn | Val | Asp | Ile | Gly | Val | Asn | |
| | | | | 545 | | | | | 550 | | | | | 555 | | |
| GTT | ATG | CCA | AGC | GAA | AAA | GAC | AGC | CGA | AGA | AGT | CAA | AAG | GAA | AAA | CCA | 2511 |
| Val | Met | Pro | Ser | Glu | Lys | Asp | Ser | Arg | Arg | Ser | Gln | Lys | Glu | Lys | Pro | |
| | | | 560 | | | | | 565 | | | | | 570 | | | |
| AGG | AAC | GAC | GCA | AGC | AAA | ACA | AAC | TTG | AAC | GCT | TCT | GCA | GAA | TCT | AAT | 2559 |
| Arg | Asn | Asp | Ala | Ser | Lys | Thr | Asn | Leu | Asn | Ala | Ser | Ala | Glu | Ser | Asn | |
| | | 575 | | | | | 580 | | | | | 585 | | | | |
| AGT | GTA | GAA | TGG | GGG | GCT | GGG | TAAATCTTCA | CCCTCCGACT | TCAGAGTAAC | | | | | | | 2610 |
| Ser | Val | Glu | Trp | Gly | Ala | Gly | | | | | | | | | | |
| | 590 | | | | | 595 | | | | | | | | | | |
| ACAGAATCCA | CAGTA | | | | | | | | | | | | | | | 2625 |

( 2 ) INFORMATION FOR SEQ ID NO:3:

( i ) SEQUENCE CHARACTERISTICS:
        ( A ) LENGTH: 595 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Ser | Leu | Pro | Leu | Arg | His | Ala | Leu | Glu | Asn | Val | Thr | Ser | Val | Asp |
| 1 | | | | 5 | | | | | 10 | | | | | 15 | |
| Arg | Ile | Leu | Glu | Asp | Leu | Leu | Val | Arg | Phe | Ile | Ile | Asn | Cys | Pro | Asn |
| | | | 20 | | | | | 25 | | | | | 30 | | |

-continued

```
Glu  Asp  Leu  Ser  Ser  Val  Glu  Arg  Glu  Leu  Phe  His  Phe  Glu  Glu  Ala
          35                  40                       45

Ser  Trp  Phe  Tyr  Thr  Asp  Phe  Ile  Lys  Leu  Met  Asn  Pro  Thr  Leu  Pro
     50                  55                  60

Ser  Leu  Lys  Ile  Lys  Ser  Phe  Ala  Gln  Leu  Ile  Ile  Lys  Leu  Cys  Pro
65                  70                  75                                 80

Leu  Val  Trp  Lys  Trp  Asp  Ile  Arg  Val  Asp  Glu  Ala  Leu  Gln  Gln  Phe
               85                       90                            95

Ser  Lys  Tyr  Lys  Lys  Ser  Ile  Pro  Val  Arg  Gly  Ala  Ala  Ile  Phe  Asn
               100                 105                      110

Glu  Asn  Leu  Ser  Lys  Ile  Leu  Leu  Val  Gln  Gly  Thr  Glu  Ser  Asp  Ser
          115                 120                 125

Leu  Ser  Phe  Pro  Arg  Gly  Lys  Ile  Ser  Lys  Asp  Glu  Asn  Asp  Ile  Asp
     130                 135                      140

Cys  Cys  Ile  Arg  Glu  Val  Lys  Glu  Glu  Ile  Gly  Phe  Asp  Leu  Thr  Asp
145                      150                      155                      160

Tyr  Ile  Asp  Asp  Asn  Gln  Phe  Ile  Glu  Arg  Asn  Ile  Gln  Gly  Lys  Asn
                    165                      170                      175

Tyr  Lys  Ile  Phe  Leu  Ile  Ser  Gly  Val  Ser  Glu  Val  Phe  Asn  Phe  Lys
               180                 185                      190

Pro  Gln  Val  Arg  Asn  Glu  Ile  Asp  Lys  Ile  Glu  Trp  Phe  Asp  Phe  Lys
          195                 200                      205

Lys  Ile  Ser  Lys  Thr  Met  Tyr  Lys  Ser  Asn  Ile  Lys  Tyr  Tyr  Leu  Ile
     210                      215                 220

Asn  Ser  Met  Met  Arg  Pro  Leu  Ser  Met  Trp  Leu  Arg  His  Gln  Arg  Gln
225                      230                 235                           240

Ile  Lys  Asn  Glu  Asp  Gln  Leu  Lys  Ser  Tyr  Ala  Glu  Glu  Gln  Leu  Lys
               245                      250                      255

Leu  Leu  Leu  Gly  Ile  Thr  Lys  Glu  Glu  Gln  Ile  Asp  Pro  Gly  Arg  Glu
          260                      265                 270

Leu  Leu  Asn  Met  Leu  His  Thr  Ala  Val  Gln  Ala  Asn  Ser  Asn  Asn  Asn
          275                      280                 285

Ala  Val  Ser  Asn  Gly  Gln  Val  Pro  Ser  Ser  Gln  Glu  Leu  Gln  His  Leu
     290                 295                      300

Lys  Glu  Gln  Ser  Gly  Glu  His  Asn  Gln  Gln  Lys  Asp  Gln  Gln  Ser  Ser
305                      310                      315                      320

Phe  Ser  Ser  Gln  Gln  Gln  Pro  Ser  Ile  Phe  Pro  Ser  Leu  Ser  Glu  Pro
               325                      330                      335

Phe  Ala  Asn  Asn  Lys  Asn  Val  Ile  Pro  Pro  Thr  Met  Pro  Met  Ala  Asn
               340                 345                      350

Val  Phe  Met  Ser  Asn  Pro  Gln  Leu  Phe  Ala  Thr  Met  Asn  Gly  Gln  Pro
          355                      360                      365

Phe  Ala  Pro  Phe  Pro  Phe  Met  Leu  Pro  Leu  Thr  Asn  Asn  Ser  Asn  Ser
     370                      375                      380

Ala  Asn  Pro  Ile  Pro  Thr  Pro  Val  Pro  Pro  Asn  Phe  Asn  Ala  Pro  Pro
385                           390                      395                 400

Asn  Pro  Met  Ala  Phe  Gly  Val  Pro  Asn  Met  His  Asn  Leu  Ser  Gly  Pro
                    405                      410                      415

Ala  Val  Ser  Gln  Pro  Phe  Ser  Leu  Pro  Pro  Ala  Pro  Leu  Pro  Arg  Asp
               420                      425                      430

Ser  Gly  Tyr  Ser  Ser  Ser  Ser  Pro  Gly  Gln  Leu  Leu  Asp  Ile  Leu  Asn
          435                      440                      445

Ser  Lys  Lys  Pro  Asp  Ser  Asn  Val  Gln  Ser  Ser  Lys  Lys  Pro  Lys  Leu
     450                      455                      460
```

| Lys | Ile | Leu | Gln | Arg | Gly | Thr | Asp | Leu | Asn | Ser | Leu | Lys | Gln | Asn | Asn |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Asn | Asp | Glu | Thr | Ala | His | Ser | Asn | Ser | Gln | Ala | Leu | Leu | Asp | Leu | Leu |
|-----|-----|-----|-----|-----|-----|-----|-----|-----|-----|-----|-----|-----|-----|-----|-----|
|     |     |     |     | 485 |     |     |     |     | 490 |     |     |     |     | 495 |     |

| Lys | Lys | Pro | Thr | Ser | Ser | Gln | Lys | Ile | His | Ala | Ser | Lys | Pro | Asp | Thr |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Ser | Phe | Leu | Pro | Asn | Asp | Ser | Val | Ser | Gly | Ile | Gln | Asp | Ala | Glu | Tyr |
|-----|-----|-----|-----|-----|-----|-----|-----|-----|-----|-----|-----|-----|-----|-----|-----|
|     |     | 515 |     |     |     |     | 520 |     |     |     |     | 525 |     |     |     |

| Glu | Asp | Phe | Glu | Ser | Ser | Ser | Asp | Glu | Glu | Val | Glu | Thr | Ala | Arg | Asp |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

| Glu | Arg | Asn | Ser | Leu | Asn | Val | Asp | Ile | Gly | Val | Asn | Val | Met | Pro | Ser |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Glu | Lys | Asp | Ser | Arg | Arg | Ser | Gln | Lys | Glu | Lys | Pro | Arg | Asn | Asp | Ala |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

| Ser | Lys | Thr | Asn | Leu | Asn | Ala | Ser | Ala | Glu | Ser | Asn | Ser | Val | Glu | Trp |
|-----|-----|-----|-----|-----|-----|-----|-----|-----|-----|-----|-----|-----|-----|-----|-----|
|     |     |     | 580 |     |     |     |     | 585 |     |     |     |     | 590 |     |     |

| Gly | Ala | Gly |
|-----|-----|-----|
|     |     | 595 |

( 2 ) INFORMATION FOR SEQ ID NO:4:

( i ) SEQUENCE CHARACTERISTICS:
        ( A ) LENGTH: 6854 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2050..4053

( x i ) SEQUENCE DESCRIPTION: SEQ ID NO:4:

| AGCTTCTCCC | TTTTCCTTCA | GTGCTGCTAC | TCTCTGCTCT | CCACTTAAGT | GTTACAATTA | 60 |
| ATTTGCAGCT | AGTTTGCAGT | TCGTACAACC | TCGCCTATTC | TTGTAACGAA | GAAGAACGTA | 120 |
| TTTATAATAT | TGGGCTGTAA | TGTGTTGAGT | TTAGTAATAG | ATAAAGTAGG | ACAGAGTTCT | 180 |
| GTCTTTGTTT | ATCTATGGGG | TTCAGAGTGA | TAAGGGGCAG | GATAAGGAAG | TTAAAAAAAA | 240 |
| AAAGGTTACG | TTATATAACG | AAAGAAAAGA | AACGAGCGAA | GTGCCAACTA | TAGCCCAATA | 300 |
| TCAAGAATGC | AAGTCAGCAA | AGTACAGTAA | TCGTATGAAG | ATACGCGATG | CGTAATATCC | 360 |
| CTCAAGGGCT | CCGGATCAGA | AAAGCTAAGG | GAAGATCCTT | ACATTACACG | GCGTGCGACA | 420 |
| GACTCGAACC | ACAGCTAACT | TCTCGTGAAA | AGATGGCTTC | AACTTCGCTC | TTGCAATAAC | 480 |
| TTTGAAACAC | ACGAACAAAG | GTTTATTGCG | CTTGATTAAC | GTTGGAAGTA | TATGATACTA | 540 |
| ATACTACTTT | GTTCTCTAAG | TCATCGCTAT | ATGTTTATCT | CGAGGAAAAG | GTGCACGGCG | 600 |
| GTACACAATT | ACTTCGCCGT | TTCGGGTAAA | ACAAGTGTTA | CATTTATAAT | ATATATGTAT | 660 |
| ATATGTATGT | GCGCGTAAGT | ATATGCCGTT | CATAACAAAT | CATCTTCTTG | TTGCTGGATG | 720 |
| GACTCCTTAA | TTTTATTCAA | AATGGTAATT | TTCCATTTAT | CTAGTCTCAT | AAAATTGTCA | 780 |
| AACTCCTTAC | AGTGTTCGCT | TAGCTGCTCG | CTATCACCTT | CATTAACAGC | ATCGATTAAA | 840 |
| CTTTTCAAGA | AATTTGACTC | CCTTGAATCC | GCAAAATTCG | GATCTTCACT | TTGACCCTCT | 900 |
| TGTAAAGTTC | TTGCAGCAGC | GACTGCATCA | GTAGCAGCTA | GCTGACAAAG | CCCTTTTTTT | 960 |
| AGGAAGTAAT | CCTTCAAACT | CCATTGGCTC | AATCTATTGC | CCATGCTGCT | CTTGATCAAC | 1020 |
| TTCGAATATA | TATCACTTGC | TTCAATATAT | TGACCGTCAA | GAGCCTTTAG | ATCTGCGCAT | 1080 |

```
TTGATAAAAC ACTTATTCGA TAATGCTACC GACTGGTCTT GGGCATACCA CTCACCAGCG      1140

AGCTCATAGC AATCTATAGC TTTTGCATAG TCATGCAAAT CATTTTCTAG AATTTCTCCA      1200

AGCTCAAACT TGAAATTAGC ACCTCTCCGG AACTGCCCCC TATGAGTAAA AATTTGAATA      1260

GCATTTTCTA ATGAATCCAC GGCGTTCACA GAGTTTCCAC CGCTTTTAAA GCATTTATAA      1320

GCCTCTACGT AGGTATTTCC TGCTTCGTCT TCATTACCAG CCTTTTCTG ATAGTCAGCA       1380

GCTTTCAAAA ACGAGTCTCC TGCCAAGTTT AACTCTTTTC TTAGACGGTA AATGGTGGCT     1440

GCTTGGACAC AAAGATCAGC AGCCTCCTCA AACTTGTATG AATCAGAACC GCTAAACAAT     1500

TTCATGAAAC CCGATGAAGG AACACCCTTC TTCTCAGCCT TAACACAACG GGAAATATCA     1560

ATTCCCGTAT TTCAATGTTA GTAATTTGCC TTCGTAAATT ACGGAATCAC ATAGCTTTCA     1620

TTTTGTTCCT TTGATATATT TCCCTACTAC ATACTCTTTT CAATAACTCT ACAGGGTCTG     1680

ACATTTTTAA CTTTCAGGTT AATGATGGTG TTCTTACTAT ATTCTGAGT CGTACAGAAG      1740

TTAGTTCAGA TAAACTGCTT CGGTGCTGCC CACTTCTTAT CATTACTTCA ACTTTACCTT    1800

CCCTATACCT GTGTGTCCTT ATTAATTCAA GTTAATCCGA GGTAATAGAT TAGGGTAACC    1860

TTCAATGATG TCACGAAACA CGGATGCTGC AACTTTGCGA TTTTTTCCTG GAAAAGAATA    1920

ACAATTAAAG GCAGCCTTTC AGCTGAGATT ACCAGCAGGT CTTTGGAGAT TAGCGCAAGA    1980

AGAAGTGTGA TATAGTACTC ATAGAGGCAG GCTACAGACT AGGGAAAGCG TGTTCAACAA    2040

CAATAAGAA ATG GAG ACC AGT TCT TTT GAG AAT GCT CCT CCT GCA GCC          2088
           Met Glu Thr Ser Ser Phe Glu Asn Ala Pro Pro Ala Ala
             1               5                  10

ATC AAT GAT GCT CAG GAT AAT AAT ATA AAT ACG GAG ACT AAT GAC CAG       2136
Ile Asn Asp Ala Gln Asp Asn Asn Ile Asn Thr Glu Thr Asn Asp Gln
        15                  20                  25

GAA ACA AAT CAG CAA TCT ATC GAA ACT AGA GAT GCA ATT GAC AAA GAA       2184
Glu Thr Asn Gln Gln Ser Ile Glu Thr Arg Asp Ala Ile Asp Lys Glu
 30                  35                  40                  45

AAC GGT GTG CAA ACG GAA ACT GGT GAG AAC TCT GCA AAA AAT GCC GAA       2232
Asn Gly Val Gln Thr Glu Thr Gly Glu Asn Ser Ala Lys Asn Ala Glu
                50                  55                  60

CAA AAC GTT TCT TCT ACA AAT TTG AAT AAT GCC CCC ACC AAT GGT GCT       2280
Gln Asn Val Ser Ser Thr Asn Leu Asn Asn Ala Pro Thr Asn Gly Ala
         65                  70                  75

TTG GAC GAT GAT GTT ATC CCA AAT GCT ATT GTT ATT AAA AAC ATT CCG       2328
Leu Asp Asp Asp Val Ile Pro Asn Ala Ile Val Ile Lys Asn Ile Pro
             80                  85                  90

TTT GCT ATT AAA AAA GAG CAA TTG TTA GAC ATT ATT GAA GAA ATG GAT       2376
Phe Ala Ile Lys Lys Glu Gln Leu Leu Asp Ile Ile Glu Glu Met Asp
         95                 100                 105

CTT CCC CTT CCT TAT GCC TTC AAT TAC CAC TTT GAT AAC GGT ATT TTC       2424
Leu Pro Leu Pro Tyr Ala Phe Asn Tyr His Phe Asp Asn Gly Ile Phe
110                 115                 120                 125

AGA GGA CTA GCC TTT GCG AAT TTC ACC ACT CCT GAA GAA ACT ACT CAA       2472
Arg Gly Leu Ala Phe Ala Asn Phe Thr Thr Pro Glu Glu Thr Thr Gln
             130                 135                 140

GTG ATA ACT TCT TTG AAT GGA AAG GAA ATC AGC GGG AGG AAA TTG AAA       2520
Val Ile Thr Ser Leu Asn Gly Lys Glu Ile Ser Gly Arg Lys Leu Lys
                 145                 150                 155

GTG GAA TAT AAA AAA ATG CTT CCC CAA GCT GAA AGA GAA AGA ATC GAG       2568
Val Glu Tyr Lys Lys Met Leu Pro Gln Ala Glu Arg Glu Arg Ile Glu
             160                 165                 170

AGG GAG AAG AGA GAG AAA AGA GGA CAA TTA GAA GAA CAA CAC AGA TCG       2616
Arg Glu Lys Arg Glu Lys Arg Gly Gln Leu Glu Glu Gln His Arg Ser
 175                 180                 185
```

| | | | | | | | | | | | | | | | | |
|---|---|---|---|---|---|---|---|---|---|---|---|---|---|---|---|---|
| TCA | TCT | AAT | CTT | TCT | TTG | GAT | TCT | TTA | TCT | AAA | ATG | AGT | GGA | AGC | GGA | 2664 |
| Ser | Ser | Asn | Leu | Ser | Leu | Asp | Ser | Leu | Ser | Lys | Met | Ser | Gly | Ser | Gly | |
| 190 | | | | 195 | | | | | | 200 | | | | | 205 | |
| AAC | AAT | AAT | ACT | TCT | AAC | AAT | CAA | TTA | TTC | TCG | ACT | CTA | ATG | AAC | GGC | 2712 |
| Asn | Asn | Asn | Thr | Ser | Asn | Asn | Gln | Leu | Phe | Ser | Thr | Leu | Met | Asn | Gly | |
| | | | | 210 | | | | | 215 | | | | | 220 | | |
| ATT | AAT | GCT | AAT | AGC | ATG | ATG | AAC | AGT | CCA | ATG | AAT | AAT | ACC | ATT | AAC | 2760 |
| Ile | Asn | Ala | Asn | Ser | Met | Met | Asn | Ser | Pro | Met | Asn | Asn | Thr | Ile | Asn | |
| | | | | 225 | | | | | 230 | | | | | 235 | | |
| AAT | AAC | AGT | TCT | AAT | AAC | AAC | AAT | AGT | GGT | AAC | ATC | ATT | CTG | AAC | CAA | 2808 |
| Asn | Asn | Ser | Ser | Asn | Asn | Asn | Asn | Ser | Gly | Asn | Ile | Ile | Leu | Asn | Gln | |
| | | | 240 | | | | | 245 | | | | | 250 | | | |
| CCT | TCA | CTT | TCT | GCC | CAA | CAT | ACT | TCT | TCA | TCG | TTG | TAC | CAA | ACA | AAC | 2856 |
| Pro | Ser | Leu | Ser | Ala | Gln | His | Thr | Ser | Ser | Ser | Leu | Tyr | Gln | Thr | Asn | |
| | | 255 | | | | | 260 | | | | | 265 | | | | |
| GTT | AAT | AAT | CAA | GCC | CAG | ATG | TCC | ACT | GAG | AGA | TTT | TAT | GCG | CCT | TTA | 2904 |
| Val | Asn | Asn | Gln | Ala | Gln | Met | Ser | Thr | Glu | Arg | Phe | Tyr | Ala | Pro | Leu | |
| 270 | | | | | 275 | | | | | 280 | | | | | 285 | |
| CCA | TCA | ACT | TCC | ACT | TTG | CCT | CTC | CCA | CCC | CAA | CAA | CTG | GAC | TTC | AAT | 2952 |
| Pro | Ser | Thr | Ser | Thr | Leu | Pro | Leu | Pro | Pro | Gln | Gln | Leu | Asp | Phe | Asn | |
| | | | | 290 | | | | | 295 | | | | | 300 | | |
| GAC | CCT | GAC | ACT | TTG | GAA | ATT | TAT | TCC | CAA | TTA | TTG | TTA | TTT | AAG | GAT | 3000 |
| Asp | Pro | Asp | Thr | Leu | Glu | Ile | Tyr | Ser | Gln | Leu | Leu | Leu | Phe | Lys | Asp | |
| | | | 305 | | | | | 310 | | | | | 315 | | | |
| AGA | GAA | AAG | TAT | TAT | TAC | GAG | TTG | GCT | TAT | CCC | ATG | GGT | ATA | TCC | GCT | 3048 |
| Arg | Glu | Lys | Tyr | Tyr | Tyr | Glu | Leu | Ala | Tyr | Pro | Met | Gly | Ile | Ser | Ala | |
| | | 320 | | | | | 325 | | | | | 330 | | | | |
| TCC | CAC | AAG | AGA | ATT | ATC | AAT | GTT | TTG | TGC | TCG | TAC | TTA | GGG | CTA | GTA | 3096 |
| Ser | His | Lys | Arg | Ile | Ile | Asn | Val | Leu | Cys | Ser | Tyr | Leu | Gly | Leu | Val | |
| | 335 | | | | | 340 | | | | | 345 | | | | | |
| GAA | GTA | TAT | GAT | CCA | AGA | TTT | ATT | ATT | ATC | AGA | AGA | AAG | ATT | CTG | GAT | 3144 |
| Glu | Val | Tyr | Asp | Pro | Arg | Phe | Ile | Ile | Ile | Arg | Arg | Lys | Ile | Leu | Asp | |
| 350 | | | | | 355 | | | | | 360 | | | | | 365 | |
| CAT | GCT | AAT | TTA | CAA | TCT | CAT | TTG | CAA | CAA | CAA | GGT | CAA | ATG | ACA | TCT | 3192 |
| His | Ala | Asn | Leu | Gln | Ser | His | Leu | Gln | Gln | Gln | Gly | Gln | Met | Thr | Ser | |
| | | | | 370 | | | | | 375 | | | | | 380 | | |
| GCT | CAT | CCT | TTG | CAG | CCA | AAC | TCC | ACT | GGC | GGC | TCC | ATG | AAT | AGG | TCA | 3240 |
| Ala | His | Pro | Leu | Gln | Pro | Asn | Ser | Thr | Gly | Gly | Ser | Met | Asn | Arg | Ser | |
| | | | 385 | | | | | 390 | | | | | 395 | | | |
| CAA | TCT | TAT | ACA | AGT | TTG | TTA | CAG | GCC | CAT | GCA | GCA | GCT | GCA | GCG | AAT | 3288 |
| Gln | Ser | Tyr | Thr | Ser | Leu | Leu | Gln | Ala | His | Ala | Ala | Ala | Ala | Ala | Asn | |
| | | 400 | | | | | 405 | | | | | 410 | | | | |
| AGT | ATT | AGC | AAT | CAG | GCC | GTT | AAC | AAT | TCT | TCC | AAC | AGC | AAT | ACT | ATT | 3336 |
| Ser | Ile | Ser | Asn | Gln | Ala | Val | Asn | Asn | Ser | Ser | Asn | Ser | Asn | Thr | Ile | |
| | 415 | | | | | 420 | | | | | 425 | | | | | |
| AAC | AGT | AAT | AAC | GGT | AAC | GGT | AAC | AAT | GTC | ATC | ATT | AAT | AAC | AAT | AGC | 3384 |
| Asn | Ser | Asn | Asn | Gly | Asn | Gly | Asn | Asn | Val | Ile | Ile | Asn | Asn | Asn | Ser | |
| 430 | | | | | 435 | | | | | 440 | | | | | 445 | |
| GCC | AGC | TCA | ACA | CCA | AAA | ATT | TCT | TCA | CAG | GGA | CAA | TTC | TCC | ATG | CAA | 3432 |
| Ala | Ser | Ser | Thr | Pro | Lys | Ile | Ser | Ser | Gln | Gly | Gln | Phe | Ser | Met | Gln | |
| | | | | 450 | | | | | 455 | | | | | 460 | | |
| CCA | ACA | CTA | ACC | TCA | CCT | AAA | ATG | AAC | ATA | CAC | CAT | AGT | TCT | CAA | TAC | 3480 |
| Pro | Thr | Leu | Thr | Ser | Pro | Lys | Met | Asn | Ile | His | His | Ser | Ser | Gln | Tyr | |
| | | | 465 | | | | | 470 | | | | | 475 | | | |
| AAT | TCC | GCA | GAC | CAA | CCG | CAA | CAA | CCT | CAA | CCA | CAA | ACA | CAG | CAA | AAT | 3528 |
| Asn | Ser | Ala | Asp | Gln | Pro | Gln | Gln | Pro | Gln | Pro | Gln | Thr | Gln | Gln | Asn | |
| | | 480 | | | | | 485 | | | | | 490 | | | | |
| GTT | CAG | TCA | GCT | GCG | CAA | CAA | CAA | CAA | TCT | TTT | TTA | AGA | CAA | CAA | GCT | 3576 |
| Val | Gln | Ser | Ala | Ala | Gln | Gln | Gln | Gln | Ser | Phe | Leu | Arg | Gln | Gln | Ala | |
| | 495 | | | | | 500 | | | | | 505 | | | | | |

| | | | | | | | | | | | | | | | | |
|---|---|---|---|---|---|---|---|---|---|---|---|---|---|---|---|---|
| ACT | TTA | ACA | CCA | TCC | TCA | AGA | ATT | CCA | TCC | GGT | TAT | TCT | GCC | AAC | CAT | 3624 |
| Thr | Leu | Thr | Pro | Ser | Ser | Arg | Ile | Pro | Ser | Gly | Tyr | Ser | Ala | Asn | His | |
| 510 | | | | 515 | | | | | 520 | | | | | 525 | | |
| TAT | CAA | ATC | AAT | TCC | GTT | AAT | CCC | TTA | CTG | AGA | AAT | TCT | CAA | ATT | TCA | 3672 |
| Tyr | Gln | Ile | Asn | Ser | Val | Asn | Pro | Leu | Leu | Arg | Asn | Ser | Gln | Ile | Ser | |
| | | | | 530 | | | | | 535 | | | | | 540 | | |
| CCT | CCA | AAT | TCA | CAA | ATC | CCA | ATC | AAC | AGC | CAA | ACC | CTA | TCC | CAA | GCG | 3720 |
| Pro | Pro | Asn | Ser | Gln | Ile | Pro | Ile | Asn | Ser | Gln | Thr | Leu | Ser | Gln | Ala | |
| | | | 545 | | | | | 550 | | | | | 555 | | | |
| CAA | CCA | CCA | GCA | CAG | TCC | CAA | ACT | CAA | CAA | CGG | GTA | CCA | GTG | GCA | TAC | 3768 |
| Gln | Pro | Pro | Ala | Gln | Ser | Gln | Thr | Gln | Gln | Arg | Val | Pro | Val | Ala | Tyr | |
| | | 560 | | | | | 565 | | | | | 570 | | | | |
| CAA | AAT | GCT | TCA | TTG | TCT | TCC | CAG | CAG | TTG | TAC | AAC | CTT | AAC | GGC | CCA | 3816 |
| Gln | Asn | Ala | Ser | Leu | Ser | Ser | Gln | Gln | Leu | Tyr | Asn | Leu | Asn | Gly | Pro | |
| | 575 | | | | | 580 | | | | | 585 | | | | | |
| TCT | TCA | GCA | AAC | TCA | CAG | TCC | CAA | CTG | CTT | CCA | CAG | CAC | ACA | AAT | GGC | 3864 |
| Ser | Ser | Ala | Asn | Ser | Gln | Ser | Gln | Leu | Leu | Pro | Gln | His | Thr | Asn | Gly | |
| 590 | | | | | 595 | | | | | 600 | | | | | 605 | |
| TCA | GTA | CAT | TCT | AAT | TTC | TCA | TAT | CAG | TCT | TAT | CAC | GAT | GAG | TCC | ATG | 3912 |
| Ser | Val | His | Ser | Asn | Phe | Ser | Tyr | Gln | Ser | Tyr | His | Asp | Glu | Ser | Met | |
| | | | | 610 | | | | | 615 | | | | | 620 | | |
| TTG | TCC | GCA | CAC | AAT | TTG | AAT | AGT | GCC | GAC | TTG | ATC | TAT | AAA | TCT | TTG | 3960 |
| Leu | Ser | Ala | His | Asn | Leu | Asn | Ser | Ala | Asp | Leu | Ile | Tyr | Lys | Ser | Leu | |
| | | | 625 | | | | | 630 | | | | | 635 | | | |
| AGT | CAC | TCT | GGA | CTA | GAT | GAT | GGC | TTG | GAA | CAG | GGC | TTG | AAT | CGT | TCT | 4008 |
| Ser | His | Ser | Gly | Leu | Asp | Asp | Gly | Leu | Glu | Gln | Gly | Leu | Asn | Arg | Ser | |
| | | 640 | | | | | 645 | | | | | 650 | | | | |
| TTA | AGC | GGA | CTG | GAT | TTA | CAA | AAC | CAA | AAC | AAG | AAG | AAT | CTA | TGG | | 4053 |
| Leu | Ser | Gly | Leu | Asp | Leu | Gln | Asn | Gln | Asn | Lys | Lys | Asn | Leu | Trp | | |
| | 655 | | | | | 660 | | | | | 665 | | | | | |

```
TAATATATAC TTCCATTATT CTATGATTAT AGAGTTTGTT TGGTATTTGT ATATCGCACG    4113
ATACAAGTAA TGAGGGGTGC TTACACAAGA TAAAGATAA  AAAAATATAT ATATATAATA    4173
AAAACCATCA AAAACACCAT TGAAAAAAAA TATAAAAAAA AAAAAAAATA ACCGAATATG    4233
AATATGAAAT TAATGATCAT GATGAAGTTA ATTTTTACTG AGAAACGTCA CCTAATGTCG    4293
ATGAAACGAT GATAATGAAT GAATGATGAG GCTACTTTAA GTAACGCAAT GTAATCAAGC    4353
CAAAATTATC CCTCTTTTTT TTTTTTCCCT CTTTTGAGAT TTTATTTTTA ACCTACTACT    4413
TACTTTTTTT TTTTGAACGT TCTTTTCCCA CATACTTTTA TATATGGTAT TTATATGTAC    4473
GATGTTTAAT CACAGAGATG TTTCTACCTT ACTCGATATT GTTTTGCAT TAATTGATAT    4533
CTTGCTCACT GCATCATTGG CGGTATTTGT AGTATATAGA AAGTCGGGTA ACAATAATTT    4593
ATTGACATTT CTTTGTTTAC AATGATCAGA GAAGAGCAGA AAGTTTCATA GTCAAACGTT    4653
CAGGCCAATT GAACAAGAAA TTATTCGTTT TTTTAGTCGT TGAGTGTTCA ACTGACATGC    4713
TATTTTGGTG GTTCTTGATT AATTGGGGC TTCATTGTTT GAAATAAAGA GTCGGGAAAA    4773
TAGCACAGAA ACAAAGCATA TTAAAAGAGG CAAAAGAAGA AAGAACGAAT ATAAAAGGTA    4833
AAAAAGGAAA AGCATTGCTA TTCTTTTCTC ATAGGTGTTA TTCATACCGC CCTCTCTCTT    4893
CTTCCTTCTT CATTAATTAG TCTCCGTATA ATTTGCAGAT AATGTCATTA ACAGCAAACG    4953
ACGAATCGCC AAAACCCAAA AAAAATGCAT TATTGAAAAA CTTAGAGATC GATGATCTGA    5013
TACATTCTCA ATTTGTCAGA AGCGATACAA ATGGACATAG AACTACAAGA CGACTATTCA    5073
ACTCCGATGC CAGTATATCA CATCGAATAA GAGGAAGTGT TCGGTCTGAT AAAGGCCTTA    5133
ATAAATAAA  AAAAGGGTTG ATTTCCCAGC AGTCCAAACT TGCGTCAGAA AATTCTTCTC    5193
AAAATATCGT TAATAGGGAC AATAAGATGG GAGCAGTAAG TTTCCCCATT ATTGAACCTA    5253
```

| | | | | | |
|---|---|---|---|---|---|
|ATATTGAAGT|CAGCGAGGAG|TTGAAGGTTA|GAATTAAGTA|TGATTCTATC|AAATTTTTCA|5313|
|ATTTTGAAAG|ACTAATATCT|AAATCTTCAG|TCATAGCACC|TTTAGTTAAC|AAAAATATAA|5373|
|CATCATCCGG|TCCTCTAATC|GGGTTTCAAA|GAAGAGTTAA|CAGGTTAAAG|CAAACATGGG|5433|
|ATCTAGCAAC|CGAAAACATG|GAGTACCCAT|ATTCTTCTGA|TAATACGCCA|TTCAGGGATA|5493|
|ACGATTCTTG|GCAATGGTAC|GTACCATACG|GCGGAACAAT|AAAAAAAATG|AAAGATTTCA|5553|
|GTACAAAAAG|AACTTTACCC|ACCTGGGAAG|ATAAATAAA|GTTTCTTACA|TTTTAGAAA|5613|
|ACTCTAAGTC|TGCAACGTAC|ATTAATGGTA|ACGTATCACT|TTGCAATCAT|AATGAAACCG|5673|
|ATCAAGAAAA|CGAAGATAGG|AAAAAAGGA|AAGGGAAAGT|ACCAAGAATC|AAAAATAAAG|5733|
|TGTGGTTTTC|CCAGATAGAA|TACATTGTTC|TTCGAAATTA|TGAAATTAAA|CCTTGGTATA|5793|
|CATCTCCTTT|TCCGGAACAC|ATCAACCAAA|ATAAATGGT|TTTTATATGT|GAGTTCTGCC|5853|
|TAAAATATAT|GACTTCTCGA|TATACTTTTT|ATAGACACCA|ACTAAGTGT|CTAACTTTTA|5913|
|AGCCCCCCGG|AAATGAAATT|TATCGCGACG|GTAAGCTGTC|TGTTTGGGAA|ATTGATGGGC|5973|
|GGGAGAATGT|CTTGTATTGT|CAAAATCTTT|GCCTGTTGGC|AAAATGTTTT|ATCAATTCTA|6033|
|AGACTTTGTA|TTACGATGTT|GAACCGTTTA|TATTCTATAT|TCTAACGGAG|AGAGGATA|6093|
|CAGAGAACCA|TCCCTATCAA|AACGCAGCCA|AATTCCATTT|CGTAGGCTAT|TTCTCCAAGG|6153|
|AAAAATTCAA|CTCCAATGAC|TATAACCTAA|GTTGTATTTT|AACTCTACCC|ATATACCAGA|6213|
|GGAAAGGATA|TGGTCAGTTT|TTGATGGAAT|TTTCATATTT|ATTATCCAGA|AAGGAGTCAA|6273|
|AATTTGGAAC|TCCTGAAAAA|CCATTGTCGG|ATTTAGGATT|ATTGACTTAC|AGAACGTTTT|6333|
|GGAAGATAAA|ATGTGCTGAA|GTGCTATTAA|AATTAAGAGA|CAGTGCTAGA|CGTCGATCAA|6393|
|ATAATAAAAA|TGAAGATACT|TTTCAGCAGG|TTAGCCTAAA|CGATATCGCT|AAACTAACAG|6453|
|GAATGATACC|AACAGACGTT|GTGTTTGGAT|TGGAACAACT|TCAAGTTTTG|TATCGCCATA|6513|
|AAACACGCTC|ATTATCCAGT|TTGGATGATT|TCAACTATAT|TATTAAAATC|GATTCTTGGA|6573|
|ACAGGATTGA|AAATATTTAC|AAAACTTGGA|GCTCAAAAAA|CTATCCTCGC|GTCAAATATG|6633|
|ACAAACTATT|GTGGGAACCT|ATTATATTAG|GGCCGTCATT|TGGTATAAAT|GGGATGATGA|6693|
|ACTTAGAACC|CACCGCATTA|GCGGACGAAG|CTCTTACAAA|TGAAACTATG|GCTCCGGTAA|6753|
|TTTCGAATAA|CACACATATA|GAAAACTATA|ACAACAGTAG|AGCACATAAT|AAACGCAGAA|6813|
|GAAGAAGAAG|AAGAAGTAGT|GAGCACAAAA|CATCCAAGCT|T| |6854|

( 2 ) INFORMATION FOR SEQ ID NO:5:

( i ) SEQUENCE CHARACTERISTICS:
        ( A ) LENGTH: 668 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Glu Thr Ser Ser Phe Glu Asn Ala Pro Pro Ala Ala Ile Asn Asp
 1               5                  10                  15

Ala Gln Asp Asn Asn Ile Asn Thr Glu Thr Asn Asp Gln Glu Thr Asn
            20                  25                  30

Gln Gln Ser Ile Glu Thr Arg Asp Ala Ile Asp Lys Glu Asn Gly Val
        35                  40                  45

Gln Thr Glu Thr Gly Glu Asn Ser Ala Lys Asn Ala Glu Gln Asn Val
    50                  55                  60
```

-continued

| | | | | | | | | | | | | | | | |
|---|---|---|---|---|---|---|---|---|---|---|---|---|---|---|---|
| Ser | Ser | Thr | Asn | Leu | Asn | Asn | Ala | Pro | Thr | Asn | Gly | Ala | Leu | Asp | Asp |
| 65 | | | | 70 | | | | | 75 | | | | | | 80 |
| Asp | Val | Ile | Pro | Asn | Ala | Ile | Val | Ile | Lys | Asn | Ile | Pro | Phe | Ala | Ile |
| | | | | 85 | | | | | 90 | | | | | 95 | |
| Lys | Lys | Glu | Gln | Leu | Leu | Asp | Ile | Ile | Glu | Glu | Met | Asp | Leu | Pro | Leu |
| | | | 100 | | | | | 105 | | | | | 110 | | |
| Pro | Tyr | Ala | Phe | Asn | Tyr | His | Phe | Asp | Asn | Gly | Ile | Phe | Arg | Gly | Leu |
| | | | 115 | | | | 120 | | | | | 125 | | | |
| Ala | Phe | Ala | Asn | Phe | Thr | Thr | Pro | Glu | Glu | Thr | Thr | Gln | Val | Ile | Thr |
| | | 130 | | | | 135 | | | | | 140 | | | | |
| Ser | Leu | Asn | Gly | Lys | Glu | Ile | Ser | Gly | Arg | Lys | Leu | Lys | Val | Glu | Tyr |
| 145 | | | | | 150 | | | | | 155 | | | | | 160 |
| Lys | Lys | Met | Leu | Pro | Gln | Ala | Glu | Arg | Glu | Arg | Ile | Glu | Arg | Glu | Lys |
| | | | | 165 | | | | | 170 | | | | | 175 | |
| Arg | Glu | Lys | Arg | Gly | Gln | Leu | Glu | Glu | Gln | His | Arg | Ser | Ser | Ser | Asn |
| | | | 180 | | | | | 185 | | | | | 190 | | |
| Leu | Ser | Leu | Asp | Ser | Leu | Ser | Lys | Met | Ser | Gly | Ser | Gly | Asn | Asn | Asn |
| | | 195 | | | | | 200 | | | | | 205 | | | |
| Thr | Ser | Asn | Asn | Gln | Leu | Phe | Ser | Thr | Leu | Met | Asn | Gly | Ile | Asn | Ala |
| | 210 | | | | | 215 | | | | | 220 | | | | |
| Asn | Ser | Met | Met | Asn | Ser | Pro | Met | Asn | Asn | Thr | Ile | Asn | Asn | Asn | Ser |
| 225 | | | | | 230 | | | | | 235 | | | | | 240 |
| Ser | Asn | Asn | Asn | Asn | Ser | Gly | Asn | Ile | Ile | Leu | Asn | Gln | Pro | Ser | Leu |
| | | | | 245 | | | | | 250 | | | | | 255 | |
| Ser | Ala | Gln | His | Thr | Ser | Ser | Ser | Leu | Tyr | Gln | Thr | Asn | Val | Asn | Asn |
| | | | 260 | | | | | 265 | | | | | 270 | | |
| Gln | Ala | Gln | Met | Ser | Thr | Glu | Arg | Phe | Tyr | Ala | Pro | Leu | Pro | Ser | Thr |
| | | 275 | | | | | 280 | | | | | 285 | | | |
| Ser | Thr | Leu | Pro | Leu | Pro | Pro | Gln | Gln | Leu | Asp | Phe | Asn | Asp | Pro | Asp |
| | 290 | | | | | 295 | | | | | 300 | | | | |
| Thr | Leu | Glu | Ile | Tyr | Ser | Gln | Leu | Leu | Leu | Phe | Lys | Asp | Arg | Glu | Lys |
| 305 | | | | | 310 | | | | | 315 | | | | | 320 |
| Tyr | Tyr | Tyr | Glu | Leu | Ala | Tyr | Pro | Met | Gly | Ile | Ser | Ala | Ser | His | Lys |
| | | | | 325 | | | | | 330 | | | | | 335 | |
| Arg | Ile | Ile | Asn | Val | Leu | Cys | Ser | Tyr | Leu | Gly | Leu | Val | Glu | Val | Tyr |
| | | | 340 | | | | | 345 | | | | | 350 | | |
| Asp | Pro | Arg | Phe | Ile | Ile | Ile | Arg | Arg | Lys | Ile | Leu | Asp | His | Ala | Asn |
| | | 355 | | | | | 360 | | | | | 365 | | | |
| Leu | Gln | Ser | His | Leu | Gln | Gln | Gln | Gly | Gln | Met | Thr | Ser | Ala | His | Pro |
| | 370 | | | | | 375 | | | | | 380 | | | | |
| Leu | Gln | Pro | Asn | Ser | Thr | Gly | Gly | Ser | Met | Asn | Arg | Ser | Gln | Ser | Tyr |
| 385 | | | | | 390 | | | | | 395 | | | | | 400 |
| Thr | Ser | Leu | Leu | Gln | Ala | His | Ala | Ala | Ala | Ala | Ala | Asn | Ser | Ile | Ser |
| | | | | 405 | | | | | 410 | | | | | 415 | |
| Asn | Gln | Ala | Val | Asn | Asn | Ser | Ser | Asn | Ser | Asn | Thr | Ile | Asn | Ser | Asn |
| | | | 420 | | | | | 425 | | | | | 430 | | |
| Asn | Gly | Asn | Gly | Asn | Asn | Val | Ile | Ile | Asn | Asn | Asn | Ser | Ala | Ser | Ser |
| | | 435 | | | | | 440 | | | | | 445 | | | |
| Thr | Pro | Lys | Ile | Ser | Ser | Gln | Gly | Gln | Phe | Ser | Met | Gln | Pro | Thr | Leu |
| | 450 | | | | | 455 | | | | | 460 | | | | |
| Thr | Ser | Pro | Lys | Met | Asn | Ile | His | His | Ser | Ser | Gln | Tyr | Asn | Ser | Ala |
| 465 | | | | | 470 | | | | | 475 | | | | | 480 |
| Asp | Gln | Pro | Gln | Gln | Pro | Gln | Pro | Gln | Thr | Gln | Gln | Asn | Val | Gln | Ser |
| | | | | 485 | | | | | 490 | | | | | 495 | |

| Ala | Ala | Gln | Gln<br>500 | Gln | Gln | Ser | Phe | Leu<br>505 | Arg | Gln | Gln | Ala<br>510 | Thr | Leu | Thr |
|---|---|---|---|---|---|---|---|---|---|---|---|---|---|---|---|
| Pro | Ser | Ser<br>515 | Arg | Ile | Pro | Ser | Gly<br>520 | Tyr | Ser | Ala | Asn | His<br>525 | Tyr | Gln | Ile |
| Asn | Ser<br>530 | Val | Asn | Pro | Leu | Leu<br>535 | Arg | Asn | Ser | Gln | Ile<br>540 | Ser | Pro | Pro | Asn |
| Ser<br>545 | Gln | Ile | Pro | Ile | Asn<br>550 | Ser | Gln | Thr | Leu | Ser<br>555 | Gln | Ala | Gln | Pro | Pro<br>560 |
| Ala | Gln | Ser | Gln | Thr<br>565 | Gln | Gln | Arg | Val | Pro<br>570 | Val | Ala | Tyr | Gln | Asn<br>575 | Ala |
| Ser | Leu | Ser | Ser<br>580 | Gln | Gln | Leu | Tyr | Asn<br>585 | Leu | Asn | Gly | Pro | Ser<br>590 | Ser | Ala |
| Asn | Ser | Gln<br>595 | Ser | Gln | Leu | Leu | Pro<br>600 | Gln | His | Thr | Asn | Gly<br>605 | Ser | Val | His |
| Ser | Asn<br>610 | Phe | Ser | Tyr | Gln | Ser<br>615 | Tyr | His | Asp | Glu | Ser<br>620 | Met | Leu | Ser | Ala |
| His<br>625 | Asn | Leu | Asn | Ser | Ala<br>630 | Asp | Leu | Ile | Tyr | Lys<br>635 | Ser | Leu | Ser | His | Ser<br>640 |
| Gly | Leu | Asp | Asp | Gly<br>645 | Leu | Glu | Gln | Gly | Leu<br>650 | Asn | Arg | Ser | Leu | Ser<br>655 | Gly |
| Leu | Asp | Leu | Gln<br>660 | Asn | Gln | Asn | Lys | Lys<br>665 | Asn | Leu | Trp | | | | |

( 2 ) INFORMATION FOR SEQ ID NO:6:

( i ) SEQUENCE CHARACTERISTICS:
        ( A ) LENGTH: 2814 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..696

( x i ) SEQUENCE DESCRIPTION: SEQ ID NO:6:

| GAA | TTC | CAA | TAC | ACC | AAA | CAG | CTG | CAT | TTC | CCT | GTG | GGG | CCC | AAA | TCC | 48 |
|---|---|---|---|---|---|---|---|---|---|---|---|---|---|---|---|---|
| Glu<br>1 | Phe | Gln | Tyr | Thr<br>5 | Lys | Gln | Leu | His | Phe<br>10 | Pro | Val | Gly | Pro | Lys<br>15 | Ser | |
| ACA | AAC | TGT | GAG | GTA | GCG | GAA | ATT | CTT | TTA | CAC | TGC | GAC | TGG | GAA | AGG | 96 |
| Thr | Asn | Cys | Glu<br>20 | Val | Ala | Glu | Ile | Leu<br>25 | Leu | His | Cys | Asp | Trp<br>30 | Glu | Arg | |
| TAC | ATA | AAT | GTT | TTA | AGT | ATA | ACA | AGA | ACA | CCA | AAT | GTT | CCT | AGT | GGT | 144 |
| Tyr | Ile | Asn<br>35 | Val | Leu | Ser | Ile | Thr<br>40 | Arg | Thr | Pro | Asn | Val<br>45 | Pro | Ser | Gly | |
| ACC | AGT | TTC | AGC | ACC | AGA | ACG | AGG | TAC | ATG | TTC | CGA | TGG | GAT | GAC | CAG | 192 |
| Thr | Ser<br>50 | Phe | Ser | Thr | Arg | Thr<br>55 | Arg | Tyr | Met | Phe | Arg<br>60 | Trp | Asp | Asp | Gln | |
| GGG | CAA | GGT | TGC | ATA | TTA | AAA | ATA | AGT | TTT | TGG | GTG | GAC | TGG | AAC | GCA | 240 |
| Gly<br>65 | Gln | Gly | Cys | Ile | Leu<br>70 | Lys | Ile | Ser | Phe | Trp<br>75 | Val | Asp | Trp | Asn | Ala<br>80 | |
| TCC | AGT | TGG | ATC | AAG | CCA | ATG | GTA | GAG | AGC | AAT | TGT | AAA | AAT | GGA | CAA | 288 |
| Ser | Ser | Trp | Ile | Lys<br>85 | Pro | Met | Val | Glu | Ser<br>90 | Asn | Cys | Lys | Asn | Gly<br>95 | Gln | |
| ATT | AGC | GCC | ACT | AAG | GAC | TTG | GTA | AAG | TTA | GTC | GAA | GAA | TTT | GTA | GAG | 336 |
| Ile | Ser | Ala | Thr<br>100 | Lys | Asp | Leu | Val | Lys<br>105 | Leu | Val | Glu | Glu | Phe<br>110 | Val | Glu | |

-continued

| | | | | | | | | | | | | | | | | |
|---|---|---|---|---|---|---|---|---|---|---|---|---|---|---|---|---|
| AAA | TAC | GTG | GAA | TTG | AGC | AAA | GAA | AAA | GCA | GAT | ACA | CTC | AAG | CCG | TTG | 384 |
| Lys | Tyr | Val | Glu | Leu | Ser | Lys | Glu | Lys | Ala | Asp | Thr | Leu | Lys | Pro | Leu | |
| | | 115 | | | | | 120 | | | | | 125 | | | | |
| CCC | AGT | GTT | ACA | TCT | TTT | GGA | TCA | CCT | AGG | AAA | GTG | GCA | GCA | CCG | GAG | 432 |
| Pro | Ser | Val | Thr | Ser | Phe | Gly | Ser | Pro | Arg | Lys | Val | Ala | Ala | Pro | Glu | |
| | 130 | | | | | 135 | | | | | 140 | | | | | |
| CTG | TCG | ATG | GTA | CAG | CCG | GAG | TCG | AAA | CCA | GAA | GCT | GAG | GCG | GAA | ATC | 480 |
| Leu | Ser | Met | Val | Gln | Pro | Glu | Ser | Lys | Pro | Glu | Ala | Glu | Ala | Glu | Ile | |
| 145 | | | | | 150 | | | | | 155 | | | | | 160 | |
| TCA | GAA | ATA | GGC | AGC | GAC | AGA | TGG | AGG | TTT | AAC | TGG | GTG | AAC | ATA | ATA | 528 |
| Ser | Glu | Ile | Gly | Ser | Asp | Arg | Trp | Arg | Phe | Asn | Trp | Val | Asn | Ile | Ile | |
| | | | | 165 | | | | | 170 | | | | | 175 | | |
| ATC | TTG | GTG | CTC | TTG | GTG | TTA | AAT | CTG | CTG | TAT | TTA | ATG | AAG | TTG | AAC | 576 |
| Ile | Leu | Val | Leu | Leu | Val | Leu | Asn | Leu | Leu | Tyr | Leu | Met | Lys | Leu | Asn | |
| | | | | 180 | | | | | 185 | | | | | 190 | | |
| AAG | AAG | ATG | GAT | AAG | CTG | ACG | AAC | CTC | ATG | ACC | CAC | AAG | GAC | GAA | GTT | 624 |
| Lys | Lys | Met | Asp | Lys | Leu | Thr | Asn | Leu | Met | Thr | His | Lys | Asp | Glu | Val | |
| | | 195 | | | | | 200 | | | | | 205 | | | | |
| GTA | GCG | CAC | GCG | ACT | CTA | TTG | GAC | ATA | CCA | GCC | CAA | GTA | CAA | TGG | TCA | 672 |
| Val | Ala | His | Ala | Thr | Leu | Leu | Asp | Ile | Pro | Ala | Gln | Val | Gln | Trp | Ser | |
| | 210 | | | | | 215 | | | | | 220 | | | | | |
| AGA | CCA | AGA | AGG | GGA | GAC | GTG | TTG | TAACAGAGTA | ATCATGTAAT | ATTGTATGTA | | | | | | 726 |
| Arg | Pro | Arg | Arg | Gly | Asp | Val | Leu | | | | | | | | | |
| 225 | | | | | 230 | | | | | | | | | | | |

```
AGGTTATGTA TGTTCGTATG GTATGGAAAA AAAAAAAAAA AAAGGATGCT ATGTGGAGAA    786
TGTAAGGCGT GGTAGCTCCG GATAATTCAG TCTGTAGGCT TCATCACGGG CAGTGGCCTG    846
ACTCTGAGAG CTTGCTCCGG TATTAAGTTG TGCGTTTGAA ATTTTCTGGA AAAAAGAAAT    906
TGATTGGTTG AAGCTATACT CGTCGAAAGA TTTCTTCGGC AGTGGTTGTT GCTCCACCTG    966
CACGGGAGTT GTGTTTGCGT TTATGTTCGG CTTGGCTATA TTATTAGCGA GTGATGTTTG   1026
CAATTTGCTG TATTGAGAAT CAATTTGGGT GCGTAAGCTT TCAATAATTT TGCAGACCGC   1086
AGGCACTTCC AACTTTATGA GTTGCAGGTA TTCTCTTTTA TGAATATACG ATGACGACGA   1146
TGACGACGAC GCATCCATGC GCAAAAGCTC AGGGTGTCTA GATAGTTTGT TAGTCAATAA   1206
ATCCACATAT CTAAAATAAT AAATAAACGA CAGCGACAAG TCGTTGGCCT GGAACGCACA   1266
CTGTGCCTTT TCCAATATGC CGATGCATGT TTTCAGGTAA ATTCTCAATG GTATCGCCGG   1326
ATTGAAGCGA TAATCCTTAG CGTCCTGAAC CAATTGCTTA CTAGACTTCA TGACCTACCG   1386
GGGCCAGATA AGATGCGGA AGGAAGAGAA AAAATGTATA GTGGTTGGTG AACCGCAACA   1446
ATAATTCGTG CCAACACTTT AATCGAAGCA AAAATTGTCT TGTATGTTAT TAATATTATC   1506
TATCTAACCA TTGATTTACG TATAAAACTG TCGATGCTCA TCGCCTAGCA ATGAAAAAAT   1566
TTTTTCTTTT TTTTTTCATT ATTTCTCTTT GTTGCGTACT TTTTTTCATT GCGTTTCGCG   1626
GCAAAAGCGA TTCGAGTTGA CTGGAAGTGT GTTATACTAT AAAAAGTGTA TATGCCTATT   1686
TTTGGTTCTG ATCTTTACTT TACTGTTAAG TACTGGCTGA GGCAGTAGAC TCTGCCTCTG   1746
TTACGGCAGC GGTATTCGCC TCGGCATCAG CAGCCGCCCA CGGTAGAGTA GGTTCTGTTG   1806
TTTTGACGTT TGCCAAGGTA CTGTCCAAAT GCTCCTTCAG CAAGGCCTCA TTACTTTCCT   1866
TCTCCGGACC CACCGATTGC GTGATCTCCT GTACACGGTT CAAGAACTTG TTCAAATTGT   1926
AGCCCGCAGC AGCATCAGAG ACTTCTTGTG TGTAAGGGAC ACCCCTCAAC TCCTTGACTC   1986
TTCTTTTGTG CACTTTGCCC TTTAAATGCG TTTTTAACGC TATAGCAGTC TCCATGTATT   2046
TGGCACAGTG TATGCAATAG TGCTGACCAA GGCCCGGTTT GGTTTCATCC AATGGCTGGT   2106
TCAGAAGCTT CTGTACTGAT TCCTTGGTGG ACAAATCGTT ATAGATCAGG TCCAAGTCTC   2166
```

```
GTGTTCTTCT   TTTAGTCTTG   TATCTCTTCA   CCGAATATCT   ACCCATGATG   CGCTATTGTT    2226

TTATCTTCAC   TTGTCTGTGT   GTTTAACTGC   CTTTCAATTC   ACCTCATCTC   ATCTCCCGCT    2286

ACTTTCCATA   TATAAAAGCA   AAATTAATTT   GCTTTTTCCC   CTGTCAGTAT   AAAAAAATTT    2346

TCCGCAGGAT   ATAGAAAAAA   AGAAATGAA    ATTATAGTAG   CGGTTATTTC   CGTGGGGTGC    2406

TTTTTTACAC   CTGTACATCT   TTTCCCTCCG   TACATTTTTT   TTATTTTTTT   TTTGGGTTTT    2466

TTTTTTTCGA   TATTTTTCCC   TCCGAAACTA   GTTAGCACAA   TAATGCTGAC   TAAGGAAACT    2526

TTTCATCTCA   GAATTGATGG   TCAGTTTGGT   TTCTCTAGAG   AATAGTTTAT   AAAAAGATGT    2586

TGATGTGGAG   CAACCATTTA   TACATCCTTT   CCGCAAGTGC   TTTTGGAGTG   GGACTTTCAA    2646

ACTTTAAAGT   ACAGTATATC   AAATAACTAA   TTCAAGATGG   CTAGAAGACC   AGCTAGATGT    2706

TACAGATACC   AAAAGAACAA   GCCTTACCCA   AAGTCTAGAT   ACAACAGAGC   TGTTCCAGAC    2766

TCCAAGATCA   GAATCTACGA   TTTGGGTAAG   AAGAAGGCTA   CCGTCGAT                   2814
```

( 2 ) INFORMATION FOR SEQ ID NO:7:

( i ) SEQUENCE CHARACTERISTICS:
        ( A ) LENGTH: 232 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Glu  Phe  Gln  Tyr  Thr  Lys  Gln  Leu  His  Phe  Pro  Val  Gly  Pro  Lys  Ser
  1              5                        10                       15

Thr  Asn  Cys  Glu  Val  Ala  Glu  Ile  Leu  Leu  His  Cys  Asp  Trp  Glu  Arg
                 20                       25                       30

Tyr  Ile  Asn  Val  Leu  Ser  Ile  Thr  Arg  Thr  Pro  Asn  Val  Pro  Ser  Gly
             35                       40                       45

Thr  Ser  Phe  Ser  Thr  Arg  Thr  Arg  Tyr  Met  Phe  Arg  Trp  Asp  Asp  Gln
        50                       55                       60

Gly  Gln  Gly  Cys  Ile  Leu  Lys  Ile  Ser  Phe  Trp  Val  Asp  Trp  Asn  Ala
 65                       70                       75                       80

Ser  Ser  Trp  Ile  Lys  Pro  Met  Val  Glu  Ser  Asn  Cys  Lys  Asn  Gly  Gln
                 85                       90                       95

Ile  Ser  Ala  Thr  Lys  Asp  Leu  Val  Lys  Val  Glu  Glu  Phe  Val  Glu
             100                      105                      110

Lys  Tyr  Val  Glu  Leu  Ser  Lys  Glu  Lys  Ala  Asp  Thr  Leu  Lys  Pro  Leu
             115                      120                      125

Pro  Ser  Val  Thr  Ser  Phe  Gly  Ser  Pro  Arg  Lys  Val  Ala  Ala  Pro  Glu
        130                      135                      140

Leu  Ser  Met  Val  Gln  Pro  Glu  Ser  Lys  Pro  Glu  Ala  Glu  Ala  Glu  Ile
145                      150                      155                     160

Ser  Glu  Ile  Gly  Ser  Asp  Arg  Trp  Arg  Phe  Asn  Trp  Val  Asn  Ile  Ile
                 165                      170                      175

Ile  Leu  Val  Leu  Leu  Val  Leu  Asn  Leu  Leu  Tyr  Leu  Met  Lys  Leu  Asn
             180                      185                      190

Lys  Lys  Met  Asp  Lys  Leu  Thr  Asn  Leu  Met  Thr  His  Lys  Asp  Glu  Val
             195                      200                      205

Val  Ala  His  Ala  Thr  Leu  Leu  Asp  Ile  Pro  Ala  Gln  Val  Gln  Trp  Ser
        210                      215                      220

Arg  Pro  Arg  Arg  Gly  Asp  Val  Leu
225                      230
```

( 2 ) INFORMATION FOR SEQ ID NO:8:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
ATGGACTTAA  GAGTAGGAAG  GAAATTTCGT  ATTGGCAGGA  AGATTGGGAG  TGGTTCCTTT     60
GGTGACATTT  ACCACGGCAC  GAACTTAATT  AGTGGTGAAG  AAGTAGCCAT  CAAGCTGGAA    120
TCGATCAGGT  CCAGACATCC  TCAATTGGAC  TATGAGTCCC  GCGTCTACAG  ATACTTAAGC    180
GGTGGTGTGG  GAATCCCGTT  CATCAGATGG  TTTGGCAGAG  AGGGTGAATA  TAATGCTATG    240
GTCATCGATC  TTCTAGGCCC  ATCTTTGGAA  GATTTATTCA  ACTACTGTCA  CAGAAGGTTC    300
TCCTTTAAGA  CGGTTATCAT  GCTGGCTTTG  CAAATGTTTT  GCCGTATTCA  GTATATACAT    360
GGAAGGTCGT  TCATTCATAG  AGATATCAAA  CCAGACAACT  TTTTAATGGG  GGTAGGACGC    420
CGTGGTAGCA  CCGTTCATGT  TATTGATTTC  GGTCTATCAA  AGAAATACCG  AGATTTCAAC    480
ACACATCGTC  ATATTCCTTA  CAGGGAGAAC  AAGTCCTTGA  CAGGTACAGC  TCGTTATGCA    540
AGTGTCAATA  CGCATCTTGG  AATAGAGCAA  AGTAGAAGAG  ATGACTTAGA  ATCACTAGGT    600
TATGTCTTGA  TCTATTTTTG  TAAGGGTTCT  TTGCCATGGC  AGGGTTTGAA  AGCAACCACC    660
AAGAAACAAA  AGTATGATCG  TATCATGGAA  AAGAAATTAA  ACGTTAGCGT  GGAAACTCTA    720
TGTTCAGGTT  TACCATTAGA  GTTTCAAGAA  TATATGGCTT  ACTGTAAGAA  TTTGAAATTC    780
GATGAGAAGC  CAGATTATTT  GTTCTTGGCA  AGGCTGTTTA  AAGATCTGAG  TATTAAACTA    840
GAGTATCACA  ACGACCACTT  GTTCGATTGG  ACAATGTTGC  GTTACACAAA  GGCGATGGTG    900
GAGAAGCAAA  GGGACCTCCT  CATCGAAAAA  GGTGATTTGA  ACGCAAATAG  CAATGCAGCA    960
AGTGCAAGTA  ACAGCACAGA  CAACAAGTCT  GAAACTTTCA  ACAAGATTAA  ACTGTTAGCC   1020
ATGAAGAAAT  TCCCCACCCA  TTTCCACTAT  TACAAGAATG  AAGACAAACA  TAATCCTTCA   1080
CCAGAAGAGA  TCAAACAACA  AACTATCTTG  AATAATAATG  CAGCCTCTTC  TTTACCAGAG   1140
GAATTATTGA  ACGCACTAGA  TAAAGGTATG  GAAAACTTGA  GACAACAGCA  GCCGCAGCAG   1200
CAGGTCCAAA  GTTCGCAGCC  ACAACCACAG  CCCCAACAGC  TACAGCAGCA  ACCAAATGGC   1260
CAAAGACCAA  ATTATTATCC  TGAACCGTTA  CTACAGCAGC  AACAAAGAGA  TTCTCAGGAG   1320
CAACAGCAGC  AAGTTCCGAT  GGCTACAACC  AGGGCTACTC  AGTATCCCCC  ACAAATAAAC   1380
AGCAATAATT  TTAATACTAA  TCAAGCATCT  GTACCTCCAC  AAATGAGATC  TAATCCACAA   1440
CAGCCGCCTC  AAGATAAACC  AGCTGGCCAG  TCAATTTGGT  TGTAA                    1485
```

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
CCTACTCTTA  GGCCCGGGTC  TTTTTAATGT  ATCC                                    34
```

( 2 ) INFORMATION FOR SEQ ID NO:10:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

GGAATCACTA CAGGGATG                                                                                    18

( 2 ) INFORMATION FOR SEQ ID NO:11:

( i ) SEQUENCE CHARACTERISTICS:
        ( A ) LENGTH: 543 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GATCTCTGAA TTGAAGAACC GTTCAAACAT TGGCGAGCCC TTAACCAAAT CTTCCAATGA     60

AAGTACTTAT AAAGACATTA AAGCCACCGG CAATGATGGT GATCCGAATT TGGCTCTAAT    120

GAGAGCGGAG AATCGAGTAT TAAATATAA ACTAGAGAAT TGTGAAAAAC TACTAGATAA     180

AGATGTGGTT GATTTGCAAG ATTCTGAGAT TATGGAAATT GTAGAAATGC TTCCCTTTGA    240

GGTCGGCACC CTTTTGGAAA CAAAGTTCCA AGGTTTGGAA TCACAAATAA GGCAATATAG    300

GAAATACACT CAAAAACTTG AAGACAAGAT CATGGCGCTA GAAAAAAGTG GTCATACTGC    360

AATGTCGCTA ACTGGGTGTG ACGGCACTGA AGTGATCGAA TTACAGAAGA TGCTCGAGAG    420

GAAGGATAAA ATGATTGAGG CCCTGCAGAG TGCCAAACGA CTGCGGGATA GGGCTTTGAA    480

ACCACTCATT AATACACAGC AATCACCGCA CCCTGTCGTG GATAACGATA AATGATTAGG    540

TGA                                                                  543

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CCTTCCTACT CTTAAGCCCG GGCCGCAGGA ATTCG                                                                  35

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

AGCAATATAG GATCCTTACA ACCAAATTGA                                                                        30

( 2 ) INFORMATION FOR SEQ ID NO:14:

( i ) SEQUENCE CHARACTERISTICS:
        ( A ) LENGTH: 34 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

```
CCTACTCTTA AGCCCGGGTC TTTTTAATGT ATCC                                        34
```

(2) INFORMATION FOR SEQ ID NO:15:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

```
GTCTCAAGTT TTGGGATCCT TAATCTAGTG CG                                          32
```

(2) INFORMATION FOR SEQ ID NO:16:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

```
CACCATCGCC CCCGGGTAAC GCAACATTGT CC                                          32
```

(2) INFORMATION FOR SEQ ID NO:17:

(i) SEQUENCE CHARACTERISTICS:
(A) LENGTH: 3628 base pairs
(B) TYPE: nucleic acid
(C) STRANDEDNESS: single
(D) TOPOLOGY: linear (ii) MOLECULE TYPE: protein (xi) SEQUENCE DESCRIPTION: SEQ ID NO:17:

```
GATCAGATGA TATAGCTTTT TGTGTGCCGT ACCTTTCCGC GATTCTGCCC GTATATCTTG           60
GTCCCTGAGC TATTTTCTGA GATTCTTTTT GTTGCTTTGC CAAATCATTG GCGTCATTCA          120
TGGTCATACC AAATCCCAAT TTGGCAAACT GGGTGTTAA  AGTATCTTGC TGTTCTTTTC          180
TAGTTGTGTC GAAGCTGTTT GAAGTGTCAT TTAAAAAATC ATTGAATTCA TCAGGCTGGG          240
TATTAATATC ATCTATACTG TTATTATTGT TGCCTTTACT GTTATTCATA AATTGGGAAT          300
CGTAATCATT TGTCTAATTT TGGTGCTAGA AGACGAATTA GTGAACTCGT CCTCCTTTTC          360
TTGTTGAGCC TCTTTTTTAA ATTGATCAAA CAAGTCTTCT GCCTGTGATT TGTCGACTTT          420
CTTTGCGGTT AGTCTAGTGG GCTTTCTTGA CGAAGACAAA ATTGAATGTT TCTTTTTATC          480
TTGCGAGTTT AATACCGGTT TCTTTCTGCA TGCCGTTAAG ATGGAACTTC TCGTTTTAGT          540
GACAGTGGTC TTGGGTGTGC TGCCTGTGGT GTTGTTTTTT GGGGCGAGAG AGCCTGTATT          600
TACATTGAGT TTAGAACTGG AATTGGAGCT TGGTTTTTGC CAATTAGAGA AAAAATCGTC          660
AACACTATTT TCTTTGGAAG TCGACCTGGA AGCGTCTGAA TCGGTGTCCA ACGGTGAGTC          720
CGAAGAATCT TGACCGTTCA AGACTAATTC TGATGGGTAT AACTCCATAT CCTTTTGAAC          780
CTTCTTGTCG AGATGTATCT TATATTTCTT AGCAACAGGG CTCGTATATT TTGTTTTCGC          840
```

```
GTCAACATTT  GCTGTATTTA  GTAGCTGTTT  CCCATTGTTC  TTTAAGAAAA  AATCACGAGC   900
CTTATGGTTC  CCACCCAACT  TAAACCTTCT  TAAATTGTTA  ATTGTCCATT  TATCTAATGT   960
AGAAGACTTT  ACAAAGGTGA  TATGAACACC  CATGTTTCTA  TGCACAGCAG  AGCATTGAAT  1020
ACACAGCATC  ACACCAAAAG  GTACCGAAGT  CCAGTAGGAT  TCTTGTTACC  ACAATCAAAA  1080
CAAACTCGAT  TTTCCATGTT  GCTACCTAGC  TTCTGAAAAA  CTTGTTGAGT  AGTCTGTTCC  1140
GTGGCAAATG  TTTCTCCTTC  ATCGTTACTC  ATTGTCGCTA  TGTGTATACT  AAATTGCTCA  1200
AGAAGACCGG  ATCAACAAGT  ACTTAACAAA  TACCCTTTCT  TTGCTATCGC  CTTGATCTCC  1260
TTTTATAAAA  TGCCAGCTAA  ATCGTGTTTA  CGAAGAATAG  TTGTTTTCTT  TTTTTTTTT   1320
TTTTTTCGAA  ACTTACCGT   GTCGTCGAAA  ATGACCAAAC  GATGTTACTT  TTCCTTTTGT  1380
GTCATAGATA  ATACCAATAT  TGAAAGTAAA  ATTTTAAACA  TTCTATAGGT  GAATTGAAAA  1440
GGGCAGCTTA  GAGAGTAACA  GGGGAACAGC  ATTCGTAACA  TCTAGGTACT  GGTATTATTT  1500
GCTGTTTTTT  AAAAAGAAG   GAAATCCGTT  TTGCAAGAAT  TGTCTGCTAT  TTAAGGGTAT  1560
ACGTGCTACG  GTCCACTAAT  CAAAGTGGT   ATCTCATTCT  GAAGAAAAG   TGTAAAAGG   1620
ACGATAAGGA  AAGATGTCCC  AACGATCTTC  ACAACACATT  GTAGGTATTC  ATTATGCTGT  1680
AGGACCTAAG  ATTGGCGAAG  GGTCTTTCGG  AGTAATATTT  GAGGGAGAGA  ACATTCTTCA  1740
TTCTTGTCAA  GCGCAGACCG  GTAGCAAGAG  GGACTCTAGT  ATAATAATGG  CGAACGAGCC  1800
AGTCGCAATT  AAATTCGAAC  CGCGACATTC  GGACGCACCC  CAGTTGCGTG  ACGAATTTAG  1860
AGCCTATAGG  ATATTGAATG  GCTGCGTTGG  AATTCCCCAT  GCTTATTATT  TTGGTCAAGA  1920
AGGTATGCAC  AACATCTTGA  TTATCGATTT  ACTAGGGCCA  TCATTGGAAG  ATCTCTTTGA  1980
GTGGTGTGGT  AGAAAATTTT  CAGTGAAAAC  AACCTGTATG  GTTGCCAAGC  AAATGATTGA  2040
TAGAGTTAGA  GCAATTCATG  ATCACGACTT  AATCTATCGC  GATATTAAAC  CCGATAACTT  2100
TTTAATTTCT  CAATATCAAA  GAATTTCACC  TGAAGGAAAA  GTCATTAAAT  CATGTGCCTC  2160
CTCTTCTAAT  AATGATCCCA  ATTTAATATA  CATGGTTGAC  TTTGGTATGG  CAAAACAATA  2220
TAGAGATCCA  AGAACGAAAC  AACATATACC  ATACCGTGAA  CGAAAATCAT  TGAGCGGTAC  2280
CGCCAGATAT  ATGTCTATTA  ATACTCATTT  TGGAAGAGAA  CAGTCACGTA  GGGATGATTT  2340
AGAATCGCTA  GGTCACGTTT  TTTTTTATTT  CTTGAGGGGA  TCCTTGCCAT  GGCAAGGTTT  2400
GAAAGCACCA  AACAACAAAC  TGAAGTATGA  AAAGATTGGT  ATGACTAAAC  AGAAATTGAA  2460
TCCTGATGAT  CTTTTATTGA  ATAATGCTAT  TCCTTATCAG  TTTGCCACAT  ATTTAAAATA  2520
TGCACGTTCC  TTGAAGTTCG  ACGAAGATCC  GGATTATGAC  TATTTAATCT  CGTTAATGGA  2580
TGACGCTTTG  AGATTAAACG  ACTTAAAGGA  TGATGGACAC  TATGACTGGA  TGGATTTGAA  2640
TGGTGGTAAA  GGCTGGAATA  TCAAGATTAA  TAGAAGAGCT  AACTTGCATG  GTTACGGAAA  2700
TCCAAATCCA  AGAGTCAATG  GCAATACTGC  AAGAAACAAT  GTGAATACGA  ATTCAAAGAC  2760
ACGAAATACA  ACGCCAGTTG  CGACACCTAA  GCAACAAGCT  CAAAACAGTT  ATAACAAGGA  2820
CAATTCGAAA  TCCAGAATTT  CTTCGAACCC  GCAGAGCTTT  ACTAAACAAC  AACACGTCTT  2880
GAAAAAAATC  GAACCCAATA  GTAAATATAT  TCCTGAAACA  CATTCAAATC  TTCAACGGCC  2940
AATTAAAAGT  CAAAGTCAAA  CGTACGACTC  CATCAGTCAT  ACACAAAATT  CACCATTTGT  3000
ACCATATTCA  AGTTCTAAAG  CTAACCCTAA  AAGAAGTAAT  AATGAGCACA  ACTTACCAAA  3060
CCACTACACA  AACCTTGCAA  ATAAGAATAT  CAATTATCAA  AGTCAACGAA  ATTACGAACA  3120
AGAAAATGAT  GCTTATTCTG  ATGACGAGAA  TGATACATTT  TGTTCTAAAA  TATACAAATA  3180
TTGTTGTTGC  TGTTTTTGTT  GCTGTTGATA  AAGCGATTTT  TATACTTTTC  TCTTTTTCCT  3240
```

| | | | | | | |
|---|---|---|---|---|---|---|
| TTTTTTTTT | GATTGGCTGT | TTCCTTATGC | CGCTCTTTCC | CAATTTATGA | CTTTCCAATA | 3300 |
| ATGTATTATT | TTGTTTCTCT | TTCTCTCTGT | TACCCTTTAT | TTTATCATCT | ACAATAATTG | 3360 |
| AATTCCGGAG | AGGGTAAAGA | AACAGGAAAA | AGAAGAAAAT | GAGACATAGT | CAGCATCGTA | 3420 |
| ATCGTTTTCC | TTCTGTATAT | TCCTTTATCA | AAAGACTACA | CGCACATATA | TATTAATCCC | 3480 |
| GGTATGTTTT | TGGTGTGCTA | AATCTATCTT | CAAGCACTAT | TATAGCATTT | TTTTAAGAAT | 3540 |
| ATCCAAAATA | ATATGTAATT | TATGATTAAT | CAAGGTTCAA | GAATTGGAGA | AACCGTGAGC | 3600 |
| GACTTCTTTG | ATACTTGGAT | GTAAGCTT | | | | 3628 |

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

| | | | |
|---|---|---|---|
| TGAAGATCGT | TGGCCCGGGT | TTCCTTATCG | TCC | 33 |

( 2 ) INFORMATION FOR SEQ ID NO:19:

( i ) SEQUENCE CHARACTERISTICS:
        ( A ) LENGTH: 2468 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

| | | | | | | |
|---|---|---|---|---|---|---|
| AATATTTCAA | GCTATACCAA | GCATACAATC | AACTCCAAGC | TTCGAGCGGC | CGCCAGTGTG | 60 |
| CTCTAAAGGA | AAAAGCGAGT | GCCTTTAGCC | TTAAAAGCGT | TATAATATTA | TTATGGCTTT | 120 |
| GGACCTCCGG | ATTGGGAACA | AGTATCGCAT | TGGTCGTAAA | ATTGGCAGTG | GATCTTTCGG | 180 |
| AGACATTTAT | CTTGGGACTA | ATGTCGTTTC | TGGTGAAGAG | GTCGCTATCA | AGCTAGAATC | 240 |
| AACTCGTGCT | AAACACCCTC | AATTGGAGTA | TGAATACAGA | GTTTATCGCA | TTTTGTCAGG | 300 |
| AGGGGTCGGA | ATCCCGTTTG | TTCGTTGGTT | CGGTGTAGAA | TGTGATTACA | ACGCTATGGT | 360 |
| GATGGATTTA | TTGGGTCCTT | CGTTGGAAGA | CTTGTTTAAT | TTTGCAATC | GAAAGTTTTC | 420 |
| TTTGAAAACA | GTTCTTCTCC | TTGCGGACCA | GCTCATTTCT | CGAATTGAAT | TCATTCATTC | 480 |
| AAAATCTTTT | CTTCATCGTG | ATATTAAGCC | TGATAACTTT | TTAATGGGAA | TAGGTAAAAG | 540 |
| AGGAAATCAA | GTTAACATAA | TTGATTTCGG | ATTGGCTAAG | AAGTATCGTG | ATCACAAAAC | 600 |
| TCACCTGCAC | ATTCCTTATC | GCGAGAACAA | GAATCTTACA | GGTACTGCAC | GCTATGCTAG | 660 |
| CATCAATACT | CATTTAGGTA | TTGAACAATC | CCGCCGTGAT | GACCTCGAAT | CTTTAGGTTA | 720 |
| TGTGCTCGTC | TACTTTGTC | GTGGTAGCCT | GCCTTGGCAG | GGATTGAAGG | CTACCACGAA | 780 |
| AAAGCAAAAG | TATGAAAAGA | TTATGGAGAA | GAAGATCTCT | ACGCCTACAG | AGGTCTTATG | 840 |
| TCGGGGATTC | CCTCAGGAGT | TCTCAATTTA | TCTCAATTAC | ACGAGATCTT | TACGTTTCGA | 900 |
| TGACAAACCT | GATTACGCCT | ACCTTCGCAA | GCTTTTCCGA | GATCTTTTTT | GTCGGCAATC | 960 |
| TTATGAGTTT | GACTATATGT | TTGATTGGAC | CTTGAAGAGA | AAGACTCAAC | AAGACCAACA | 1020 |
| ACATCAGCAG | CAATTACAGC | AACAACTGTC | TGCAACTCCT | CAAGCTATTA | ATCCGCCGCC | 1080 |
| AGAGAGGTCT | TCATTTAGAA | ATTATCAAAA | ACAAAACTTT | GATGAAAAAG | GCGGAGACAT | 1140 |

-continued

```
TAATACAACC GTTCCTGTTA TAAATGATCC ATCTGCAACC GGAGCTCAAT ATATCAACAG    1200
ACCTAATTGA TTAGCCTTTC ATATTATTAT TATATAGCAT GGGCACATTA TTTTTATATT    1260
TTCTTCTCAT CTGGAGTCTT CCAATACTTG CCTTTTATCC TCCAGACGTC CTTTAATTTT    1320
GTTGATAGCG CAGGGCTTTT TCCTTGGGAT GGCGAAAGTT ACTTGCTTA TAGTTTATTG    1380
AGGGTTCATA GCTTATTTGG CTGAAGATCT TGTGTTGACT TAAATTCTAT GCTAACCTCA    1440
TGATCATATC CTCATTATGG CAAGTTTTGG TGAAAAATTT TTTAATATTA GTACATTTGC    1500
TAATAATACA TTTGGTATTT GTTTTACTA CCTGTGAATC TATTCATACA TTATCATATA    1560
TGTTTCGAGC CAGGAACAGA AAAAGTGAG AGAATTTTCT GCAGAAATGA TCATAATTTT    1620
ATCTTCGCTT AACACGAATC CTGGTGACAG ATTATCGTGG TTTAAAGCCT TTTTTTTACG    1680
ACGCCATAAG CAAATTGGTT ACTTTTTAT GTGTGATGAG CCTTGGGGTT TAATCTAATT    1740
AGAAGGCATT GCATTCATAT ACTTTTAATA ATATATTATC AGCTATTTGC TGCTTTTCTT    1800
TATAGATACC GTCTTTTCCA AGCTGAACTC ATTAATCAG CGTCGTTTAA CCTTAGGATG    1860
CTTAAGATGC GTTTAAATTC AATGACTTAA TGCTCGAGGG ATGAATGGTT TGTTTTAGTT    1920
CGTGTTCTGG GTGCATGATC TCGTGCTTGA CTGTTTTATT GAAGCGTTCA TTTCATGAAG    1980
TGTCTTTCGA TGTTGTTCAC ACTTCTGTTT GCTAAATATA ATAAATATTT TGCTTTTCAC    2040
TTTAGAGCAC ACTGGCGGCC GCTCGAAGCT TTGGACTTCT TCGCCATTGG TCAAGTCTCC    2100
AATCAAGGTT GTCGGCTTGT CTACCTTGCC AGAAATTTAC GAAAGATGG AAAAGGGATC    2160
CAAATCGTTG GTAGATACTT GTTGACACTT CTAAATAAGC GAATTCTTA TGATTTATGA    2220
TTTTTATTAT TAAATAAGTT ATAAAAAAAA TAAGGTATAC AAATTTTAAA GTGACTCTTA    2280
GGTTTTAAAA CGAAAATTCT TATTCTTGAG TAACTCTTTC CTGTAGGTCA GGTTGCTTTC    2340
TCAGGTATAG CATGAGGTCG CTCTTATTGA CCACACCTCT ACCGGCATGC CGAGCAAATG    2400
CCTGCAAATC GCTCCCCATT TCACCCAATT GTAGATATGC TAACTCCAGC AATGAGCCGA    2460
TGAATCTC                                                             2468
```

( 2 ) INFORMATION FOR SEQ ID NO:20:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

```
GGGTTATAAT ATTATCCCGG GTTTGGACCT CCGG                                  34
```

( 2 ) INFORMATION FOR SEQ ID NO:21:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

```
TCCCTCTCTA GATATGGCGA GATAGTTA                                         28
```

( 2 ) INFORMATION FOR SEQ ID NO:22:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:22:

GTTTACACTC GAGGCATATA GTGATACA 28

( 2 ) INFORMATION FOR SEQ ID NO:23:

( i ) SEQUENCE CHARACTERISTICS:
  ( A ) LENGTH: 5093 base pairs
  ( B ) TYPE: nucleic acid
  ( C ) STRANDEDNESS: single
  ( D ) TOPOLOGY: linear ( i i ) MOLECULE TYPE: protein ( x i ) SEQUENCE DESCRIPTION: SEQ ID NO:23:

| | | | | | |
|---|---|---|---|---|---|
| GCTAGCTTTT | GCCGGGGAAC | CCATCCCGAA | AAAATTGCAA | AAAAAAAAT | AGCCGCCGAC | 60 |
| CGTTGGTCGC | TATTCACGGA | ATGATAGAAA | AATAGCCGCG | CTGCTCGTCC | TGGGTGACCT | 120 |
| TTTGTATATT | GTATAAAGAT | AAACATAGTG | CTATCAGGAA | TATCTTTATA | TACACACGCA | 180 |
| TACTGAATGT | GGTTGAAGTT | CAAAAAATAT | CACAAACGTT | AAGAAGTTTT | ACTGGTAAAC | 240 |
| ATATAGACAT | AGTGGAGCGC | TTGCTCGAGG | TCAAATGCAG | ACGGATACGA | GAGCGCGGGA | 300 |
| GGGAAACCGG | AGAAGGTCAA | TATGCCCATA | ATTCTTCTTC | TTTGAGGTTG | GCAATTATAT | 360 |
| ATTGTATCTG | AATTAGGCAA | ATAGAAAAGA | GACCTTACCA | TTAGCGCCAT | CGTAGAGTCC | 420 |
| CATTTCACCT | TTTCTTAGTT | CTTTATATAT | GTCTGCGTAT | GGCCCACATA | TGCGCGCACA | 480 |
| GTGCGCGCCA | CCCTCTAAGA | ACGATAAACA | TAAAATAAAC | ACATAAACAA | TCAACGACAG | 540 |
| TTCGCGCTTC | CCTCACTAAA | TATGGCGAGA | TAGTTAAACA | ATCATGGCTC | GTTCTTCCTT | 600 |
| GCCCAACCGC | CGCACCGCCC | AGTTCGAAGC | GAACAAGAGG | AGGACCATTG | CACATGCTCC | 660 |
| ATCTCCAAGT | CTTTCAAATG | GGATGCACAC | TCTAACGCCG | CCCACCTGTA | ACAATGGTGC | 720 |
| TGCCACTTCA | GACTCCAATA | TACATGTATA | TGTAAGGTGC | AGATCGCGTA | ATAAGCGAGA | 780 |
| AATAGAGGAA | AAAAGTAGTG | TAGTTATATC | TACACTAGGC | CCACAAGGGA | AAGAAATCAT | 840 |
| TCTGTCCAAC | GGTTCTCACC | AATCGTATTC | GTCCTCGAAG | AAAACTTACC | AATTTGATCA | 900 |
| GGTGTTCGGC | GCAGAATCTG | ACCAGGAAAC | AGTGTTTAAT | GCCACTGCAA | AAAACTACAT | 960 |
| TAAGGAAATG | TTGCACGGGT | ACAATTGTAC | AATATTTGCA | TACGGTCAAA | CGGGAACAGG | 1020 |
| TAAAACCTAC | ACTATGTCTG | GCGATATAAA | TATTCTCGGT | GATGTGCAAT | CTACCGATAA | 1080 |
| TCTATTATTA | GGAGAGCATG | CAGGTATCAT | ACCACGGGTT | CTGGTCGATT | TGTTTAAAGA | 1140 |
| ATTGAGCTCC | TTAAATAAAG | AGTACTCCGT | AAAAATATCC | TTTTAGAGT | TGTACAATGA | 1200 |
| AAATTTGAAA | GATCTGCTCT | CTGATAGTGA | GGACGATGAT | CCTGCAGTCA | ACGATCCCAA | 1260 |
| GAGGCAGATT | CGTATTTTTG | ACAATAACAA | CAATAATTCA | TCCATCATGG | TCAAGGGGAT | 1320 |
| GCAGGAAATC | TTTATTAACT | CTGCACACGA | AGGCTTGAAT | TTGCTAATGC | AGGGTTCGTT | 1380 |
| AAAAAGGAAA | GTGGCCGCTA | CTAAATGCAA | CGATCTTTCA | TCAAGGTCTC | ACACCGTCTT | 1440 |
| TACAATCACA | ACAAACATAG | TTGAGCAAGA | TAGCAAAGAC | CATGGACAAA | ACAAAAATTT | 1500 |
| TGTTAAAATT | GGCAAATTGA | ATTTGGTGGA | TTTGGCAGGC | AGTGAAAACA | TCAACAGATC | 1560 |
| GGGTGCGGAG | AATAAAAGGG | CTCAAGAAGC | TGGCCTAATA | AACAAATCGC | TGCTAACACT | 1620 |
| AGGCCGTGTT | ATCAACGCAC | TCGTTGATCA | TTCTAACCAT | ATACCTTACA | GAGAATCTAA | 1680 |

```
GCTAACAAGA  TTGCTACAAG  ACTCTTTAGG  TGGTATGACG  AAAACATGCA  TTATCGCAAC  1740
TATATCACCT  GCGAAAATAT  CCATGGAAGA  GACTGCAAGT  ACGCTAGAAT  ATGCAACGAG  1800
AGCCAAATCA  ATTAAGAATA  CTCCACAAGT  AAATCAGTCT  TTATCGAAGG  ATACATGTCT  1860
CAAAGACTAC  ATTCAAGAGA  TTGAAAATT   AAGAAATGAT  TTGAAAATT   CAAGAAACAA  1920
ACAAGGTATA  TTTATAACTC  AAGATCAGTT  GGACCTTTAC  GAGAGCAATT  CTATCTTGAT  1980
TGATGAGCAA  AATCTAAAAA  TACATAACCT  GCGAGAACAA  ATTAAAAAAT  TCAAAGAAAA  2040
CTACCTGAAC  CAATTAGATA  TCAATAATCT  TTTACAGTCT  GAAAGGAAA   AACTAATTGC  2100
CATAATACAG  AATTTTAATG  TCGATTTTTC  TAACTTTTAC  TCGGAAATCC  AAAAAATTCA  2160
CCATACTAAT  CTCGAACTAA  TGAATGAAGT  CATACAACAG  AGAGATTTT   CACTAGAAAA  2220
TTCTCAAAAA  CAGTATAATA  CGAACCAGAA  CATGCAATTA  AAATCTCTC   AACAAGTTTT  2280
ACAGACTTTG  AACACTTTAC  AGGGCTCTTT  AAATAATTAT  AACTCTAAAT  GTTCCGAAGT  2340
TATCAAAGGC  GTCACCGAAG  AACTAACCAG  GAACGTAAAT  ACCCATAAGG  CGAAACACGA  2400
TTCTACTCTC  AAATCGTTAT  TAAACATTAC  TACTAACTTA  TTGATGAATC  AGATGAACGA  2460
ACTGGTGCGT  AGTATTTCGA  CTTCATTGGA  AATATTTCAG  AGTGATTCTA  CTTCTCACTA  2520
TCGTAAAGAT  TTGAATGAAA  TCTACCAATC  ACATCAACAA  TTTCTAAAAA  ATTTACAAAA  2580
CGATATTAAA  AGCTGTCTTG  ATTCGATAGG  CAGTTCAATT  CTAACTTCCA  TAAACGAAAT  2640
ATCGCAAAAT  TGCACCACTA  ACTTGAATAG  TATGAATGTT  TTAATAGAAA  ACCAGCAGTC  2700
AGGATCATCG  AAATTAATTA  AGAGCAAGA   TTTAGAAATA  AAAAAACTGA  AAAACGATCT  2760
GATCAATGAG  CGCAGGATTT  CTAACCAATT  CAACCAACAG  TTGGCTGAAA  TGAAGCGATA  2820
TTTTCAGGAT  CACGTTTCCA  GGACGCGTAG  TGAATTCCAC  GACGAACTTA  ACAAATGTAT  2880
CGATAACCTA  AAAGATAAAC  AATCTAAGTT  GGATCAAGAT  ATCTGGCAGA  AGACGGCCTC  2940
TATTTTCAAC  GAAACAGATA  TCGTAGTTAA  TAAAATTCAT  TCCGACTCAA  TAGCATCCCT  3000
CGCTCATAAT  GCTGAAAACA  CTTTGAAAAC  GGTTTCTCAG  AACAATGAAA  GCTTTACTAA  3060
CGATTTAATC  AGTCTATCAC  GCGGAATGAA  CATGGACATA  TCCTCCAAAC  TGAGAAGTTT  3120
GCCCATCAAT  GAATTTTTAA  ACAAGATATC  ACAAACCATT  TGTGAAACCT  GTGGCGATGA  3180
TAACACAATC  GCATCAAATC  CAGTATTGAC  CTCTATTAAA  AAATTTCAAA  ATATAATTTG  3240
TTCAGACATT  GCCCTAACAA  ATGAGAAGAT  CATGTCATTA  ATAGATGAAA  TACAATCACA  3300
AATTGAAACC  ATATCTAATG  AAAACAATAT  CAATTTGATT  GCAATAAATG  AAAATTTTAA  3360
TTCTTTGTGC  AATTTTATAT  TAACTGATTA  CGATGAGAAT  ATTATGCAAA  TCTCAAAAAC  3420
ACAAGATGAG  GTGCTTTCTG  AACATTGCGA  GAAGCTACAA  TCACTGAAAA  TACTGGGTAT  3480
GGACATTTTC  ACTGCTCACA  GCATAGAAAA  ACCCCTTCAT  GAGCATACAA  GACCTGAAGC  3540
GTCAGTAATC  AAGGCTTTAC  CCTTATTGGA  TTATCCAAAA  CAATTTCAGA  TTTATAGGGA  3600
TGCTGAAAAT  AAGAGCAAAG  ACGACACATC  TAATTCTCGT  ACTTGTATAC  CAAACTTGTC  3660
AACTAATGAA  AATTTTCCTC  TTTCACAATT  CAGTCCAAAA  ACCCCAGTGC  CAGTGCCTGA  3720
TCAACCTCTA  CCAAAAGTTC  TTATACCGAA  AAGCATAAAC  TCGGCCAAGT  CCAATAGATC  3780
AAAGACCTTA  CCAAATACAG  AGGGTACTGG  ACGAGAATCG  CAGAACAATT  TGAAGAGAAG  3840
ATTTACCACC  GAGCCAATAT  TGAAGGGAGA  AGAAACTGAA  AATAATGACA  TACTGCAAAA  3900
TAAAAAACTT  CATCAATAAG  GGGATATAGC  CATTGTAAAA  TATTTGTATC  ACTATATGCA  3960
TTGAGTGTAA  ACTGTTGCAC  CTATAAAGAA  TGAAAACAAT  CTAGTATGTG  TACTTACATA  4020
ATTACACAGT  CTTTTTTTTT  TTTACCTTGT  TTATCCTTCT  TGTTCTTCAA  GCTTGTAGGT  4080
```

```
TTTTTTGACT  CAGTTTTTAC  TGCAGGAAAA  TCTTTACGAA  TCATGTTTGA  ACTGCCCATA    4140

TTTGATAAAC  TAACTTCTTG  CTTTGCTGCC  ATCGACTGCT  CAGCAACTTC  CCTTGACATT    4200

CCCTTTGCTG  AGGAAGAACT  TTTCCTGATG  CTTGTATCAG  AACCCGTTTT  AATACCATTT    4260

CTATTCGTGT  TTGAATTCAT  GTTAATTTGC  AAACCTTGTG  GCTCACGATC  ACGTTTTGGA    4320

TTTCCAGTAA  AGAATGTTTC  AGATTTTGAA  GAAACTCTTG  AATTTGACCC  TACGTTACTT    4380

GTTGACTGT   CCACAGTAGA  GAATAAATTC  AAAGTACTGA  TACTTTTATT  TTTTTATGC     4440

TGTTTTTTAC  CAATGCTGGC  TAGTCCACCG  TCCCTTGAGC  GTAGCTATT   AATCGCCCTC    4500

TTGTCCTCGT  TCCCTGCAGC  TTTCTCGTAC  CATTTCCATG  CGTATTCCAT  GTTACGATCA    4560

CAGCCCTTGC  CATGCTCATA  GAAGTAGCCC  AGAGTGAATT  GGGCCTTTGG  CAAACCAGCA    4620

TTAGCTGCAC  GCAAGGCCCA  TTGAAAAGCC  TCATTTTCAT  CTTTTTCAAA  AGCAGGTTCT    4680

GCTCCCAGTA  AGTACCATGC  ACATAAACCT  AACATTGCCA  CAGAATCGCC  TTTTAACGCT    4740

GCCTGCGTAT  AATAGTGTAC  AGAAAGTGAT  GTATCCTGCC  CTACTGTATC  ATTACCTGTT    4800

TCATAAATCT  GTGCCAACAA  AGTTGCTGAA  GGAACATGCC  CTAAACTTGC  TGCTTGAATA    4860

TATAGTTCCA  TTGCATACTT  TTCATCCGGA  ATGACAACAT  CTAAGAACCC  TTCATGATAA    4920

ATCTTAGCCA  ATTCGTATGG  TGCTGCGGCC  GTCAACTCAT  TAGCTCTTGC  TGCAGCCCTT    4980

GATAACCATT  TTACCCCATT  TAATTTAGTA  TTAACGTCGG  TTGGAAGACC  CATTCTGCCG    5040

TAGAATGAAT  AAAGTCCCAA  TTTATACATT  GCTGAGGGAT  GATTCCTGCT  AGC           5093
```

( 2 ) INFORMATION FOR SEQ ID NO:24:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:24:

```
GATAGTTAAG  GATCCATGGC  TCGTTCTTCC  TTGCCCAACC  GC            42
```

( 2 ) INFORMATION FOR SEQ ID NO:25:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:25:

```
AAACTTCATC  AATGCGGCCG  CTAAGGGGAT  CCAGCCATTG  TAAAT         45
```

( 2 ) INFORMATION FOR SEQ ID NO:26:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:26:

```
TTTCCTTGTT  TATCCTTTTC  CAA                                   23
```

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

| | | | |
|---|---|---|---|
| GATCACTTCG | GATCCGTCAC | ACCCAGTTAG | 30 |

( 2 ) INFORMATION FOR SEQ ID NO:28:

( i ) SEQUENCE CHARACTERISTICS:
        ( A ) LENGTH: 2870 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

| | | | | | | |
|---|---|---|---|---|---|---|
| AATTTCCTTG | TTTATCCTTT | TCCAATAGCG | GAACAATTGA | TAATAAAGCA | ATGTAAGCAG | 60 |
| AAGCGAAAAA | TAAAAGAAA | TAGGCTGCAG | AGATTCACAG | GCTGCGCTCT | AGAAACATTT | 120 |
| GAAATCAAGG | CAAACATAGA | ACACTTGATA | AAATTCTTAC | CATAATACCA | CCATTGATGA | 180 |
| TTCAAAAAAT | GAGCCCAAGC | TTAAGGAGGC | CATCAACGAG | GTCTAGTTCT | GGTTCAAGTA | 240 |
| ATATCCCACA | ATCGCCCTCT | GTACGATCAA | CTTCATCGTT | TTCTAATCTG | ACAAGAAACT | 300 |
| CCATACGGAG | CACCTCTAAT | TCGGGTTCTC | AGTCGATTTC | TGCATCTTCC | ACTAGAAGTA | 360 |
| ACTCCCCACT | AAGATCCGTA | TCAGCCAAAT | CCGATCCCTT | CCTTCACCCA | GGTAGGATAA | 420 |
| GGATCAGGCG | GAGCGACAGT | ATTAACAACA | ACTCGAGAAA | AAACGATACA | TATACTGGGT | 480 |
| CAATCACTGT | GACCATCCGG | CCGAAACCAC | GGAGCGTTGG | AACTTCCCGT | GACCATGTGG | 540 |
| GGCTAAAATC | GCCCAGGTAC | TCTCAACCAA | GATCCAACTC | ACATCACGGT | AGCAATACAT | 600 |
| TTGTTAGAGA | CCCCTGGTTT | ATTACTAATG | ACAAACAAT | AGTGCATGAA | GAAATTGGAG | 660 |
| AGTTCAAGTT | CGATCATGTT | TTTGCTTCCC | ATTGCACTAA | TTTGGAAGTT | TATGAAAGAA | 720 |
| CCAGTAAACC | AATGATTGAT | AAGTTATTGA | TGGGGTTTAA | TGCCACCATA | TTTGCGTACG | 780 |
| GTATGACCGG | GTCAGGTAAA | ACGTTTACAA | TGAGCGGAAA | TGAACAAGAG | CTAGGCCTAA | 840 |
| TTCCTTTATC | TGTGTCGTAT | TTATTTACCA | ATATCATGGA | ACAATCAATG | AATGGCGATA | 900 |
| AAAAGTTCGA | CGTTATAATA | TCGTACCTCG | AAATTTACAA | TGAAGGATT | TACGACCTGT | 960 |
| TAGAAAGCGG | ATTAGAAGAA | TCCGGTAGTA | GAATCAGTAC | TCCTTCAAGG | TTATATATGA | 1020 |
| GCAAGAGCAA | CAGCAATGGA | TTGGGCGTAG | AATTAAAAAT | CAGAGATGAC | TCTCAGTATG | 1080 |
| GGGTCAAAGT | TATCGGTCTC | ACCGAAAGAA | GATGTGAAAG | TAGTGAAGAA | TTATTGAGGT | 1140 |
| GGATTGCAGT | TGGTGACAAA | AGTAGGAAAA | TTGGCGAAAC | TGACTACAAT | GCAAGAAGCT | 1200 |
| CACGATCTCA | TGCCATTGTA | CTGATTCGTT | TAACAAGTAC | TAACGTAAAG | AACGGCACCT | 1260 |
| CAAGATCGAG | TACATTGTCG | TTGTGTGACC | TAGCAGGTTC | GGAAAGGGCT | ACGGGGCAAC | 1320 |
| AAGAGAGGAG | AAAGGAAGGT | TCATTCATCA | ACAAATCCTT | ACTTGCTTTG | GGGACTGTGA | 1380 |
| TATCCAAACT | CAGTGCCGAC | AAGATGAACT | CAGTAGGCTC | AAACATTCCC | TCGCCATCTG | 1440 |
| CAAGTGGCAG | TAGCAGCAGT | AGTGGAAATG | CTACCAATAA | CGGCACTAGC | CCAAGCAACC | 1500 |
| ACATTCCATA | TCGTGATTCT | AAATTGACTA | GATTATTGCA | GCCGGCACTA | AGCGGTGACA | 1560 |

-continued

| | | | | | |
|---|---|---|---|---|---|
| GCATAGTGAC | AACGATATGT | ACAGTCGACA | CCAGAAATGA | TGCGGCAGCG | GAAACTATGA | 1620
| ATACGCTGAG | GTTTGCATCA | AGAGCGAAAA | ACGTCGCACT | TCATGTATCC | AAAAAATCCA | 1680
| TCATCAGTAA | CGGGAATAAC | GATGGAGATA | AAGATCGCAC | CATTGAGCTA | CTGAGACGCC | 1740
| AATTGGAAGA | ACAACGTAGG | ATGATCTCTG | AATTGAAGAA | CCGTTCAAAC | ATTGGCGAGC | 1800
| CCTTAACCAA | ATCTTCCAAT | GAAAGTACTT | ATAAAGACAT | TAAAGCCACC | GGCAATGATG | 1860
| GTGATCCGAA | TTTGGCTCTA | ATGAGAGCGG | AGAATCGAGT | ATTAAAATAT | AAACTAGAGA | 1920
| ATTGTGAAAA | ACTACTAGAT | AAAGATGTGG | TTGATTTGCA | AGATTCTGAG | ATTATGGAAA | 1980
| TTGTAGAAAT | GCTTCCCTTT | GAGGTCGGCA | CCCTTTTGGA | AACAAAGTTC | CAAGGTTTGG | 2040
| AATCACAAAT | AAGGCAATAT | AGGAAATACA | CTCAAAAACT | TGAAGACAAG | ATCATGGCGC | 2100
| TAGAAAAAAG | TGGTCATACT | GCAATGTCGC | TAACTGGGTG | TGACGGCACT | GAAGTGATCG | 2160
| AATTACAGAA | GATGCTCGAG | AGGAAGGATA | AAATGATTGA | GGCCCTGCAG | AGTGCCAAAC | 2220
| GACTGCGGGA | TAGGGCTTTG | AAACCACTCA | TTAATACACA | GCAATCACCG | CACCCTGTCG | 2280
| TGGATAACGA | TAAATGATTA | GGTGAGGGTC | CCAGATCTCG | GGTGCTTTTT | TCCTTGTGCG | 2340
| GATTGTTCTG | TAGACTGCGC | CTCCGCTTCC | CGGCCTTGCT | TGAACGGGAT | CTATTCTCAG | 2400
| AAGACAGCGC | ATAAAAGGCA | GTTTTTAGGC | ACTTCTCGTT | AAGAAAATAC | ACAAATAATG | 2460
| GATTTACAGT | TCGTTTCAGT | GTGGTACCAA | AAAATTTCAT | CAGCTAATAA | AGATCAAGAA | 2520
| GTTTTGGGGT | TGTTTCGAGT | CTGTCTCGGC | CTTAATTGTG | CAGGTACTAA | AGGAATTAAT | 2580
| ATATAAAGAT | TGTTAAGGCC | AAGTGACTGA | AACTTGCAAA | CGTCTTTGAA | TCAGGCTTAT | 2640
| CTCTTAAATA | CTTATATATA | TGTTCTTTTA | TAGACTTCAT | AATCTCTTGT | TCCAAGAACA | 2700
| GTAAAGAGCA | ATTAAAAAAA | GGAAAATAAC | AGTTAAAGAT | GATAGCGGAT | TCATCAGTTT | 2760
| TGAAAAAGCA | CACAGCAATC | AAGAGAAGTA | CGAGAATAAT | ATCGCTAACA | CTCGTTTTGC | 2820
| TTGGCGTATT | TAGCTTCTTA | CTACTTACAT | GGAATGACTC | CTTGGAATTC | | 2870

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

ACCATAATAC CAGGATCCAT GATTCAAAAA　　　　　　　　　　　　　　　　　　　　　　　30

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

CCTGTCGTGG ATAGCGGCCG CTAGGATCCT GAGGGTCCCA GA　　　　　　　　　　　　　　42

( 2 ) INFORMATION FOR SEQ ID NO:31:

( i ) SEQUENCE CHARACTERISTICS:
        ( A ) LENGTH: 28 base pairs
        ( B ) TYPE: nucleic acid (C) STRANDEDNESS: single
(D) TOPOLOGY: linear (i i) MOLECULE TYPE: DNA (x i) SEQUENCE DESCRIPTION: SEQ ID NO:31:

ACATCATCTA GAGACTTCCT TTGTGACC                                                                              28

(2) INFORMATION FOR SEQ ID NO:32:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:32:

TATATAATCG ATTGAAAGGC AATATC                                                                                26

(2) INFORMATION FOR SEQ ID NO:33:

(i) SEQUENCE CHARACTERISTICS:
(A) LENGTH: 3883 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:33:

| | | | | | | |
|---|---|---|---|---|---|---|
| AGCAAGAATT | GAACATGGAT | GAATTCATTG | GATCAAAGAC | CGATTTAATC | AAAGATCAAG | 60 |
| TGAGAGATAT | TCTTGATAAA | TTGAATATTA | TTTAATTCTT | CATTTAGAAA | AATTTCAGCT | 120 |
| GCTTTTTTTT | TTCTTTTTCT | TTCCTTAGGC | GTCTCGAGGT | TACAAGTCGG | AGTCCCTCTT | 180 |
| CACTATCGTT | TGTCCACTTT | TTTTATATCC | CCATTATTTT | CAATCTGAAT | TCATTTTTT | 240 |
| TTTTTAATT | CATGAAATTT | ATATGTCCCA | CGTATTACTA | CATATTTGCG | TTTTTAATTA | 300 |
| AATAAATAAC | TGTTACTTTT | ATTATATCTT | ATTTGCAGAT | CACTTATCTG | ATCAAATGTT | 360 |
| TTCGTTTTCG | TGTGTGGTGA | CGATGTATTA | GGTACGCGAA | ATAAACAAAA | CAAACAAACA | 420 |
| AGGCCGCAAC | AATAACATCA | TCTAAAGACT | TCCTTTGTGA | CCCGCTTCTC | AACAGCGGGT | 480 |
| GTAGAACTTA | TGGTATGGCC | AGAAAGTAAC | GTTGAGTATA | GATACAGAAG | CAAGCAATTC | 540 |
| AAAGGAAAAA | GTAATAAAAA | GTATATAAAA | GCGCAAAAAA | TACAACAAGA | AAGAATTTGT | 600 |
| TTGATGCCAG | CGGAAAACCA | AAATACGGGT | CAAGATAGAA | GCTCCAACAG | CATCAGTAAA | 660 |
| AATGGCAACT | CTCAGGTTGG | ATGTCACACT | GTTCCTAATG | AGGAACTGAA | CATCACTGTA | 720 |
| GCTGTGCGAT | GCAGAGGAAG | GAATGAAAGG | GAAATTAGTA | TGAAAAGCTC | CGTTGTGGTA | 780 |
| AATGTTCCAG | ATATTACAGG | TTCTAAAGAA | ATTTCCATTA | ACACGACGGG | AGATACCGGT | 840 |
| ATAACTGCTC | AAATGAATGC | CAAGAGATAC | ACAGTGGACA | AAGTCTTCGG | TCCCGGCGCT | 900 |
| TCCCAGGATC | TAATTTTTGA | TGAAGTGGCG | GGCCCATTAT | TCCAGGATTT | CATTAAAGGT | 960 |
| TACAATTGCA | CCGTACTGGT | ATATGGTATG | ACGTCAACAG | GTAAAACATA | TACAATGACG | 1020 |
| GGCGACGAAA | AGTTATATAA | TGGTGAATTG | AGCGATGCAG | CAGGAATTAT | ACCGAGGGTT | 1080 |
| CTTTTGAAGT | TGTTTGACAC | ATTGGAACTA | CAACAGAACG | ATTACGTAGT | AAAATGTTCG | 1140 |
| TTCATTGAAC | TCTACAACGA | AGAATTGAAG | GACCTCTTGG | ACAGCAATAG | CAACGGCTCT | 1200 |
| AGTAATACTG | GCTTTGACGG | CCAATTTATG | AAAAAATTGA | GGATTTTGC | TTCAAGCACA | 1260 |
| GCAAATAATA | CCACTAGCAA | CAGTGCTAGT | AGTTCCAGGA | GTAATTCTAG | GAACAGTTCT | 1320 |

```
CCGAGGTCAT TAAATGATCT AACACCTAAA GCTGCTCTAT TAAGAAAAAG GTTAAGGACA    1380
AAATCACTGC CGAATACCAT CAAGCAACAG TATCAACAAC AACAGGCAGT GAATTCCAGG    1440
AACAACTCTT CCTCTAACTC TGGCTCTACC ACTAATAATG CTTCTAGTAA CACCAACACA    1500
AATAACGGTC AAAGAAGTTC GATGGCTCCA AATGACCAAA CTAATGGTAT ATACATCCAG    1560
AATTTGCAAG AATTTCACAT AACAAATGCT ATGGAGGGGC TAAACCTATT ACAAAAGGC     1620
TTAAAGCATA GGCAAGTAGC GTCCACTAAA ATGAACGATT TTTCCAGTAG ATCTCATACC    1680
ATTTTTACAA TCACTTTGTA TAAGAAGCAT CAGGATGAAC TATTTAGAAT TTCCAAAATG    1740
AATCTTGTGG ATTTAGCTGG TTCAGAAAAC ATCAACAGAT CCGGAGCATT AAATCAACGT    1800
GCCAAAGAAG CTGGTTCAAT CAACCAAAGT CTATTGACGC TGGGCAGGGT CATAAACGCA    1860
CTCGTAGATA AAAGCGGCCA TATACCTTTC CGTGAATCGA AATTGACCCG CCTGCTTCAA    1920
GATTCCCTGG GTGGTAATAC GAAAACCGCA CTAATTGCTA CTATATCGCC TGCAAAGGTA    1980
ACTTCTGAAG AAACCTGCAG TACATTAGAG TATGCTTCGA AGGCTAAAAA CATTAAGAAC    2040
AAGCCGCAAC TGGGTTCATT TATAATGAAG GATATTTTGG TTAAAAATAT AACTATGGAA    2100
TTAGCAAAGA TTAAATCCGA TTTACTCTCT ACAAAGTCCA AGAAGGAAT  ATATATGAGC    2160
CAAGATCACT ACAAAAATTT GAACAGTGAT TTAGAAAGTT ATAAAAATGA AGTTCAAGAA    2220
TGTAAAAGAG AAATTGAAAG TTTGACATCG AAAAATGCAT TGCTAGTAAA AGATAAATTG    2280
AAGTCAAAAG AAACTATTCA ATCTCAAAAT TGCCAAATAG AATCATTGAA AACTACCATA    2340
GATCATTTAA GGGCACAACT AGATAAACAG CATAAAACTG AAATTGAAAT ATCCGATTTT    2400
AATAACAAAC TACAGAAGTT GACTGAGGTA ATGCAAATGG CCCTACATGA TTACAAAAAA    2460
AGAGAACTTG ACCTTAATCA AAAGTTTGAA ATGCATATTA CTAAAGAAAT TAAAAAATTG    2520
AAATCTACAC TGTTTTTACA ATTAAACACT ATGCAACAGG AAAGTATTCT TCAAGAGACT    2580
AATATCCAAC CAAATCTTGA TATGATCAAA AATGAAGTAC TGACTCTTAT GAGAACCATG    2640
CAAGAAAAAG CTGAACTAAT GTACAAAGAC TGTGTGAAGA AAATTTTAAA CGAATCTCCT    2700
AAATTCTTCA ATGTTGTTAT TGAGAAAATC GACATAATAA GAGTAGATTT CCAAAAATTT    2760
TATAAAAATA TAGCCGAGAA TCTTTCTGAT ATTAGCGAAG AAAATAACAA CATGAAACAG    2820
TACTTAAAAA ACCATTTTTT CAAGAATAAC CATCAAGAAT TACTGAATCG TCATGTGGAT    2880
TCTACTTATG AAAATATTGA GAAGAGAACA AACGAGTTTG TTGAGAACTT TAAAAAGGTC    2940
CTAAATGACC ACCTTGACGA AAATAAAAAA CTAATAATGC ACAATCTGAC AACTGCAACC    3000
AGCGCGGTTA TTGATCAAGA AATGGATCTG TTTGAACCCA AGCGCGTTAA ATGGGAAAAT    3060
TCATTTGATC TGATAAATGA TTGTGACTCC ATGAATAACG AATTCTATAA TAGCATGGCA    3120
GCGACGCTAT CGCAAATCAA GAGTACTGTT GATACATCAT CAAATTCGAT GAATGAGTCT    3180
ATTTCAGTCA TGAAGGACA  AGTGGAAGAA TCGGAGAACG CTATATCCCT TTTGAAGAAC    3240
AATACCAAAT TTAATGATCA ATTTGAGCAG CTTATTAACA AGCATAACAT GTTGAAAGAT    3300
AACATTAAAA ATTCGATAAC ATCAACACAC TCTCATATAA CTAATGTGGA TGATATCTAT    3360
AATACGATTG AAAACATAAT GAAAACTAT  GGTAACAAGG AAAACGCTAC CAAAGACGAA    3420
ATGATCGAGA ACATATTGAA GGAAATACCA AATCTAAGTA AGAAAATGCC GTTAAGGTTA    3480
TCAAACATAA ATAGCAATTC AGTGCAAAGT GTAATATCGC CCAAAAAGCA TGCAATTGAA    3540
GATGAAAACA AATCCAGTGA AAATGTGGAC AATGAGGGCT CGAGAAAAAT GTTAAAGATT    3600
GAATAGTTGA TATTGCCTTT CAGTCGAATA TATATTCAAA CTAGTGGTTA ATAAAAACAA    3660
AGTATGTAAA GAATACTCAG TTATTCATTA GAAGGCAAGA CAGAAGAGAA GGGTGTGAAA    3720
```

CCACCTCTAC CAAACACACC AAGAGATGAA CCTAAATCAA ATTTTCACAG AGCTAACTAT 3780

ATAAACGTTT GGATTCGTGT GTACTATCTT TATTTACGGA AATAAGTTGT AATATTAAAA 3840

AAAAAAAAAA ACATTTGAT GGACAATGAA TTTCTCTAAT TTT 3883

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

CGGGTGTAGG ATCCATGGTA TGGCCAGAAA GTAACG 36

( 2 ) INFORMATION FOR SEQ ID NO:35:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

GTGGACAATG GCGGCCGCAG AAAAAGGATC CAGATTGAAT AGTTGATATT GCC 53

( 2 ) INFORMATION FOR SEQ ID NO:36:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

GAATATTCTA GAACAACTAT CAGGAGTC 28

( 2 ) INFORMATION FOR SEQ ID NO:37:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

TTGTCACTCG AGTGAAAAAG ACCAG 25

( 2 ) INFORMATION FOR SEQ ID NO:38:

( i ) SEQUENCE CHARACTERISTICS:
        ( A ) LENGTH: 3466 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

| | | | | | |
|---|---|---|---|---|---|
| CTGCAGCAGA | AAATCCAGTA | GAACCATCAT | CATGTTTGCT | GTTTTTCGAT | TTTTTCTTTC | 60
| TTGGGAAGTC | GTCGTCCTCT | TCTTCTTCAT | CATCATCTTC | TTCAGCATCA | CTTTGTTCGT | 120
| TATCTATAAT | TTTAGATGAT | TCATCGCTAG | AGCTATTCTG | CTCGTCTTCT | TCGGCTTCAT | 180
| CACCTTCCAT | TATTGTATCT | TTTTCCGGCT | CATTACTTAA | CTCTTGGTTG | CCACTATTCC | 240
| TTTTTTCACG | CCCAAATTCT | GCATTCTTTC | TGGTTCTTTT | CTTATCCTTA | GTGTCTACTC | 300
| TGTGCTTGGA | GCCCATGATC | AATTATGTAC | TGATTTTCCT | TCGGCTTCTC | TATCGCTTTA | 360
| TTCATAGCAT | CTGTTTATTA | CCTTTCCTTA | TATCTTATGG | GCATCGAATC | CTAGATTTTT | 420
| TTCTTTCAAA | ATTTTCCAAT | AAGAGGGTAA | TGGAGATACA | CCAAAATGAA | TCTCAAACAA | 480
| AATCAAAACA | AACACTGTTT | ACAATTTGAT | GCGCCTCGAA | TCAAAATATG | ATGATGAGTA | 540
| TTACAGCTAA | AAAAATTATC | GAATATTATA | TAAGCATTAA | AGCTATCAAT | TTTTCCGCTC | 600
| TTTGTGTTTC | TTATTATTCT | ATTTGAATAT | ACCAGAACAA | CTATCCGGAG | TCTTTGTTTA | 660
| AAAAAGGTAG | ATTTTGAAAT | AAAGGACTTA | GAGAAATTCT | GGCAACTATT | AAAGTATGGA | 720
| ATCACTTCCA | CGTACTCCCA | CAAAAGGCAG | ATCTACGCAG | CATCTCTCGA | CACCATCGCC | 780
| GAAGAATGAT | ATTTTAGCTA | TGAATGGCCA | CAAAAGAAGA | AATACAACAA | CTCCACCGCC | 840
| TAAGCACACT | CTTCTGAAGC | CGCAACGTAC | GGATATTCAT | AGACACTCAT | TAGCTAGTCA | 900
| GAGTCGCATA | TCCATGTCAC | CTAATCGCGA | GCTTTTAAAG | AATTATAAAG | GTACAGCAAA | 960
| TTTGATTTAT | GGAAACCAGA | AAAGCAACTC | CGGTGTAACT | TCCTTTTATA | AAGAAAATGT | 1020
| TAATGAACTC | AATAGAACAC | AAGCAATCTT | ATTTGAGAAA | AAGGCAACAC | TAGATTTACT | 1080
| CAAAGATGAA | CTAACAGAAA | CGAAAGAGAA | AATCAATGCC | GTTAATCTCA | AATTTGAAAC | 1140
| CCTTCGTGAA | GAAAAGATAA | AAATTGAACA | GCAACTGAAT | TTGAAAAACA | ATGAACTTAT | 1200
| CTCGATTAAA | GAAGAATTTT | TGTCAAAGAA | GCAGTTCATG | AATGAAGGAC | ATGAAATACA | 1260
| TTTAAAGCAG | CTAGCGGCAT | CTAATAAAAA | AGAGCTGAAA | CAAATGGAAA | ATGAATACAA | 1320
| AACAAAAATT | GAGAAATTGA | AATTTATGAA | GATTAAACAG | TTTGAAAATG | AAAGAGCGTC | 1380
| GCTTTTAGAT | AAAATAGAAG | AGGTAAGAAA | TAAAATCACC | ATGAACCCTT | CCACTTTACA | 1440
| GGAAATGTTG | AACGATGTTG | AACAAAAGCA | TATGCTTGAA | AAAGAAGAAT | GGCTTACAGA | 1500
| GTACCAATCG | CAGTGGAAAA | AGGATATAGA | GCTGAATAAT | AAACATATGC | AAGAAATCGA | 1560
| AAGCATAAAA | AAGGAAATCG | AAAATACATT | AAAACCTGAG | TTGGCAGAAA | AAAAGAAGCT | 1620
| CTTAACAGAA | AAGCGTAACG | CGTATGAAGC | TATCAAAGTA | AAAGTTAAAG | AAAAGGAAGA | 1680
| GGAAACTACA | AGGCTGAGAG | ATGAGGTGGC | ATTAAAACAG | AAAACTAATT | TAGAAACTTT | 1740
| GGAAAAGATC | AAAGAACTTG | AGGAATATAT | AAAAGACACT | GAACTGGGTA | TGAAGGAGTT | 1800
| GAATGAAATT | CTGATTAAAG | AGGAAACGGT | TAGACGCACA | TTGCATAATG | AGTTACAAGA | 1860
| GTTAAGAGGA | AATATACGAG | TTTATTGTAG | GATTCGTCCA | GCTCTAAAAA | ATTTGGAAAA | 1920
| TTCTGATACT | AGCCTTATTA | ATGTTAATGA | ATTTGATGAC | AATAGTGGTG | TTCAATCTAT | 1980
| GGAAGTGACG | AAAATACAAA | ACACAGCGCA | AGTGCATGAA | TTCAAATTTG | ATAAAATATT | 2040
| TGATCAACAG | GATACAAATG | TGGATGTTTT | TAAAGAAGTT | GGTCAGTTAG | TGCAAAGTTC | 2100
| ATTAGATGGA | TATAATGTTT | GTATCTTCGC | ATACGGACAA | ACAGGATCTG | GGAAAACTTT | 2160
| CACGATGTTA | AATCCAGGTG | ATGGTATCAT | TCCGTCCACA | ATATCTCATA | TATTTAACTG | 2220
| GATCAATAAA | TTAAAGACAA | AAGGATGGGA | TTATAAAGTT | AACTGCGAAT | TCATTGAGAT | 2280
| CTACAACGAG | AACATCGTAG | ACTTATTGAG | AAGTGATAAT | AATAATAAAG | AAGACACAAG | 2340
| CATTGGCTTA | AAGCACGAAA | TACGTCATGA | TCAGGAAACT | AAGACTACCA | CGATAACGAA | 2400

```
TGTTACGAGT  TGCAAGCTTG  AGTCGGAAGA  AATGGTGGAA  ATAATCCTGA  AAAAAGCAAA   2460

TAAATTAAGA  TCCACCGCTA  GCACAGCATC  AAATGAGCAT  TCCTCCCGTT  CACACAGTAT   2520

TTTCATAATT  CATTTGTCTG  GATCAAATGC  AAAAACTGGA  GCACACTCGT  ATGGCACACT   2580

AAATCTTGTT  GATTTGGCCG  GTTCCGAAAG  AATAAATGTC  TCTCAAGTTG  TAGGGGATAG   2640

ATTAAGAGAA  ACACAAAATA  TAAATAAATC  TTTAAGTTGC  TTAGGTGACG  TTATTCATGC   2700

TTTAGGTCAG  CCTGATAGTA  CCAAAAGACA  TATACCGTTC  AGGAACTCAA  AACTGACATA   2760

CCTACTGCAA  TATTCACTCA  CTGGGGATTC  GAAAACATTA  ATGTTTGTAA  ACATTTCACC   2820

AAGCTCCTCT  CATATTAATG  AGACTCTCAA  TTCGTTAAGA  TTTGCGTCTA  AAGTGAATTC   2880

TACCAGATTG  GTTAGTAGAA  AATGAGGTCA  AGGCCTTTTC  TGGTCTTTTT  CACTCCTTTG   2940

ACAAATGACA  GAGACTGTCC  ATACATTCAT  CACATGTAAC  TATATTATAT  ATGAAACTCA   3000

TTTTAATGCG  CACAGATAAA  AAGCAAAGTA  AGTAATGAAT  ATTTGTTATG  TAAAAATGAC   3060

CTCATACATG  CTAGTATTTA  CACGAATTTA  ATTGCTTAAA  TTTCAATCAT  CCTTACCCTT   3120

TGGTTTACCC  TCTGGAGGCA  GAAACTTTTG  CATCCTCCTT  ATTGCCCAAT  TTTCGCCAAT   3180

GACTTTAACA  TCTGGGTCCG  ATTTACCTTC  CGTGGTGTTG  AACCGCTTCC  ACCATGAGGG   3240

GGATTTGAAC  CTAGGGTCTT  CGCGTGGTAA  TTTGCGAACT  TCATTCTAA   TTTCAGCAAC   3300

ATGGGCTCTC  AGTTCAGCGG  CTAATCTGCT  TCTTAAATCT  TGCGCCTCTT  TACCATATTT   3360

CAATTCGTCA  GAGAGGTCGT  TAGGATTTTT  GGGATCATAG  TATTTTCAA   CCAAATGTGT   3420

CCATTCTTTT  CTATACCTGT  CGATTAAATC  ATCATTAAA   GGATCC                   3466
```

(2) INFORMATION FOR SEQ ID NO:39:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

```
GATAGTTAAG  GATCCATGGC  TCGTTCTTCC  TTGCCCAACC  GC                       42
```

(2) INFORMATION FOR SEQ ID NO:40:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

```
AAACTTCATC  AATGCGGCCG  CTAAGGGGAT  CCAGCCATTG  TAAAT                    45
```

(2) INFORMATION FOR SEQ ID NO:41:

(i) SEQUENCE CHARACTERISTICS:
        (A) LENGTH: 2385 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

```
GAATTCCGAT  AGTATTATGT  GGAGTTCCAT  TTTTATGTAT  TTTTTGTATG  AAATATTCTA   60
```

```
GTATAAGTAA ATATTTTATC AGAAGTATTT ACATATCTTT TTTTTTTTTA GTTTGAGAGC      120
GGCGGTGATC AGGTTCCCCT CTGCTGATTC TGGGCCCCGA ACCCCGGTAA AGGCCTCCGT      180
GTTCCGTTTC CTGCCGCCCT CCTCCGTAGC CTTGCCTAGT GTAGGAGCCC CGAGGCCTCC      240
GTCCTCTTCC CAGAGGTGTC GGGGCTTGGC CCCAGCCTCC ATCTTCGTCT CTCAGGATGG      300
CGAGTAGCAG CGGCTCCAAG GCTGAATTCA TTGTCGGAGG GAAATATAAA CTGGTACGGA      360
AGATCGGGTC TGGCTCCTTC GGGGACATCT ATTTGGCGAT CAACATCACC AACGGCGAGG      420
AAGTGGCAGT GAAGCTAGAA TCTCAGAAGG CCAGGCATCC CCAGTTGCTG TACGAGAGCA      480
AGCTCTATAA GATTCTTCAA GGTGGGGTTG GCATCCCCCA CATACGGTGG TATGGTCAGG      540
AAAAAGACTA CAATGTACTA GTCATGGATC TTCTGGGACC TAGCCTCGAA GACCTCTTCA      600
ATTTCTGTTC AAGAAGGTTC ACAATGAAAA CTGTACTTAT GTTAGCTGAC CAGATGATCA      660
GTAGAATTGA ATATGTGCAT ACAAAGAATT TTATACACAG AGACATTAAA CCAGATAACT      720
TCCTAATGGG TATTGGGCGT CACTGTAATA AGTGTTTAGA ATCCCAGTG GGGAAGAGGA       780
AAAGAAGCAT GACTGTTAGT ACTTCTCAGG ACCCATCTTT CTCAGGATTA AACCAGTTAT      840
TCCTTATTGA TTTTGGTTTG GCCAAAAAGT ACAGAGACAA CAGGACAAGG CAACACATAC      900
CATACAGAGA AGATAAAAAC CTCACTGGCA CTGCCCGATA TGCTAGCATC AATGCACATC      960
TTGGTATTGA GCAGAGTCGC CGAGATGACA TGGAATCATT AGGATATGTT TTGATGTATT     1020
TTAATAGAAC CAGCCTGCCA TGGCAAGGGC TAAAGGCTGC AACAAAGAAA CAAAAATATG     1080
AAAAGATTAG TGAAAAGAAG ATGTCCACGC CTGTTGAAGT TTTATGTAAG GGGTTTCCTG     1140
CAGAATTTGC GATGTACTTA AACTATTGTC GTGGGCTACG CTTTGAGGAA GCCCCAGATT     1200
ACATGTATCT GAGGCAGCTA TTCCGCATTC TTTTCAGGAC CCTGAACCAT CAATATGACT     1260
ACACATTTGA TTGGACAATG TTAAAGCAGA AAGCAGCACA GCAGGCAGCC TCTTCCAGTG     1320
GGCAGGGTCA GCAGGCCCAA ACCCCCACAG GCAAGCAAAC TGACAAAACC AAGAGTAACA     1380
TGAAAGGTTA GTAGCCAAGA ACCAAGTGAC GTTACAGGGA AAAAATTGAA TACAAAATTG     1440
GGTAATTCAT TTCTAACAGT GTTAGATCAA GGAGGTGGTT TTAAAATACA TAAAAATTTG     1500
GCTCTGCGTT AAAAAAAAAA AAGACGTCCT TGGAAAATTT GACTACTAAC TTTAAACCCA     1560
AATGTCCTTG TTCATATATA TGTATATGTA TTTGTATATA CATATATGTG TGTATATTTA     1620
TATCATTTCT CTTGGGATTT TGGGTCATTT TTTTAACAAC TGCATCTTTT TTACTCATTC     1680
ATTAACCCCC TTTCCAAAAA TTTGGTGTTG GGAATATAAT ATAATCAATC AATCCAAAAT     1740
CCTAGACCTA ACACTTGTTG ATTTCTAATA ATGAATTTGG TTAGCCATAT TTTGACTTTA     1800
TTTCAGACTA ACAATGTTAA GATTTTTTAT TTGCATGTT AATGCTTTAG CATTTAAAAT      1860
GGAAAATTGT GAACATGTTG TAATTTCAAG AGGTGAGTTT GGCATTACCC CCAAAGTGTC     1920
TATCTTCTCA GTTGCAGAGC ATCTCATTTT CTCTCTTAAA TGCTCAAATA AATGCAAAGC     1980
TCAGCACATC TTTTCTAGTC ACAAAAATAA TTCTTTTATT TGCAGTTTAC GTATGATCTT     2040
AATTTCAAAA CGATTTCTTT GTTTTGGCT TGATTTTCA CAATGTTGCA AATATCAGGC       2100
TCCCAGGGTT TAATGTGGAA TTGAAGTCTG CAGCCAGGCC TTGCAAATTG AAGGTAACTG     2160
GGGCAAATGC CATTGAAACC GCTAGTCTTA TTTCCTTTCT ACTTTTCTTT GGCACTCTTA     2220
CTGCCTGTAA GGAGTAGAAC TGTTAAGGCA CACTGTTGCT ATACAGTTAA CTCCCATTTT     2280
CATGTTTTGT CTTTCTTTTC CCATTCTGG GGCTTACCTC CTGATACCTG CTTACTTTCT     2340
GGAAGTAGTG GGCAAGTAAG ATTTGGCTCT TGGTTTCTGG AATTC                     2385
```

( 2 ) INFORMATION FOR SEQ ID NO:42:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

| | | | |
|---|---|---|---|
| CTTCGTCTCT | CACATATGGG | CGAGTAGCAG | CGGC | 34 |

( 2 ) INFORMATION FOR SEQ ID NO:43:

( i ) SEQUENCE CHARACTERISTICS:
        ( A ) LENGTH: 3505 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

| | | | | | | |
|---|---|---|---|---|---|---|
| GAATTCCGAC | AGGAAAGCGA | TGGTGAAAGC | GGGGCCGTGA | GGGGGGCGGA | GCCGGGAGCC | 60 |
| GGACCCGCAG | TAGCGGCAGC | AGCGGCGCCG | CCTCCCGGAG | TTCAGACCCA | GGAAGCGGCC | 120 |
| GGGAGGGCAG | GAGCGAATCG | GGCCGCCGCC | GCCATGGAGC | TGAGAGTCGG | GAACAGGTAC | 180 |
| CGGCTGGGCC | GGAAGATCGG | CAGCGGCTCC | TTCGGAGACA | TCTATCTCGG | TACGGACATT | 240 |
| GCTGCAGGAG | AAGAGGTTGC | CATCAAGCTT | GAATGTGTCA | AAACCAAACA | CCCTCAGCTC | 300 |
| CACATTGAGA | GCAAAATCTA | CAAGATGATG | CAGGGAGGAG | TGGGCATCCC | CACCATCAGA | 360 |
| TGGTGCGGGG | CAGAGGGGGA | CTACAACGTC | ATGGTGATGG | AGCTGCTGGG | GCCAAGCCTG | 420 |
| GAGGACCTCT | TCAACTTCTG | CTCCAGGAAA | TTCAGCCTCA | AAACCGTCCT | GCTGCTTGCT | 480 |
| GACCAAATGA | TCAGTCGCAT | CGAATACATT | CATTCAAAGA | ACTTCATCCA | CCGGGATGTG | 540 |
| AAGCCAGACA | ACTTCCTCAT | GGGCCTGGGG | AAGAAGGGCA | ACCTGGTGTA | CATCATCGAC | 600 |
| TTCGGGCTGG | CCAAGAAGTA | CCGGGATGCA | CGCACCCACC | AGCACATCCC | CTATCGTGAG | 660 |
| AACAAGAACC | TCACGGGGAC | GGCGCGGTAC | GCCTCCATCA | ACACGCACCT | TGGAATTGAA | 720 |
| CAATCCCGAA | GAGATGACTT | GGAGTCTCTG | GGCTACGTGC | TAATGTACTT | CAACCTGGGC | 780 |
| TCTCTCCCCT | GGCAGGGGCT | GAAGGCTGCC | ACCAAGAGAC | AGAAATACGA | AAGGATTAGC | 840 |
| GAGAAGAAAA | TGTCCACCCC | CATCGAAGTG | TTGTGTAAAG | GCTACCCTTC | CGAATTTGCC | 900 |
| ACATACCTGA | ATTTCTGCCG | TTCCTTGCGT | TTTGACGACA | AGCCTGACTA | CTCGTACCTG | 960 |
| CGGCAGCTTT | TCCGGAATCT | GTTCCATCGC | CAGGGCTTCT | CCTATGACTA | CGTGTTCGAC | 1020 |
| TGGAACATGC | TCAAATTTGG | TGCCAGCCGG | GCCGCCGATG | ACGCCGAGCG | GGAGCGCAGG | 1080 |
| GACCGAGAGG | AGCGGCTGAG | ACACTCGCGG | AACCCGGCTA | CCCGCGGCCT | CCCTTCCACA | 1140 |
| GCCTCCGGCC | GCCTGCGGGG | GACGCAGGAA | GTGGCTCCCC | CCACACCCCT | CACCCCTACC | 1200 |
| TCACACACGG | CTAACACCTC | CCCCGGCCC | GTCTCCGGCA | TGGAGAGAGA | GCGGAAAGTG | 1260 |
| AGTATGCGGC | TGCACCGCGG | GGCCCCCGTC | AACATCTCCT | CGTCCGACCT | CACAGGCCGA | 1320 |
| CAAGATACCT | CTCGCATGTC | CACCTCACAG | ATTCCTGGTC | GGGTGGCTTC | CAGTGGTCTT | 1380 |
| CAGTCTGTCG | TGCACCGATG | AGAACTCTCC | TTATTGCTGT | GAAGGGCAGA | CAATGCATGG | 1440 |
| CTGATCTACT | CTGTTACCAA | TGGCTTTACT | AGTGACACGT | CCCCCGGTCT | AGGATCGAAA | 1500 |
| TGTTAACACC | GGGAGCTCTC | CAGGCCACTC | ACCCAGCGAC | GCTCGTGGGG | GAAACATACT | 1560 |
| AAACGGACAG | ACTCCAAGAG | CTGCCACCGC | TGGGGCTGCA | CTGCGGCCCC | CCACGTGAAC | 1620 |

| | | | | | |
|---|---|---|---|---|---|
| TCGGTTGTAA | CGGGGCTGGG | AAGAAAAGCA | GAGAGAGAAT | TGCAGAGAAT | CAGACTCCTT | 1680 |
| TTCCAGGGCC | TCAGCTCCCT | CCAGTGGTGG | CCGCCCTGTA | CTCCCTGACG | ATTCCACTGT | 1740 |
| AACTACCAAT | CTTCTACTTG | GTTAAGACAG | TTTTGTATCA | TTTTGCTAAA | AATTATTGGC | 1800 |
| TTAAATCTGT | GTAAGAAAA | TCTGTCTTTT | TATTGTTTCT | TGTCTGTTTT | TGCGGTCTTA | 1860 |
| CAAAAAAAT | GTTGACTAAG | GAATTCTGAG | ACAGGCTGGC | TTGGAGTTAG | TGTATGAGGT | 1920 |
| GGAGTCGGGC | AGGGAGAAGG | TGCAGGTGGA | TCTCAAGGGT | GTGTGCTGTG | TTTGTTTTGC | 1980 |
| AGTGTTTTAT | TGTCCGCTTT | GGAGAGGAGA | TTTCTCATCA | AAAGTCCGTG | GTGTGTGTGT | 2040 |
| GTGCCCGTGT | GTGGTGGGAC | CTCTTCAACC | TGATTTTGGC | GTCTCACCCT | CCCTCCTCCC | 2100 |
| GTAATTGACA | TGCCTGCTGT | CAGGAACTCT | TGAGGCCCTC | GGAGAGCAGT | TAGGGACCGC | 2160 |
| AGGCTGCCGC | GGGGCAGGGG | TGCAGTGGGT | GTTACCAGGC | AAAGCACTGC | GCGCTTCTTC | 2220 |
| CCCAGGAGGT | GGGCAGGCAG | CTGAGAGCTT | GGAAGCAGAG | GCTTTGAGAC | CCTAGCAGGA | 2280 |
| CAATTGGGAG | TCCCAGGATT | CAAGGTGGAA | GATGCGTTTC | TGGTCCCTTG | GGAGAGGACT | 2340 |
| GTGAACCGAG | AGGTGGTTAC | TGTAGTGTTT | GTTGCCTTGC | TGCCTTTGCA | CTCAGTCCAT | 2400 |
| TTTCTCAGCA | CTCAATGCTC | CTGTGCGGAT | TGGCACTCCG | TCTGTATGAA | TGCCTGTGGT | 2460 |
| TAAAACCAGG | AGCGGGGCTG | TCCTTGCCAC | GTGCCAAGAC | TAGCTCAGAA | AAGCCGGCAG | 2520 |
| GCCAGAAGGA | CCCACCCTGA | GGTGCCAAGG | AGCAGGTGAC | TCTCCCAACC | GGACCCAGAA | 2580 |
| CCTTCACGGC | CAGAAAGTAG | AGTCTGCGCT | GTGACTTCT | GTTGGGCGCG | TGTCTGTTGG | 2640 |
| TCAGAAGTGA | AGCAGCGTGC | GTGGGGCCGA | GTCCCACCAG | AAGGCAGGTG | GCCTCCGTGA | 2700 |
| GCTGGTGCTG | CCCCAGGCTC | CATGCTGCTG | TGCCCTGAGG | TTCCCAGGAT | GCCTTCTCGC | 2760 |
| CTCTCACTCC | GCAGCACTTG | GGCGGTAGCC | AGTGGCCATG | TGCTCCCAAC | CCCAATGCGC | 2820 |
| AGGGCAGTCT | GTGTTCGTGG | GCACTTCGGC | TGGACCCCAT | CACGATGGAC | GATGTTCCCT | 2880 |
| TTGGACTCTA | GGGCTTCGAA | GGTGTGCACC | TTGGTTCTCC | CTTCTCCTCC | CCAGAGTTCC | 2940 |
| CCCGGATGCC | ATAACTGGCT | GGCGTCCAG | AACACAGTTG | TCAACCCCCC | CACCAGCTGG | 3000 |
| CTGGCCGTCT | GTCTGAGCCC | ATGGATGCTT | TCTCAATCCT | AGGCTGGTTA | CTGTGTAAGC | 3060 |
| GTGTTGGAGT | ACGGCGCCTT | GAGCGGGTGG | GAGCTGTGTG | TTGAAGTACA | GAGGGAGGTT | 3120 |
| GGGGTGGGTC | AGAGCCGAGT | TAAGAGATTT | TCTTTGTTGC | TGGACCCCTT | CTTGAAGGTA | 3180 |
| GACGTCCCCC | ACCCGGAGAG | ACGTCGCGCT | GTGGCCTGAA | GTGGCGCAAG | CTTGCTTTGT | 3240 |
| AAATATCTGT | GGTCCCGATG | TAGTGCCCAG | AACGTTTGTG | CGAGGCAGCT | CTGCGCCCGG | 3300 |
| GTTCCAGCCC | GAGCCTCGCC | GGGTCGCGTC | TTCGGAGTGC | TTGTGACAGT | CCTTGCCCAG | 3360 |
| TATCTAGTCC | CCGTCGCCCC | GTGCAGGAGA | CGTAGGTAGG | ACGTCGTGTC | AGCTGTGCAC | 3420 |
| TGACGGCCAG | TCTCCGAGCT | GTGCGTTTGT | ATCGCCACTG | TATTTGTGTA | CTTAACAAT | 3480 |
| CGTGTAAATA | ATAAATTCGG | AATTC | | | | 3505 |

( 2 ) INFORMATION FOR SEQ ID NO:44:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGCGGATCCT AATGGAGGTG AGAGTCGGG                               29

( 2 ) INFORMATION FOR SEQ ID NO:45:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:45:

CGCGGATCCG CTCATCGGTG CACGACAGA 29

( 2 ) INFORMATION FOR SEQ ID NO:46:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:46:

GGAATCACTA CAGGGATG 18

( 2 ) INFORMATION FOR SEQ ID NO:47:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:47:

ATTCTAGACA TGGAGACCAG TTCTTTTGAG 30

( 2 ) INFORMATION FOR SEQ ID NO:48:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:48:

TGGAAGCTTA TATTACCATA GATTCTTCTT G 31

( 2 ) INFORMATION FOR SEQ ID NO:49:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:49:

Ser Leu Ser Phe Pro Arg Gly Lys Ile Ser Lys Asp Glu Asn Asp Ile
 1               5                  10                  15

Asp Cys Cys Ile Arg Glu Val Lys Glu Glu Ile Gly Phe Asp Leu Thr
            20                  25                  30

Asp ( 2 ) INFORMATION FOR SEQ ID NO:50:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

```
Arg Trp Asn Gly Phe Gly Gly Tyr Val Gln Glu Gly Glu Thr Ile Glu
 1               5                  10                      15
Asp Gly Ala Arg Arg Glu Leu Gln Glu Ser Gly Leu Thr Val Asp
             20                  25                  30
Ala
```

( 2 ) INFORMATION FOR SEQ ID NO:51:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Lys Leu Glu Phe Pro Gly Gly Lys Ile Glu Met Gly Glu Thr Arg Glu
 1               5                  10                      15
Gln Ala Val Val Arg Glu Leu Gln Glu Val Gly Ile Thr Pro Gln
             20                  25                  30
His
```

( 2 ) INFORMATION FOR SEQ ID NO:52:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:52:

```
Asp Ile Ile Phe Pro Gly Gly Leu Pro Lys Asn Glu Glu Asp Pro Ile
 1               5                  10                      15
Met Cys Leu Ser Arg Glu Ile Lys Glu Glu Ile Asn Ile Asp Ser Lys
             20                  25                  30
Asp
```

( 2 ) INFORMATION FOR SEQ ID NO:53:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Asp Ile Ile Phe Pro Gly Gly Leu Pro Lys Asn Glu Glu Asp Pro Ile
 1               5                  10                      15
Met Cys Leu Ser Arg Glu Ile Lys Glu Glu Ile Asn Ile Asp Ser Lys
             20                  25                  30
Asp
```

MATERIALS AND METHODS RELATING TO PROTEINS THAT INTERACT WITH CASEIN KINASE I

This application is a continuation-in-part of U.S. patent application Ser. No.08/184,605, filed Jan. 21, 1994, now abandonded.

FIELD OF THE INVENTION

The present invention relates generally to identification of proteins, herein designated TIH proteins, that interact with casein kinase I isoforms and to isolation of polynucleotides encoding the same.

BACKGROUND

Protein kinases are post-translational, enzymatic regulators of cellular metabolism. Once activated, these enzymes transfer phosphate from ATP onto substrate proteins and in doing so affect the properties of substrate molecules. There are four broad classes of protein kinases including serine/threonine kinases, tyrosine kinases, multi-specific or dual-specific kinases, and histidine kinases [Hunter, et al., *Meth. Enzymol.* 200:3–37 (1991)]. In addition to the amino acid residue(s) of the substrate preferentially phosphorylated by the kinase, assignment of an enzyme to a particular class is based on its primary structure, its requirement for regulatory subunits, its requirement for second messengers, and its specific biochemical activity. See Hunter et al., supra, and Hanks and Quinn, *Meth. Enzymol.*, 200: 38–62 (1991).

Serine/threonine protein kinases have been further divided into families of enzymes based on the mode of regulation of the enzymes and the quaternary structure of the active enzymes [Edelman, et al., *Ann.Rev. Biochem.* 56:567–613 (1987)]. Enzymes within the serine/threonine protein kinase family can differ in the substrates they phosphorylate, the specific phosphorylation sites they recognize, their mode of regulation and their subcellular distribution. Protein kinase A (PKA), for example, phosphorylates target substrates with the recognition/phosphorylation sequence R-R-X-S(P)-Y (SEQ ID NO: 1) [Pearson and Lemp, *Meth.Enzymol.* 200:62–81 (1991)], where S(P) represents the phosphorylated residue. The activity of PKA is localized by targeting subunits (called anchoring proteins or AKAPs, reviewed in Hubbard and Cohen, *T.I.B.S.* 18:172–177, 1993). Members of the casein kinase I (CKI) family, on the other hand, recognize and phosphorylate serines and threonines near acidic residues in substrate proteins. The genes which encode yeast, rat, bovine and human isoforms of casein kinase I activity are structurally similar and the isoforms exhibit greater than 35%, and frequently greater than 50%, homology (identity) over their catalytic domains when compared to the prototypical *S. cerevisiae* CKI protein, HRR25, and are referred to herein as "HRR25-like" proteins. This degree of identity is significantly greater than the expected 25% found for comparing two randomly chosen protein kinases [Hanks and Quinn, supra]. The HRR25 DNA sequence is disclosed in Hoekstra, et al., *Science* 253:1031–1034 (1991); yeast CKI1 and CKI2 DNA sequences in Wang et al., *J. Mol. Biol. Cell*, 3:275–286 (1992) corresponding respectively to yeast sequences YCK2 and YCK1 in Robinson et al., *Proc. Natl. Acad. Sci.* (USA) 89:28–32 (1992); partial bovine CKIα, CKIβ, CKIγ and CKIδ DNA sequences and a full length homolog CKIα DNA sequence in Rowles, et al., *Proc. Natl. Acad. Sci.* (USA) 88:9548–9552 (1991); a full length rat CKIδ DNA sequence in Graves, et al., *J. Biol. Chem.*, 268: 6394–6401 (1993); and a partial human erythroid CKIα DNA sequence in Brockman et al., *Proc. Natl. Acad. Sci.* (USA) 89:9454–9458 (1992).

The *S. cerevisiae* protein kinase HRR25 is one of the more extensively characterized isoforms of the CKI family [Hoekstra, supra]. Mutations in the HRR25 gene result in a variety of defects that include cell cycle delays, the inability to properly repair DNA strand breaks and characteristic morphological changes. The nature of these defects implies that HRR25 and other CKI isoforms play a significant role in cellular growth.

The importance of protein phosphorylation and protein kinases in health and disease states is evident in cases where expression of a particular kinase has gone awry; for example, chronic myelogenous leukemia arises from a translocation that places the breakpoint cluster region (BCR) gene next to the ABL tyrosine kinase gene, resulting in a fusion protein comprising the activated protein kinase [see review, Bishop, et al., *Cell* 64:235–288 (1991)]. In addition, many oncogenes, such as Mos [Watson, et al., *Proc.Nat.l.Acad.Sci.* (USA) 79:4078–4082 (1982)], Src [Anderson, et al., *Mol. Cell. Biol.* 5:1122–1129 (1985)] and Raf [Bonner, et al., *Nucl.Acids Res.* 14:1009–1015 (1986)] are protein kinases.

Most protein kinases phosphorylate a variety of substrates in vivo allowing diversity in responses to physiological stimuli [reviewed in Edelman, et al., supra]. However, the broader substrate specificity seen for many protein kinases in vitro, including activity towards non-physiological substrates, indicates that cellular mechanisms to control the specificity of these enzymes must exist in vivo. Understanding the regulatory mechanisms that govern these kinases and the specific role of the kinases in health and disease states requires the identification of substrates, regulatory proteins, and localizing/targeting proteins that interact with the kinases.

There thus exists a need in the art to identify proteins which interact with members of the casein kinase I family of enzymes and to characterize the interacting proteins in terms of their amino acid and encoding DNA sequences. Such information would provide for the large scale production of the proteins, allow for identification of cells which produce the kinases naturally and permit production of antibodies specifically reactive with the kinases. Moreover, elucidation of the substrates, regulation, and localization of these protein kinases would contribute to an understanding of the control of normal and malignant cell growth and provide information essential for the development of therapeutic agents useful for intervention in abnormal and/or malignant cell growth.

SUMMARY OF THE INVENTION

In one of its aspects, the present invention provides methods for identifying proteins, designated TIH proteins, that interact with CKI isoforms [i.e., *S. cerevisiae* HRR25 casein kinase I and HRR25-like protein kinases having at least 35 % amino acid homology to HRR25 within the catalytic domain] and for isolating polynucleotides encoding the TIH proteins. A presently preferred method comprises the steps of: a) transforming or transfecting appropriate host cells with a DNA construct comprising a reporter gene under the control of a promoter regulated by a transcription factor having a DNA-binding domain and an activating domain; b) expressing in the host cells a first hybrid DNA sequence encoding a first fusion of part or all of a CKI isoform and either the DNA-binding domain or the activating domain of the transcription factor; c) expressing in the host cells a library of second hybrid DNA sequences encoding second fusions of part or all of putative CKI isoform-binding proteins and either the DNA-binding domain or DNA activating domain of the transcription factor which is not incorporated in the first fusion; d) detecting binding of CKI isoform-binding proteins to the CKI isoform in a particular host cell by detecting the production of reporter gene product in the host cell; and e) isolating second hybrid DNA sequences encoding CKI isoform-binding protein from the particular host cell. Variations of the method altering the order in which the CKI isoforms and putative CKI isoform-binding proteins are fused to transcription factor domains, i.e., at the amino terminal or carboxy terminal ends of the transcription factor domains, are contemplated. In a preferred version of the method, the promoter is the lexA promoter, the DNA-binding domain is the lexA DNA-binding domain, the activating domain is the GAL4 trans-activation domain, the reporter gene is the lacZ gene and the host cell is a yeast host cell.

Variations of the method permit identification of either small molecules which inhibit the interaction between a CKI isoform and a CKI-interacting protein. A preferred method to identify small molecule inhibitors comprises the steps of: a) transforming or transfecting appropriate host cells with a DNA construct comprising a reporter gene under the control of a promoter regulated by a transcription factor having a DNA-binding domain and an activating domain; b) expressing in the host cells a first hybrid DNA sequence encoding a first fusion of part or all of a CKI isoform and either the DNA-binding domain or the activating domain of the transcription factor; c) expressing in the host cells a second hybrid DNA sequence encoding second fusion of part or all of a known CKI isoform-binding protein and either the DNA-binding domain or DNA activating domain of the transcription factor which is not incorporated in the first fusion; d) contacting the cells with a putative inhibitor compound; and e) identifying modulating compounds as those compounds altering production of the reporter gene product in comparison to production of the reporter gene product in the absence of the modulating compound.

An alternative identification method contemplated by the invention for detecting proteins which bind to a CKI isoform comprises the steps of: a) transforming or transfecting appropriate host cells with a hybrid DNA sequence encoding a fusion between a putative CKI isoform-binding protein and a ligand capable of high affinity binding to a specific counterreceptor; b) expressing the hybrid DNA sequence in the host cells under appropriate conditions; c) immobilizing fusion protein expressed by the host cells by exposing the fusion protein to the specific counterreceptor in immobilized form; d) contacting a CKI isoform with the immobilized fusion protein; and e) detecting the CKI isoform bound to the fusion protein using a reagent specific for the CKI isoform. Presently preferred ligands/counterreceptor combinations for practice of the method are glutathione-S-transferase/glutathione, hemagglutinin/hemagglutinin-specific antibody, polyhistidine/nickel and maltose-binding protein/amylose.

The present invention also provides novel, purified and isolated polynucleotides (e.g., DNA sequences and RNA transcripts, both sense and antisense strands) encoding the TIH proteins and variants thereof (i.e., deletion, addition or substitution analogs) which possess CKI and/or HRR25-binding properties inherent to the TIH proteins. Preferred DNA molecules of the invention include cDNA, genomic DNA and wholly or partially chemically synthesized DNA molecules. Presently preferred polynucleotides are the DNA molecules set forth in SEQ ID NOS: 2 (TIH1), 4 (TIH2), and 6 (TIH3), encoding the polypeptides of SEQ ID NOS: 3 (TIH1), 5 (TIH2), and 7 (TIH3), respectively. Also provided are recombinant plasmid and viral DNA constructs (expression constructs) which comprise TIH polypeptide-encoding sequences operatively linked to a homologous or heterologous transcriptional regulatory element or elements.

As another aspect of the invention, prokaryotic or eukaryotic host cells transformed or transfected with DNA sequences of the invention are provided which express TIH polypeptides or variants thereof. Host cells of the invention are particularly useful for large scale production of TIH polypeptides, which can be isolated from the host cells or the medium in which the host cells are grown.

Also provided by the present invention are purified and isolated TIH polypeptides, fragments and variants thereof. Preferred TIH polypeptides are as set forth in SEQ ID NOS: 3 (TIH1), 5 (TIH2), and 7 (TIH3). Novel TIH and TIH variant products of the invention may be obtained as isolates from natural sources, but are preferably produced by recombinant procedures involving host cells of the invention. Post-translational processing variants of TIH polypeptides may be generated by varying the host cell selected for recombinant production and/or post-isolation processing. Variant TIH polypeptides of the invention may comprise analogs wherein one or more of the amino acids are deleted or replaced: (1) without loss, and preferably with enhancement, of biological properties or biochemical characteristics specific for TIH polypeptides or (2) with specific disablement of a characteristic protein/protein interaction.

Also comprehended by the invention are antibody substances (e.g., monoclonal and polyclonal antibodies, single chain antibodies, chimeric antibodies, CDR-grafted antibodies and the like) which are specifically immunoreactive with TIH polypeptides. Antibody substances are useful, for example, for purification of TIH polypeptides and for isolation, via immunological expression screening, of homologous and heterologous species polynucleotides encoding TIH polypeptides. Hybridoma cell lines which produce antibodies specific for TIH polypeptides are also comprehended by the invention. Techniques for producing hybridomas which secrete monoclonal antibodies are well known in the art. Hybridoma cell lines may be generated after immunizing an animal with purified TIH polypeptides or variants thereof.

The scientific value of the information contributed through the disclosure of DNA and amino acids sequences of the present invention is manifest. As one series of examples, knowledge of the genomic DNA sequences which encode yeast TIH polypeptides permits the screening of a cDNA or genomic DNA of other species to detect homologs of the yeast polypeptides. Screening procedures, including DNA/DNA and/or DNA/RNA hybridization and PCR amplification are standard in the art and may be utilized to isolate heterologous species counterparts of the yeast TIH polypeptides, as well as to determine cell types which express these homologs.

DNA and amino acid sequences of the invention also make possible the analysis of TIH epitopes which actively participate in kinase/protein interactions as well as epitopes which may regulate such interactions. Development of agents specific for these epitopes (e.g., antibodies, peptides or small molecules) which prevent, inhibit, or mimic protein kinase-protein substrate interaction, protein kinase-regulatory subunit interaction, and/or protein kinase-protein localization molecule interaction are contemplated by the invention. Therapeutic compositions comprising the agents are expected to be useful in modulating the CKI/TIH protein interactions involved in cell growth in health and disease states, for example, cancer and virus-related pathologies.

BRIEF DESCRIPTION OF THE DRAWING

Numerous other aspects and advantages of the present invention will be apparent upon consideration of the following detailed description thereof, reference being made to the drawing wherein:

FIG. 2 is an amino acid sequence comparison between TIH1 and enzymes known to participate in removal of aberrant nucleotides.

DETAILED DESCRIPTION

Figure 1:
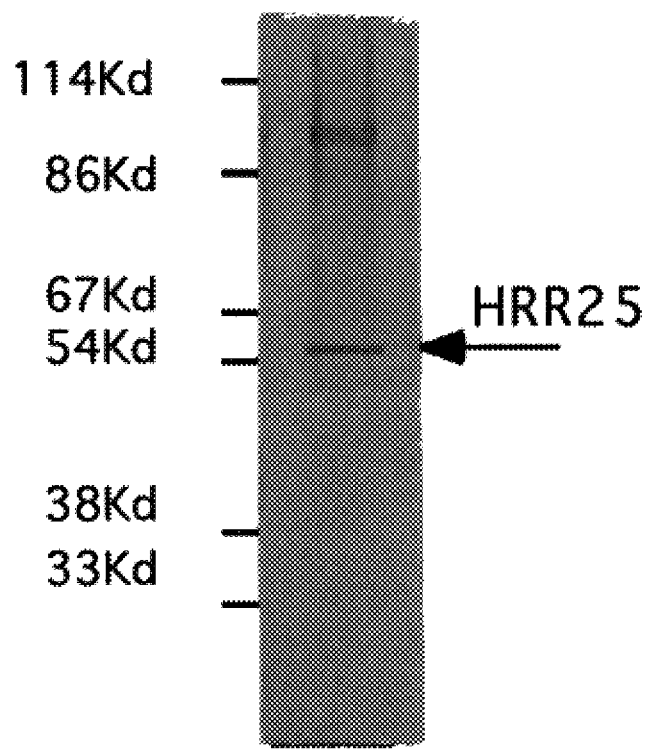
FIG. 1 is a Western blot demonstrating the association of S. cerevisiae HRR25 casein kinase I with affinity-purified TIH2.

The present invention generally relates to methods for identifying proteins that interact with CKI isoforms and is illustrated by the following examples relating to the isolation and characterization of genes encoding TIH polypeptides. More particularly, Example 1 addresses isolation of DNA sequences encoding TIH polypeptides from a yeast genomic library utilizing a dihybrid screening technique. Example 2 relates to analysis of the interaction between TIH polypeptides and various yeast CKI isoforms. Example 3 addresses interaction between a yeast CKI isoform, including mutants and fragments thereof, and kinesins. Example 4 describes analysis of the interaction between TIH polypeptides and human CKI isoforms. Example 5 addresses isolation of full length genomic DNA sequences which encode TIH polypeptides of the invention. Example 6 describes construction of a TIH knock-out mutant in yeast. Example 7 addresses analysis of S. cerevisiae HRR25/TIH polypeptides interactions utilizing affinity purification and Western blotting techniques. Example 8 provides a comparison at the amino acid level between TIH1 and enzymes identified as participating in degradation of oxidatively damaged nucleotides, thus enhancing fidelity of replication.

EXAMPLE 1

Cellular components that interact with CKI isoforms were identified by a dihybrid screening method that reconstitutes a transcriptional transactivator in yeast. [A similar "two-hybrid" assay was originally described in Fields and Song, *Nature*, 340: 245–246 (1989) and more recently in Yang et al., *Science* 257:681–682 (1992) and Vojtek et al., *Cell*, 74: 205–214 (1993).] In the assay, "bait" components (i.e., CKI isoforms) are fused to the DNA binding domain of a transcription factor (e.g., the lexA protein) and "prey" components (i.e., putative CKI interacting proteins) are fused to the transactivation domain of the transcription factor (e.g., GAL4). Recombinant DNA constructs encoding the fusion proteins are expressed in a host cell that contains a reporter gene fused to promoter regulatory elements (e.g. a lexA DNA binding site) recognized by the transcription factor. Binding of a prey fusion protein to a bait fusion protein brings together the GAL4 transactivation domain and the lexA DNA binding domain allowing interaction of the complex with the lexA DNA binding site that is located next to the β-galactosidase reporter gene, thus reconstituting transcriptional transactivation and producing β-galactosidase activity. In variations of the method, the "prey" component can be fused to the DNA binding domain of GAL4 and the "bait" components detected and analyzed by fusion to the transactivation domain of GAL4. Likewise, variations of this method could alter the order in which "bait" and "prey" components are fused to transcription factor domains, i.e., "bait" and "prey" components can be fused at the amino terminal or carboxy terminal ends of the transcription factor domains.

To identify genes encoding proteins that interact with S. cerevisiae HRR25 CKI protein kinase, a plasmid library encoding fusions between the yeast GAL4 activation domain and S. cerevisiae genomic fragments ("prey" components) was screened for interaction with a DNA binding domain hybrid that contained the E. coli lexA gene fused to HRR25 ("bait" component). The fusions were constructed in plasmid pBTM116 (gift from Bartell and Fields, SUNY) which contains the yeast TRP1 gene, a 2μ origin of replication, and a yeast ADHI promoter driving expression of the E. coli lexA DNA binding domain (amino acids 1 to 202).

Plasmid pBTM116::HRR25, which contains the lex-A::HRR25 fusion gene, was constructed in several steps. The DNA sequence encoding the initiating methionine and second amino acid of HRR25 was changed to a SmaI restriction site by site-directed mutagenesis using a MutaGene mutagenesis kit from BioRad (Richmond, Calif.). The DNA sequence of HRR25 is set out in SEQ ID NO: 8. The oligonucleotide used for the mutagenesis is set forth below, wherein the SmaI site is underlined.

5'-CCT ACT CTT AGG <u>CCC GGG</u> TCT TTT TAA TGT ATC C-3'
(SEQ ID NO. 9)

After digestion with SmaI, the resulting altered HRR25 gene was ligated into plasmid pBTM116 at the SmaI site to create the lexA::HRR25 fusion construct.

Interactions between bait and prey fusion proteins were detected in yeast reporter strain CTY10-5d (genotype= MATa ade2 trpl-901 leu2-3,112 his 3-200 gal4 gal80 URA3::lexA op-lacZ.) [Luban, et al., *Cell* 73:1067–1078 (1993)] carrying a lexA binding site that directs transcription of lacZ. Strain CTY10-5d was first transformed with plasmid pBTM116::HRR25 by lithium acetate-mediated transformation [Ito, et al., *J.Bacteriol.* 153:163–168 (1983)]. The resulting transformants were then transformed with a prey yeast genomic library prepared as GAL4 fusions in the plasmid pGAD [Chien, et al., *Proc.Natl.Acad.Sci* (USA) 21:9578–9582 (1991)] in order to screen the expressed proteins from the library for interaction with HRR25. A total of 500,000 double transformants were assayed for β-galactosidase expression by replica plating onto nitrocellulose filters, lysing the replicated colonies by quick-freezing the filters in liquid nitrogen, and incubating the lysed colonies with the blue chromogenic substrate 5-bromo-4-chloro-3-indolyl-β-D-galactoside (X-gal). β-galactosidase activity was measured using Z buffer (0.06M $Na_2HPO_4$, 0.04M $NaH_2PO_4$, 0.01M KC1, 0.001M $MgSO_4$, 0.05M β-mercaptoethanol) containing X-gal at a concentration of 0.002% [Guarente, *Meth. Enzymol.* 101:181–191 (1983)]. Reactions were terminated by floating the filters on 1M $Na_2CO_3$ and positive colonies were identified by their dark blue color.

Library fusion plasmids (prey constructs) that conferred blue color to the reporter strain co-dependent upon the presence of the HRR25/DNA binding domain fusion protein partner (bait construct) were identified. The sequence adjacent to the fusion site in each library plasmid was determined by extending DNA sequence from the GAL4 region. The sequencing primer utilized is set forth below.

5'-GGA ATC ACT ACA GGG ATG-3' (SEQ ID NO. 10) DNA sequence was obtained using a Sequenase version II kit (US Biochemicals, Cleveland, Ohio) or by automated DNA sequencing with an ABI373A sequencer (Applied Biosystems, Foster City, Calif.).

Four library clones were identified and the proteins they encoded are designated herein as TIH proteins 1 through 4 for Targets Interacting with HRR25-like protein kinase isoforms. The TIH1 portion of the TIH1 clone insert corresponds to nucleotides 1528 to 2580 of SEQ ID NO: 2; the TIH2 portion of the TIH2 clone insert corresponds to nucleotides 2611 to 4053 of SEQ ID NO: 4; the TIH3 portion of the TIH3 clone insert corresponds to nucleotides 248 to 696 of SEQ ID NO: 6; and the TIH4 portion of the TIH4 clone insert is set out in SEQ ID NO: 11 and corresponds to nucleotides 1763 to 2305 of SEQ ID NO: 28. Based on DNA sequence analysis of the TIH genes, it was determined that TIH1 and TIH3 were novel sequences that were not representative of any protein motif present in the GenBank database (Jul. 8, 1993). TIH2 sequences were identified in the database as similar to a yeast open reading frame having no identified function. (GenBank Accession No. Z23261, open reading frame YBL0506) TIH4 represented a fusion protein between GAL4 and the carboxy-terminal portion of the kinesin-like protein KIP2. KIP2 has a highly conserved region which contains a kinesin-like microtubule-based motor domain [Roof et al., *J. Cell. Biol.* 118(1):95–108 (1992)]. The isolation of corresponding full length genomic clones for TIH1 through TIH3 is described in Example 5.

EXAMPLE 2

To investigate the specificity of interaction and regions of interaction between CKI isoforms and the TIH proteins, bait constructs comprising mutant or fragment HRR25 isoforms or other yeast (NUF1 and Hhp1) CKI isoforms fused to the lexA DNA binding domain were examined for transcription transactivation potential in the dihybrid assay.

Plasmid Constructions

To construct a plasmid containing a catalytically-inactive HRR25 protein kinase, HRR25 DNA encoding a lysine to arginine mutation at residue 38 (the ATP binding site) of HRR25 [DeMaggio et al., *Proc. Natl. Acad. Sci.* (USA) 89(15): 7008–7012 (1992)] was generated by standard site-directed mutagenesis techniques. The resulting DNA was then amplified by a PCR reaction which inserted a SmaI restriction site (underlined in SEQ ID NO. 12) before the HRR25 ATG using a mutagenic oligonucleotide:
5'-CCT TCC TAC TCT TAA GCC CGG GCC GCA GGA ATT CG-3'
(SEQ ID NO 12),
and the downstream oligonucleotide which inserted a BamHI site (underlined): 5'-AGC AAT ATA GGA TCC TTA CAA CCA AAT TGA-3' (SEQ ID NO: 13). Reactions included 200 mM Tris-Hcl (pH 8.2), 100 mM KCl, 60 mM (NH$_4$)$_2$SO$_4$, 15 mM MgCl$_2$, 1% Triton X-100, 0.5 µM primer, 100 ng template, 200 µM dNTP and 2.5 units polymerase. The reactions were performed for 30 cycles. Reactions were started with a 4 minute treatment at 94° C. and all cycles were 1 minute at 94° C. for denaturing, 2 minutes at 50° C. for annealing, and 4 minutes at 72° C. for extension. The resulting amplification product was digested with SmaI and ligated at the SmaI site of pBTM116 to produce the plasmid designated pBTM116::HRR25K→R encoding lexA sequences fused 5' to HRR25 sequences.

To construct a pBTM116 plasmid encoding a catalytic domain fragment of HRR25, two rounds of site-directed mutagenesis were performed to introduce a SmaI site in place of the initiating ATG and second codon of HRR25 DNA and a BamHI site at nucleotide 1161 (refer to SEQ ID NO. 8) or amino acid 397 of HRR25. The mutagenic oligonucleotide used to introduce the 5' SmaI restriction site (underlined) was:
5'-CCT ACT CTT AAG CCC GGG TCT TTT TAA TGT ATC C-3'
(SEQ ID NO. 14),
and the oligonucleotide used to create the 3', or downstream, BamHI site (underlined) at residue 397 was:
5'-GTC TCA AGT TTT GGG ATC CTT AAT CTA GTG CG-3'
(SEQ ID NO. 15).

The resulting product was digested with SmaI-BamHI and the fragment encoding the HRR25 catalytic domain (corresponding to nucleotides 2 to 1168 of SEQ ID NO: 8) was subcloned into plasmid pBTM116 linearized with the same enzymes to produce the plasmid designated pBTM116::Kinase domain encoding lexA sequences fused 5' to HRR25 sequences.

To construct a pBTM116 plasmid containing the non-catalytic domain fragment of HRR25, a SmaI site (underlined) was introduced at nucleotide 885 (amino acid 295) using site-directed mutagenesis with the following oligonucleotide:
5'-CAC CAT CGC CCC CGG GTA ACG CAA CAT TGT CC-3'
(SEQ ID NO: 16).

The resulting product was digested with SmaI and BamHI and the fragment encoding the HRR25 non-catalytic domain (corresponding to nucleotides 885 to 1485 of SEQ ID NO: 8) was subcloned into plasmid pBTM116 linearized with the same enzymes to produce the plasmid designated pBTM116::Non-catalytic encoding lexA sequences fused 5' to HRR25 sequences.

To construct a fusion with the *S. cerevisiae* NUF1 isoform of CKI in plasmid pBTM116, a SmaI site (underlined) was introduced by site-directed mutagenesis in place of the initiating ATG and second codon of NUF1 DNA (SEQ ID NO: 17) using the oligonucleotide:
5'-TGA AGA TCG TTG GCC CGG GTT TCC TTA TCG TCC-3'
(SEQ ID NO. 18).
The resulting product was digested with SmaI and BamHI and the NUF 1 fragment was ligated into pBTM116 linearized with the same enzymes sites to produce the plasmid designated pBTM116::NUF1 encoding lexA sequences fused 5' to NUF1 sequences.

To construct a fusion with the *S. pombe* Hhp1 isoform of CKI in plasmid pBTM116, a SmaI site (underlined) was introduced by site-directed mutagenesis in place of the initiating ATG and second codon of Hhp1 DNA (SEQ ID NO: 19) using the oligonucleotide:
5'-GGG TTA TAA TAT TAT CCC GGG TTT GGA CCT CCG G-3'
(SEQ ID NO. 20).
The resulting product was digested with SmaI and BamHI and the HhpI fragment was ligated into pBTM116 linearized with the same enzymes to produce plasmid pBTM116::Hhp1 encoding lexA sequences fused 5' to Hhp1 sequences.

Assays

To measure protein/protein interaction levels between wild-type and mutant CKI isoforms and TIH proteins of the invention, standard yeast mating techniques were used to generate yeast strains containing all pairwise combinations of the isoforms and TIH proteins. All CKI isoform-encoding pBTM116-based plasmids were transformed into yeast by lithium acetate-mediated transformation methods and transformants were selected on SD-tryptophan medium (Bio101, La Jolla, Calif.). The yeast strain CTY10-5d used for pBTM116-based transformations was mating type a. All TIH protein-encoding pGAD-based plasmids described in Example 1 were transformed using the lithium acetate method into yeast and transformants were selected on SD-leucine medium. The yeast strain used for pGAD-based transformations was mating type a. This MATa strain is isogeneic to CTY10-5d and was constructed by introducing the HO gene using plasmid pGALHO [Jenson and Herskowitz, Meth.Enzymol. 194:132–146 (1991)] in lithium acetate-mediated transformation, inducing the HO gene with galactose to cause a mating-type interconversion, and growing the strain non-selectively to isolate a derivative that had switched mating type.

To construct pairwise combinations between pBTM116-based plasmids and pGAD-based plasmids, yeast strains of opposite mating types were replica plated in a crossed pattern on YEPD medium (Bio101) and were allowed to mate for 18 hours. Diploid cells were selected by a second replica plating onto SD-leucine, -tryptophan medium to select for cells that contained both pBTM116-type and pGAD-type plasmids. The isolated diploids were grown in liquid SD-leucine, -tryptophan medium to a cell density of $2\times10^7$ cells/ml and the level of interaction of the kinase and interacting protein, as determined by beta-galactosidase activity, was determined from cells that were lysed by adding 3 drops of chloroform and 50 µl of 0.1 % SDS to $2\times10^6$ cells suspended in 0.1 ml of Z buffer and subsequently adding 0.2 ml of the chromogenic substrate o-nitrophenyl-β-D-galactoside. β-galactosidase assays were terminated by adding 0.5 ml of 1M $Na_2CO_3$ and activity was measured by reading absorbance at 420 nm using a Milton Roy spectrophotometer (Rochester, N.Y.). In this assay, the degree of protein/protein interaction is directly proportional to the level of β-galactosidase activity. The relative β-galactosidase activity measurements obtained are given in Table 1, wherein a value of <5 indicates that the level of β-galactosidase activity was not greater than background and a value of 10 indicates a easily detectable level of activity. Values were normalized to vector alone controls.

TABLE 1

Yeast CKI/TIH Protein Interactions

| PLASMID CONSTRUCTS ASSAYED | pGAD ::TIH1 | pGAD ::TIH2 | pGAD ::TIH3 |
|---|---|---|---|
| pBTM116 | <5 | <5 | <5 |
| pBTM116:HRR25 | 850 | 650 | 100 |
| pBTM116::HRR2S K→R | 100 | 150 | 30 |
| pBTM116::Kinase Domain | 820 | 160 | 130 |
| pBTM116::Non-catalytic | <5 | <5 | <5 |
| pBTM116::NUF1 | <5 | <5 | 10 |
| pBTM116::Hhp1 | <5 | 20 | 450 |

The results show significant interaction between HRR25 protein kinase and the TIH genes. Furthermore, the interaction appeared to require an active protein kinase; the region of HRR25 that interacted with the TIH proteins is localized to the protein kinase domain of HRR25. TIH proteins of the invention also interacted with other CKI isoforms. For example, TIH3 interacted with NUF1, and TIH2 and TIH3 interacted with HhpI.

EXAMPLE 3

Because HRR25 mutants (hrr25) show chromosome segregation defects and because kinesins are involved in chromosome segregation, the interaction of several different kinesins with the CKI bait fusions described in Example 2 was examined. To date, the kinesin gene family in yeast includes proteins designated KIP1 (Roof et al. supra), KIP2 (Roof et al., supra), CIN8 [Hoyt et al., J. Cell. Biol. 11 (1): 109–120 (1992)] and KAR3 [Meluh et al., Cell 60(6): 1029–1041 (1990)]. To construct the prey kinesin fusion plasmids, genomic clones of KIP1, KIP2, CIN8, and KAR3 were first isolated and then subcloned into plasmid pGAD which contains the transactivating domain of GAL4. Interactions of the CKI bait fusions with the TIH4 prey fusion (pGAD::TIH4) described in Example 1 were examined concurrently.

Plasmid Construction

KIP1 sequences were amplified from S. cerevisiae genomic DNA using the following two primers:
5'-TCC CTC TCT AGA TAT GGC GAG ATA GTT A-3' (SEQ ID NO: 21) and
5'-GTT TAC ACT CGA GGC ATA TAG TGA TAC A-3' (SEQ ID NO: 22).

The amplified fragment was labelled with $^{32}P$ by random primed labelling (Boehringer Mannheim, Indianapolis, Ind.) and used to screen a yeast genomic library constructed in the plasmid pRS200 (ATCC 77165) by colony hybridization. Hybridizations were performed at 65° C. for 18 hours in 6× SSPE (20× SSPE is 175.3 g/l NaCl, 27.6 g/l $NaH_2PO_4.H_2$), 7.4 g.l EDTA, pH7.4, 100 µg/ml salmon sperm carrier DNA, 5× Denhardts Reagent (50× Denhardts is 5% ficoll, 5% polyvinyl pyrolidonae, 5% bovine serum albumin), 0.1% SDS, and 5% sodium dextran sulfate. Filters were washed four times in 0.1× SSPE, 1 % SDS. Each wash was at 65° C. for 30 minutes. Two rounds of site-directed mutagenesis were then performed as described in Example 2 to introduce BamHI sites at the start and end of KIP1 coding sequences (SEQ ID NO: 23). Mutagenesis was performed using a Muta-gene Mutagenesis Kit, Version 2 (BioRad). The oligonucleotide for introducing a BamHI site (underlined) in place of the KIP1 ATG and second codon was:
5'-GAT AGT TAA <u>GGA TCC</u> ATG GCT CGT TCT TCC TTG CCC AAC CGC-3' (SEQ ID NO: 24),
and the oligonucleotide encoding a stop codon (double underlined) and BamHI site (underlined) was:
5'-AAA CTT CAT CAA TGC GCC CGC TAA GG G GAT CCA GCC <u>ATT</u> GTA AAT-3' (SEQ ID NO: 25).

The resulting KIP1 product was digested with BamHI and cloned into pGAD immediately downstream of GAL4 sequences and the plasmid was called pGAD::KIP1.

KIP2 sequences were amplified from S. cerevisiae genomic DNA using the following two primers:
5'-TTT CCT TGT TTA TCC TTT TCC AA-3' (SEQ ID NO: 26) and
5'-GAT CAC TTC GGA TCC GTC ACA CCC AGT TAG-3' (SEQ ID NO: 27).

The amplified fragment was labelled with $^{32}p$ by random primed labelling and used to screen a yeast genomic library constructed in the plasmid $YC_p50$ (ATCC 37415) by colony hybridization. Hybridizations and washes were as described above for KIP1. Two rounds of site-directed mutagenesis were performed to introduce BamHI sites at the start and end of KIP2 coding sequences (SEQ ID NO: 28). The oligonucleotide for introducing a BamHI site (underlined) in place of the KIP2 ATG and second codon was:
5'-ACC ATA ATA CCA <u>GGA TCC</u> ATG ATT CAA AAA-3' (SEQ ID NO: 29)
and the oligonucleotide encoding a BamHI site (underlined) was:
5'-CCT GTC GTG GAT AGC GGC CGC TA<u>G GAT CCT</u> GAG GGT CCC AGA-3' (SEQ ID NO: 30).
The resulting KIP2 product was digested with BamHI and cloned into pGAD immediately downstream of GAL4 sequences and the plasmid was called pGAD::KIP2.

CIN8 sequences were amplified from *S. cerevisiae* genomic DNA using the following two primers:
5'-ACA TCA TCT AGA GAC TTC CTT TGT GAC C-3' (SEQ ID NO: 31) and
5'-TAT ATA ATC GAT TGA AAG GCA ATA TC-3' (SEQ ID NO: 32).

The amplified fragment was labelled with $^{32}P$ by random primed labelling and used to screen a yeast genomic library constructed in the plasmid pRS200 (ATCC 77165) by colony hybridization. Hybridizations and washes were as described above for KIP1. Two rounds of site-directed mutagenesis were performed to introduce BamHI sites at the start and end of CIN8 coding sequences (SEQ ID NO: 33). The oligonucleotide utilized for introducing a BamHI site (underlined) in place of the CIN8 ATG and second codon was:
5'-CGG GTG TA<u>G GAT CC</u>A TGG TAT GGC CAG AAA GTA ACG-3' (SEQ ID NO: 34)
and the downstream oligonucleotide encoding a BamHI site (underlined) and a stop codon (double underlined) was:
5'-GTG GAC AAT GGC GGC CGC AGA AAA A<u>GG ATC C</u>AG ATT GAA <u>TAG</u> TTG ATA TTG CC-3' (SEQ ID NO: 35).

The resulting CIN8 product was digested with BamHI and cloned into pGAD immediately downstream of GAL4 sequences and the plasmid was called pGAD::CIN8.

KAR3 was amplified from *S. cerevisiae* genomic DNA using the following two primers:
5'-GAA TAT TCT AGA ACA ACT ATC AGG AGT C-3' (SEQ ID NO: 36) and
5'-TTG TCA CTC GAG TGA AAA AGA CCA G-3' (SEQ ID NO: 37).

The amplified fragment was labelled with $^{32}P$ by random primed labelling and used to screen a yeast genomic library constructed in the plasmid pRS200 (ATCC 77165) by colony hybridization. Hybridizations and washes were as described above for KIP1. Two rounds of site-directed mutagenesis were performed to introduce BamHI sites at the start arid end of KAR3 coding sequences (SEQ ID NO: 38). The oligonucleotide for introducing a BamHI site (underlined) in place of the KAR3 ATG and second codon was:
5'-GAT AGT TAA <u>GGA TCC</u> ATG GCT CGT TCT TCC TTG CCC AAC CGC-3' (SEQ ID NO: 39) and the oligonucleotide encoding a BamHI site (underlined) and a stop codon (double underlined) was:
5'-AAA CTT CAT CAA TGC GGC CGC TAA GG<u>G GAT CC</u>A GCC ATT <u>GTA</u> AAT-3' (SEQ ID NO: 40).

The resulting KAR3 product was digested with BamHI and cloned into pGAD immediately downstream of GAL4 sequences and the plasmid was called pGAD::KAR3.

The prey plasmids were transformed into yeast by lithium acetate-mediated transformation and the transformants were mated to CKI isoform-encoding yeast strains as described in Example 2. β-galactosidase activity of CKI isoform/TIH-containing strains was determined from cells that were lysed by adding 3 drops of chloroform and 50 μl of 0.1% SDS to $2\times10^6$ cells suspended in 0.1 ml of Z buffer and subsequently adding 0.2 ml of the chromogenic substrate o-nitrophenyl-β-D-galactoside. β-galactosidase assays were terminated by adding 0.5 ml of 1M $Na_2CO_3$ and activity was measured by reading absorbance at 420 nm using a Milton Roy spectrophotometer (Rochester, N.Y.). In this assay, the degree of protein/protein interaction is directly proportional to the level of β-galactosidase activity. The results of the assay are presented as units of β-galactosidase activity in Table 2.

TABLE 2

| | β-Galactosidase Activity Resulting From CKI Isoform/Kinesin Interaction | | | | |
|---|---|---|---|---|---|
| | pGAD::KIP1 | pGAD::KIP2 | pGAD::TIH4 | pGAD::KAR3 | pGAD::CIN8 |
| pBTM116::HRR25 | 16 | 10 | 70 | 15 | 5 |
| pBTM116::HRR25 K→R | 55 | 16 | 66 | 75 | 28 |
| pBTM116::Non-Catalytic | 70 | <0.1 | <0.1 | 60 | <0.1 |

The results indicate that HRR25 can interact with all four yeast kinesins and TIH4. Kinesins KIP2 and CIN8 interact with the catalytic domain of HRR25 while kinesins KIP1 and KAR3 interact with kinase-inactive HRR25 and with the non-catalytic domain of HRR25, suggesting that kinase/substrate interaction progresses through strong binding to enzymatic activity. In addition, the results show that HRR25 interacts with the carboxy-terminal portion of TIH4 or, because TIH4 corresponds to KIP2, KIP2.

EXAMPLE 4

Assays were also performed to determine whether human CKI isoforms would interact with the TIH proteins of the invention. Two human CKI isoforms, CKIα3 (CKIα3Hu) and CKIδ (CKIδHu), were selected for this analysis. The human CKI genes were fused to the GAM4 DNA binding domain previously inserted into plasmid pAS [Durfee, et al., *Genes and Development* 7:555–569 (1993)] to produce pAS::CKIα3 and pAS::CKIδ.

Specifically, the CKIα3Hu isoform-encoding DNA (SEQ ID NO: 41) was subjected to site-directed mutagenesis using the mutagenic oligonucleotide:
5'-CTT CGT CTC TCA <u>CAT ATC</u> GGC GAG TAG CAG CGG C-3'
(SEQ ID NO. 42)
to create NdeI site (underlined) in the place of the CKIα3Hu initiating methionine and second codon, and the resulting DNA was digested with NdeI and ligated into plasmid pAS at a NdeI site located immediately downstream of GAL4 sequences.

CKIδHu DNA (SEQ ID NO: 43) was introduced into pAS by amplifying the CKIδ cDNA with mutagenic oligonucleotide primers that contained BamHI sites. The oligonucleotides, with BamHI sites underlined, used were:
5'-CGC <u>GGA TCC</u> TAA TGG AGG TGA GAG TCG GG-3' (SEQ ID NO. 44),
replacing the initiating methionine and second codon,
and
5'-CGC <u>GGA TCC</u> GCT CAT CGG TGC ACG ACA GA-3' (SEQ ID NO. 45).

Reactions included 200 mM Tris HCl (pH 8.2), 100 mM KCl, 60 mM $(NH_4)_2SO_4$, 15 mM $MgCl_2$, 1% Triton X-100, 0.5 μM primer, 100 ng template, 200 μM dNTP and 2.5 units polymerase. The reactions were performed for 30 cycles. Reactions were started at 94° C. for 4 minutes and all subsequent cycles were 1 minute at 94° C. for denaturing, 2 minutes at 50° C. for annealing, and 4 minutes at 72° C. for extension. The amplified product was digested with BamHI and ligated into BamHI-digested pAS immediately downstream of GAL4 sequences to create plasmid pAS:CKIδ.

The resulting bait plasmids were transformed into yeast by lithium acetate-mediated transformation and the transformants were mated to TIH-encoding yeast strains as described in Example 2. β-galactosidase activity of CKIα3Hu- or CKIδHu-containing/TIH-containing strains was detected by replica plating cells onto Hybond-N$^{0.45\mu}$ filters (Amersham, Arlington Heights, Ill.), growing cells on the filters at 30° C. for 18 hours, lysing the colonies by freezing the filters in liquid nitrogen, and incubating the filters on Whatman filter paper soaked in Z buffer containing 0.002% X-gal. Reactions were terminated by soaking the filters in 1M $Na_2CO_3$ and protein/protein interaction was evaluated by examining for a chromogenic conversion of X-gal to blue by β-galactosidase activity. The results of the assay, as determined by visual screening for development of blue color are presented below in Table 3.

TABLE 3

β-Galactosidase Activity Resulting From Human CKI/TIH Interaction

| PLASMID CONSTRUCTS USED | TIH1 | TIH2 | TIH3 |
| --- | --- | --- | --- |
| pAS::CKIα3 | − | − | − |
| pAS::CKIδ | − | + | − |

These results indicate that interaction between TIH proteins of the invention and CKI isoforms is not limited to yeast isoforms. CKIδHu interacted with TIH2. Thus, CKI/TIH interactions can be expected to occur between human CKIs and their cognate TIH proteins.

EXAMPLE 5

Full length genomic (clones encoding the yeast TIH1, TIH2, and TIH3 proteins were isolated from a yeast genomic library. To identify genomic clones, radiolabelled PCR fragments were prepared from the pGAD plasmids containing TIH1, TIH2, and TIH3 fusion genes described in Example 1. The sequence of the unidirectional oligonucleotide used to amplify the clones was:
5'-GGA ATC ACT ACA GGG ATG-3' (SEQ ID NO. 46). PCR reactions included 200 mM Tris HCl (pH 8.2), 100 mM KCl, α mM $(NH_4)_2SO_4$, 15 mM $MgCl_2$, 1% Triton X-100, 0.5 μM primer, 100 ng template, 200 μM dNTP and 2.5 units polymerase. The reactions were performed for 30 cycles. The first five cycles contained 50 μCi each $^{32}$P-dCTP and $^{32}$P-TTP. At the start of the sixth cycle, non-radiolabeled dCTP and dTTP were each added to 200 μM final concentration. Reactions were started at 94° C. for 4 minutes and all subsequent cycles were performed for 1 minute at 94° C. for denaturation, 2 minutes at 50° C. for annealing, and 4 minutes at 72° C. for extension. The resulting PCR products were then used as probes in colony hybridization screening.

The full length TIH1 genomic clone was isolated from a YCp50 plasmid library (ATCC 37415). The full length TIH2 and TIH3 genomic clones were isolated from a λ genomic library [Riles, et al., Genetics 134:81–150 (1993)]. Hybridization for YCp50 library screening were performed at 65° C. for 18 hours in 6× SSPE (20× SSPE is 175.3 g/l NaCl, 27.6 g/l $NaH_2PO_4.H_2$), 7.4 g.l EDTA, pH7.4, 100 μg/ml salmon sperm carrier DNA, 5× Denhardts Reagent (50× Denhardts is 5% ficoll, 5% polyvinyl pyrolidone, 5% bovine serum albumin), 0.1% SDS, and 5% sodium dextran sulfate. Filters were washed four times in 0.1× SSPE, 1% SDS. Each wash was at 65° C. for 30 minutes. Hybridization conditions for λ library screening were 18 hours at 64° C. in 1× HPB (0.5M NaCl, 100 mM $Na_2HPO_4$, 5 mM $Na_2EDTA$), 1 % sodium sarkosyl, 100 μg/ml calf thymus DNA. Filters were washed two times for 15 seconds, one time for 15 minutes, and one time for 15 seconds, all at room temperature in 1 mM Tris-HCl (pH 8.0). The sequences of TIH1, TIH2, and TIH3 genomic clones were determined by automated DNA sequencing with an ABI 373A sequencer (Applied Biosystems). Nucleotide sequences determined for the full length TIH1, TIH2 and TIH3 genomic clones are set out in SEQ ID NOS: 2, 4, and 6, respectively; the deduced amino acid sequences for TIH1, TIH2, and TIH3 are set out in SEQ ID NOS: 3, 5, and 7. respectively. Database searches confirmed the results from Example 1 that the TIH1 and TIH3 genes encoded novel proteins showing no significant homology to any protein in the GenBank database.

EXAMPLE 6

To characterize activity of the TIH proteins and to determine if the TIH proteins participate in a HRR25 signalling pathway, a chromosomal TIH1 deletion mutant was constructed by homologous recombination.

Specifically, the TIH1 mutation was constructed by subcloning a 1.7 kb SalI-BamHI fragment that encompasses the genomic TIH1 gene into plasmid pBluescript II SK (Stratagene, La Jolla, Calif.). The resulting subclone was digested with EcoRV and PstI to delete 0.5 kb of the TIH1 gene (nucleotides 1202 to 1635 of SEQ ID NO: 2) and into this region was ligated a 2.2 kb SmaI-PstI fragment that contained the S. cerevisiae LEU2 gene. Isolated DNA from the resulting plasmid construct was digested with BamHI to linearize the plasmid and 10 μg of this sample were used to transform a diploid yeast strain that is heterozygous for HRR25 (MAT a/MAT α ade2/ade2 can1/can1 his3-11,15/his3-11,15 leu2-3,112/leu2-3,112 trp1-1/trp1-1 ura3-1/ura3-1 HRR25/hrr25::URA3) to Leu$^+$. Transformation was carried out using lithium acetate-mediated procedures and transformants were selected on SD-Leucine medium (Bio101). Yeast transformation with linearized DNA results in homologous recombination and gene replacement [Rothstein, Meth. Enzymol. 194:281–301 (1991)]. Stable Leu$^+$ colonies were replica plated onto sporulation medium (Bio101) and grown at 30° C. for five days. Spores were microdissected on YEPD medium (Bio101) using a tetrad dissection apparatus [Sherman and Hicks, Meth. Enzymol. 194:21–37 (1991)] and isolated single spores were allowed to germinate and grow into colonies for three days.

Four colony types were detected due to random meiotic segregation of the heterozygous TIH1 and HRR25 mutations present in the strain. The hrr25 deletion mutation in the parent strain was due to a replacement of the HRR25 gene with the yeast URA3 gene and the TIH1 mutation is due to a replacement with LEU2. URA3 and LEU2 confer uracil and leucine prototropy, respectively. The colony types are represented b) segregation of the mutations into following genotypic configurations: (i) wild type cells are HRR25 TIH1; (ii) HRR25 mutants are hrr25::URA3 TIH1; (iii) TIH1 mutants are HRR25 tih1::LEU2; and (iv) HRR25 TIH 1 double mutants are hrr25::URA3 tih 1::LEU2. Standard physiological analyses of yeast mutant defects were performed [Hoekstra et al., supra].

TIH1 deletion mutants exhibited phenotypes identical to mutations in HRR25 including slow growth rate, DNA repair defects, and aberrant cellular morphology, indicating that the TIH proteins participate in the same pathway as HRR25 or in pathways having similar effects. Furthermore, tih1 hrr25 double mutants were inviable.

EXAMPLE 7

To confirm the dihybrid screen analysis of interaction between CKI protein kinases and TIH proteins, a biochemical method was developed to detect the interaction. This method was based on affinity purification of one component in the interaction, followed by Western blotting to detect the presence of the interacting component in the affinity purified mixture. The TIH2 gene was used to construct a TIH2/glutathione-S-transferase (GST) fusion protein which could be affinity purified with glutathione agarose (Pharmacia, Uppsala, Sweden) Other useful ligand/counterreceptor combinations include, for example, influence virus hemagglutinin [Field et al., Mol. Cell Biol. 8(5): 2159–2165 (1988)]/hemagglutinin-specificantibody (Berkeley Antibody Company, Richmond, Calif.), polyhistidine/nickel affinity chromatography (Novagen, Madison, Wis.), and maltose-binding protein/amylose chromatography (New England Biolabs, Beverly, Mass.).

To construct the GST::TIH2 fusion protein, the 5' and 3' termini of the TIH2 gene were modified by DNA amplification-based mutagenesis procedures. The amplifying oligonjcleotides introduced XbaI and HindIII sites for ease in subcloning. The oligoriucleotides, with restriction sites underlined, used for amplification were:
5'-AT<u>T CTA GAC</u> ATG GAG ACC AGT TCT TTT GAG-3' (SEQ ID NO: 47) and,
5 '-TGG <u>AAG CTT</u> ATA TTA CCA TAG ATT CTT CTT G-3' (SEQ ID NO: 48).
Reactions included 200 mM Tris-HCl (pH 8.2), 100 mM KCl, 60 mM (NH$_4$)$_2$SO$_4$, 15 mM MgCl$_2$, 1% Triton-X-100, 5 µM primer, 100 ng template, 200 µM dNTP and 2.5 units polymerase. The reactions were performed for 30 cycles. Reactions were started at 94° C. for 4 minutes and all subsequent cycles were 1 minute at 94° C. for denaturation, 2 minutes at 50° C. for annealing, and 4 minutes at 72° C. for extension.

The resulting amplifieti product was digested with XbaI and HindIII and the fragment was subcloned into the GST-containing plasmid pGEXKG, which contained a galactose-inducible GST gene, to create pGEXKG::TIH2. This plasmid contains, in addition to the ,GST sequences fused immediately upstream of TIH2 sequences, URA3 and LEU2 selectable markers for yeast transformation. Plasmid pGEXKG::TIH2 was then transformed by lithium acetate-mediated transformation into yeast strain W303 [Wallis, et al., Cell 58:409–419 (1989)] and Ura$^+$ transformants were selected on SD-URA medium (Bio101). To isolate the GST::TIH2 fusion protein, 100 ml SD-URA broth was inoculated with the transformed yeast and grown to a density of 1×10$^7$ cells/ml in the presence of galactose. The cells were then pellet by centrifugation, washed in lysis buffer [10 mM sodium phosphate pH 7.2, 150 mM NaCl, 1 % Nonidet P-40, 1 % Trasylol (Miles), 1 mM dithiothreitol, 1 mM benzamidine, 1 mM phenylmethyl sulphonyl fluoride, 5 mM EDTA, 1 µg/ml pepstatin, 2 µg/ml pepstatin A, 1 µg/ml leupeptin, 100 mM sodium vanadate, and 50 mM NaF], resuspended in 1 ml lysis buffer, and lysed by vortexing for 5 minutes with 10 g of glass beads. The crude lysate was clarified by centrifugation at 100,000×g for 30 minutes. Fifty µl of 50% slurry glutathione agarose (Pharmacia) was added to the extract and the mixture incubated for 1 hour. The agarose was pelleted by a 10 second spin in an Eppendorf microcentrifuge, the supernate removed, and the agarose-containing pellet washed with phosphate-buffered saline (PBS). The pellet was resuspended in 50 µl of 2× protein gel sample buffer, boiled for 2 minutes, and 12.5 µl was electrophoresed through a 10% polyacrylamide gel. Gel fractionated proteins were transferred by electroblotting, to Immobilon-P membranes (Millipore, Bedord, Mass.) and HRR25 was detected by probing the membrane with a rabbit antibody [DeMaggio et al., Proc. Natl. Acad. Sci. (USA) 89: 7008–7012 (1992)] raised to HRR25. The Western blot was developed for immunoreactivity using an alkaline phosphatase-conjugated secondary antibody and colorimetric development (BioRad).

A photograph of the gel is presented in FIG. 1, wherein the approximately 58 kD HRR25 protein was detected in association with TIH2 protein.

EXAMPLE 8

In order to confirm the novelty of the identified TIH1 protein, a data base search of previously reported protein sequences was performed. As shown in FIG. 2, wherein portions of the amino acids sequence of TIH1 (amino acids 128 to 161 in SEQ ID NO: 3), human Hum80DP (amino acids 31 to 63) [Sakumi, et al., J.Biol.Chem. 268:23524–23530 (1993)], E.coli MutT (amino acids 32- to 64) [Akiyama, et al., Mol. Gen. Genet. 206:9–16 (1989)], viral C11 (amino acids 122 to 154) [Strayer, et al., Virol. 185:585–595 (1991)] and viral VD10 (amino acids 122 to 154) [Stayer, et al., (1991), supra)] are respectively set out, sequence comparison indicated that TIH1 contains a signature sequence motif associated with enzymes which actively participate in removal of oxidatively damaged nucleotides from the nucleus, thus increasing the fidelity of DNA replication. Enzymes with this activity have been identified in a wide range of organisms, including prokaryotes, eukaryotes and viruses [Koonin, Nucl. Acids Res. 21:4847 (1993)].

HRR25 enzyme activity has been shown to participate in repair of DNA damaged by radiation, however the role of HRR25 in the repair process has not been determined. The fact that TIH1 has an amino acid sequence similar to that of enzymes capable of degrading damaged DNA indicates that TIH1 is likely to interact with HRR25 in the DNA repair process. Inhibitor compounds which are capable of interfering, or abolishing, the interaction between HRR25 and TIH1 would thus be particularly useful in targeted cancer and antiviral therapy. Delivery of an inhibitor to cancerous or virus-infected cells would increase the rate of replicative mutation in the cells, thus increasing the likelihood of induced cell suicide. In addition, targeted delivery of an inhibitor would selectively confer enhanced sensitivity of cancerous or virus-infected cells to treatment with conventional chemotherapy and/or radiation therapy, thus enhancing the chemotherapy and/or radiotherapy therapeutic index.

While the present invention has been described in terms of specific methods and compositions, it is understood that variations and modifications will occur to those skilled in the art. Therefore, only such limitations as appear in the claims should be placed on the invention.

What is claimed is:

1. A purified and isolated polynucleotide encoding an *S. cerevisiae* TIH1 polypeptide.

2. A purified and isolated polynucleotide encoding the TIH1 amino acid sequence set out in SEQ ID NO: 3.

3. The polynucleotide of claim 2 which is a DNA.

4. The polynucleotide of claim 2 which is cDNA.

5. The polynucleotide of claim 2 which is genomic DNA.

6. The polynucleotide of claim 2 which is chemically synthesized DNA.

7. A purified and isolated TIH1 polynucleotide comprising the TIH1 DNA sequence set out in SEQ ID NO: 2.

8. A DNA expression construct comprising a DNA according to claim 3 or 7.

9. A host cell transformed with a DNA according to claim 3 or 7.

10. A method for producing a TIH1 polypeptide comprising growing a host cell according to claim 9 in a suitable medium and isolating TIH1 polypeptide from said host cell or the medium of its growth.

* * * * *

UNITED STATES PATENT AND TRADEMARK OFFICE
CERTIFICATE OF CORRECTION

PATENT NO. : 5,846,764
DATED : December 8, 1998
INVENTOR(S) : DeMaggio, et. al.

It is certified that error appears in the above-indentified patent and that said Letters Patent is hereby corrected as shown below:

As per IDS/1449 dated 5/3/95 in Other Publications on pg. 2 under Ito et al. replace "alkl:" with "alkal:"

As per IDS/1449 dated 5/3/95 in Other Publications on pg. 2 under Sakumi et al. after "," and before "cloning" insert '-- "--.

Column 9, line 51, replace "pBTM116:HRR25 K-R" with "pBTM116:HRR 25 K-R"

Column 10, line 28, replace "pyrolidonae" with "pyrolidone"

Column 10, line 42, replace "GCC" with "GGC"

Column 10, line 43, replace "ATT" with "ATT"

Column 11, line 44, replace "arid" with "and"

Column 12, line 38, replace "GAM 4 with "GAL 4"

Column 12, line 45, replace "ATC" with "ATG"

Column 13, line 3, replace "amplilied" with "amplified"

Column 13, line 38, delete "(" before "clones"

Column 13, line 43, replace "oligoriucleotide" with "oligonucleotide"

Column 13, line 47, replace "x" with "60"

Column 14, line 58, replace "b)" with "by"

UNITED STATES PATENT AND TRADEMARK OFFICE
CERTIFICATE OF CORRECTION

PATENT NO. : 5,846,764
DATED : December 8, 1998
INVENTOR(S) : DeMaggio, et. al.

It is certified that error appears in the above-indentified patent and that said Letters Patent is hereby corrected as shown below:

Column 15, line 27, replace "oligonjcleotides" with "oligonucleotides"

Column 15, line 28, replace "oligoriucleotides" with "oligonucleotides"

Column 15, line 43, replace "amplifiet:" with "amplified"

Column 15, line 47, after "the" and before "GST" delete ","

Column 15, line 57, replace "pellet" with "pelleted"

Signed and Sealed this

Tenth Day of April, 2001

Attest:

NICHOLAS P. GODICI

Attesting Officer   Acting Director of the United States Patent and Trademark Office